United States Patent
Zhang et al.

(10) Patent No.: US 7,994,115 B2
(45) Date of Patent: Aug. 9, 2011

(54) THREE-DIMENSIONAL STRUCTURES OF TALL-1 AND ITS COGNATE RECEPTORS AND MODIFIED PROTEINS AND METHODS RELATED THERETO

(75) Inventors: Gongyi Zhang, Denver, CO (US);
Hong-Bing Shu, Denver, CO (US);
Yingfang Liu, Denver, CO (US);
Liangguo Xu, Denver, CO (US)

(73) Assignee: National Jewish Health, Denver, CO (US)

( * ) Notice: Subject to any disclaimer, the term of this patent is extended or adjusted under 35 U.S.C. 154(b) by 434 days.

(21) Appl. No.: 12/061,922

(22) Filed: Apr. 3, 2008

(65) Prior Publication Data

US 2008/0306000 A1    Dec. 11, 2008

Related U.S. Application Data

(63) Continuation of application No. 10/281,053, filed on Oct. 24, 2002, now Pat. No. 7,825,089.

(60) Provisional application No. 60/403,364, filed on Aug. 13, 2002, provisional application No. 60/354,966, filed on Feb. 7, 2002, provisional application No. 60/348,962, filed on Jan. 14, 2002, provisional application No. 60/345,106, filed on Oct. 24, 2001.

(51) Int. Cl.
*A61K 38/00* (2006.01)

(52) U.S. Cl. ........................................................ 514/1.1

(58) Field of Classification Search ........................ None
See application file for complete search history.

(56) References Cited

U.S. PATENT DOCUMENTS

| | | | |
|---|---|---|---|
| 6,297,367 B1 | 10/2001 | Tribouley | |
| 6,403,770 B1 | 6/2002 | Yu et al. | |
| 6,475,987 B1 | 11/2002 | Shu | |
| 6,812,327 B1 | 11/2004 | Yu et al. | |
| 2003/0099990 A1 | 5/2003 | Shu | |
| 2003/0148445 A1 | 8/2003 | Shu | |
| 2007/0015695 A1 | 1/2007 | Zhang et al. | |

FOREIGN PATENT DOCUMENTS

| | | |
|---|---|---|
| WO | WO 00/43032 | 7/2000 |
| WO | WO 00/68378 | 11/2000 |
| WO | WO 02/16412 A2 | 2/2002 |
| WO | WO 03/022877 A1 | 3/2003 |

OTHER PUBLICATIONS

Roschke et al., J. Immunol., vol. 169, 4314-4321, 2002.
Liu et al., Cell, vol. 108, 383-394, 2002.
Thompson et al., Science, vol. 293, 2108-2111, 2001.
Khare et al., Trends in Immunology, vol. 22, No. 2, 61-63, 2001.
Yu et al., Dept. of Inflammation, Process Science, Protein Chemistry, Pharmacology and Pathology, Amgen Inc., 252-256, 2000.
Yan et al., Nature Immunology, vol. 1(1), 37-41, 2000.
Xia et al., J. Exp. Med., vol. 192(1), 137-143, 2000.
Thompson et al., J. Exp. Med., vol. 192(1), 129-135, 2000.
Shu and Johnson, PNAS, vol. 97(16), 9156-9161, 2000.
Marsters et al., Curr. Biol., vol. 10, 785-788, 2000.
Gross et al., Nature, vol. 404, 995-999, 2000.
Chan et al., Science, vol. 288, 2351-2354, 2000.
Shu et al., J. Leukoc. Biol., vol. 65, 680-683, 1999.
Schneider et al., J. Exp. Med., vol. 189(11), 1747-1756, 1999.
Mukhopadhyay et al., J. Biol. Chem., vol. 274(23), 15978-15981, 1999.
Moore et al., Science, vol. 285, 260-263, 1999.
Holm and Sander, J. Mol. Biol., vol. 233, 123-138, 1993.
Banner et al., Cell, vol. 73, 431-445, 1993.
Eck, et al., "The Structure of Tumor Necrosis Factor-a at 2.6 Å Resolution", The Journal of Biological Chemistry, Oct. 15, 1989, vol. 264, No. 29, pp. 17595-17605.
Karpusas, et al., "Crystal Structure of Extracellular Human BAFF, a TNF Family member that Stimulates B Lymphocytes", Journal of Molecular Biology, Feb. 1, 2002, vol. 315, No. 5, pp. 1145-1154.
Yu, et al., "April and Tall-I and Recceptors BCMA and TACI: System for Regulationg Humoral Immunity", Nature Immunology, Sep. 2000, Cvol. 1, No. 3, pp. 252-256.
Communication for European Patent Application No. 02802221.8, dated May 20, 2009.
Communication for European Patent Application No. 02802221.8, dated Jun. 19, 2008.
Communication for European Patent Application No. 02802221.8, Feb. 26, 2007.
Supplementary European Search Report for European Patent Application No. 02802221.8, dated Jan. 31, 2006.
Supplementary Partial European Search Report for European Patent Application No. 02802221.8, dated Nov. 14, 2005.
International Search Report for International (PCT) Patent Application No. PCT/US02/34376, mailed Dec. 15, 2004. International Preliminary Examination Report for International (PCT) Patent Application No. PCT/US02/34376, mailed Oct. 26, 2005.
Communication for European Patent Application No. 02802221.8, dated May 4, 2010.

*Primary Examiner* — Daniel E Kolker
*Assistant Examiner* — Gregory S Emch
(74) *Attorney, Agent, or Firm* — Sheridan Ross P.C.

(57) ABSTRACT

Disclosed are TALL-1 and TALL-1 receptor protein homologues (agonists and antagonists) designed based on the three-dimensional structure of sTALL-1, eBCMA and eBAFF-R; agonist homologues of APRIL; methods of using wild-type APRIL to inhibit the activity of TALL-1; compositions comprising such homologues, nucleic acid molecules encoding such homologues, and therapeutic methods of using such compounds and compositions. Also disclosed are crystalline complexes of sTALL-1 and sTALL-1 in complex with either BCMA or BAFF-R; models of three-dimensional structures of such crystalline complexes and related structures, methods of drug design using any portion of such structures; methods of design and/or identification of regulatory peptides derived from the such structures; compounds identified by drug design using such structures; and the use of such compounds in therapeutic compositions and methods.

11 Claims, 26 Drawing Sheets
(26 of 26 Drawing Sheet(s) Filed in Color)

```
BCMA     8  CSQN..EYFDSLLHACIPCQLRCSSNTPPL.TQQRYC  41
BAFF-R  19  CVPA..ECFDLLVRHCVACGLLRTPRPKPAGASSPAP  53
TACI1   34  CPEE..QYWDPLLGTCMSCKTICNHQSQR..TCAAFC  66
TACI2   71  CRKEQGKFYDHLLRDCISCASICGQHPK...QCAYFC 104
Fn14    36  CSRG..SSWSADLDKCMD.AS.RARPHSD.F.LG.   67
TNF-R1 168  CHMG....FFLRGAKCISCHD.CKN.....KECEKLC 194
```

THREE-DIMENSIONAL STRUCTURES OF TALL-1 AND ITS COGNATE RECEPTORS AND MODIFIED PROTEINS AND METHODS RELATED THERETO

CROSS-REFERENCE TO RELATED APPLICATIONS

This application is a continuation of U.S. application Ser. No. 10/281,053, filed Oct. 24, 2002, which claims the benefit of priority under 35 U.S.C. §119(e) from the following U.S. Provisional Applications: U.S. Provisional Application Ser. No. 60/345,106, filed Oct. 24, 2001; U.S. Provisional Application Ser. No. 60/348,962, filed Jan. 14, 2002; U.S. Provisional Application Ser. No. 60/354,966, filed Feb. 7, 2002; and U.S. Provisional Application Ser. No. 60/403,364, filed Aug. 13, 2002. Each of the above-identified applications is incorporated herein by reference in its entirety.

GOVERNMENT SUPPORT

This invention was made with government support under NIH Grant Nos. GM65341, AI49992, and AI22295, each awarded by the National Institutes of Health. The government has certain rights in the invention.

REFERENCE TO SEQUENCE LISTING

This application contains a Sequence Listing submitted as an electronic text file named "2879_86_1_ST25.txt", having a size in bytes of 25 kb and created on 23 Aug. 2007. the information contained in this electronic file is hereby incorporated by reference in its entirety pursuant to 37 CFR §1.52(e)(5).

REFERENCE TO LENGTHY TABLES

This application contains lengthy Tables submitted as an electronic text file named "2879_86_1_Tables.txt", having a size in bytes of 2.12 Mb and created on 24 Aug. 2007. the information contained in this electronic file is hereby incorporated by reference in its entirety pursuant to 37 CFR §1.52(e)(5).

FIELD OF THE INVENTION

This invention generally relates to the three-dimensional structure of sTALL-1 and sTALL-1 in complex with the extracellular domains of its cognate receptors, BCMA and BAFF-R, and to the use of such structures to develop agonists and antagonists and lead compounds for drug development in the area of therapeutic agents related to TALL-1 biological activity.

BACKGROUND OF THE INVENTION

TNF (tumor necrosis factor) family ligands and their corresponding receptors (TNFR) play pivotal roles in mammalian cell host defense processes, inflammation, apoptosis, autoimmunity, and organogenesis. There are at least 18 TNF ligands and 27 receptors identified so far. Some ligands have multiple receptors, and some receptors also bind multiple ligands. The interactions between ligands and receptors are usually very specific and have high apparent affinity (0.1 nM-1 nM) (Locksley et al., 2001, *Cell* 104:487-501; Fesik et al., 2000, *Cell* 103:273-282).

The first TNF ligand trimer structure (TNFα) was determined more than a decade ago (Jones et al., 1989, *Nature* 338:225-228; Eck et al., 1989, *J. Biol. Chem.* 264:17595-17605). It consists entirely of β strands and loops. The structure has a standard 'jellyroll' topology and is remarkably similar to capsid proteins of small RNA viruses such as satellite tobacco necrosis virus (Jones et al., 1984, *J Mol Biol* 177: 735-767). Three monomers of TNFα form a trimer through highly conserved hydrophobic surfaces. The trimer also exists in solution. Structures of TNFβ, CD40L, and TRAIL were subsequently determined (Eck et al., 1992, *J. Biol. Chem.* 267:2119-2122; Karpusas et al., 1995, *Structure* 3:1031-1039; Cha et al., 1999, *Immunity* 11:253-261). These structures are similar to the TNFα structure, although the sequence homology is low (20-25%) among the TNF family members. These studies led to proposals that all TNF family members have similar structures and function as trimers (Locksley et al., 2001, supra; Fesik, 2000, supra). Due to the scarcity of available structures (4 of 18) and low sequence homology among the TNF family members, the generality of this conclusion is unclear.

The structure of the complex of TNFβ and cysteine-rich domains (CRDs) from its cognate receptor, TNFR1, has also been determined (Banner et al., 1993, *Cell* 73:431-445). The structure showed that the three elongated receptor domains bind to one TNF trimer at the interfaces formed between the TNF monomers. Two CRDs (CRD2 and CRD3) make contacts with two distinct regions of TNFβ. The recently determined complex structure of TRAIL and DR5 disclosed a similar interaction mode as observed in the TNFβ and TNFR1 co-crystal structure, although CRD3 of DR5 assumes a different orientation compared to the one in the TNFβ and TNFR1 structure (Mongkolsapaya et al., 1999, *Nat. Struct. Biol.* 6:1048-1053; Hymowitz et al., 1999, *Mol. Cell.* 4:563-571). It was proposed that the TNF trimeric ligands trigger the trimerization of their cognate receptors, which causes the cytoplasmic regions of the receptor to form a cluster that can recruit adaptor proteins, leading to the activation of downstream signal transduction pathways (Fesik, 2000, supra; Banner, et al., 1993, supra; Mongkolsapaya, et al., 1999, supra; Hymowitz, et al., 1999, supra). This theory is now challenged by new findings showing that TNF receptor and Fas exist in an oligomeric state through the pre-ligand-binding assembly domain (PLAD) before the binding of ligands (Chan et al., 2000, *Science* 288:2351-2354; Siegel et al., 2000, *Nat. Immunol.* 1:469-474).

TALL-1, also known as, BAFF, THANK, BLyS and zTNF4, and its receptors BCMA, BAFF-R and TACI are four recently identified TNF/TNFR (TNF receptor) family members (Shu et al., 1999, *J. Leukocyte Biology* 65:680-683; Schneider et al., 1999, *J Exp Med.* 189:1747-56; Moore et al., 1999, *Science* 285:260-263; Mukhopadhyay et al., 1999, supra; Shu et al., 2000, *Pro. Natl. Acad. Sci. USA* 97:9156-9161; Gross et al., 2000, *Nature* 404:995-999; Thompson et al., 2000, *J Exp Med* 192:129-35; Marsters et al., 2000, *Curr Biol.* 10:785-8; Xia et al., 2000, *J Exp Med.* 192:137-43; Yan et al., 2000, *Nat. Immunol.* 1:37-41; Yu et al., 2000, *Nat Immunol.* 1:252-6; Thompson et al., 2001, *Science* 293:2108-2111; and Yan et al., 2001, *Curr Biol.* 11(19):1547-52). Overexpression of sTALL-1 in mice leads to increased numbers of mature B-lymphocytes, splenomegaly, anti-DNA antibodies, proteinuria, and glomerulonephritis. These phenotypes mimic those of systemic lupus erythematosus (Shu et al., 2000, supra; Gross et al., 2000, supra; Thompson et al., 2000, supra; Marsters et al., 2000, supra; Xia et al., 2000, supra; Yan et al., 2000, supra; Mackay et al., 1999, *J Exp Med* 190:1697-710; Khare et al., 2000, *Proc Natl Acad Sci USA*

97:3370-5). The experiments of BAFF knock-out showed that BAFF was absolutely required for normal B cell development (Schiemann et al., 2001, *Science* 293:2111-2114; Gross et al., 2001, *Immunity* 15(2):289-302). The phenotype is similar to that caused by BAFF-R deficiency (Thompson et al., 2001, supra; Yan et al., 2001, supra). In the other hand, the knock-outs of BCMA and TACI did not lead to any severe B cell phenotypes (Xu et al., 2001, *Mol. Cell. Biol* 21:4067-4074; Von Bulow et al., 2001, *Immunity* 14:573-582). Interestingly, APRIL (also called TALL-2), the closest family member of TALL-1, does not bind to BAFF-R (Schiemann et al., 2001, supra), although it binds to BCMA and TACI with an affinity similar to sTALL-1 (Yu et al., 2000, supra).

In contrast to the other receptor family members that have at least three to four CRDs in their extra-cellular domains, BCMA and BAFF-R have only one CRD and TACI has two CRDs (Shu et al., 2000, supra; Gross et al., 2000, supra; Thompson et al., 2000, supra; Marsters et al., 2000, supra; Thompson et al., 2001, supra). Nevertheless, the overall binding affinities of sTALL-1 with BCMA and TACI (0.1 nM-1 nM) are similar to those of other family members (Yu et al., 2000, supra). Furthermore, as predicted from sequence alignment, the CRDs in BCMA and TACI contain A1 and C2 modules (Gross et al., (2000) *Nature,* 404:995-999), which were two of multiple defined structural motifs that characterize extracellular domains of TNF receptors (Naismith et al., 1998, *TRENDS Biochem. Sci.* 23:74-79). The C2 module was also found in TNF-R1 and Fn14 (Bodmer et al., (2002) *J Biol. Chem.,* 275:20632-20637), however the C2 in TNF-R1 is not involved in ligand binding (Naismith et al., 1998, supra). The only CRD in BAFF-R that was predicted to be the C2 module initially (Thompson et al., 2001, supra; Yan et al., 2001, supra) has been termed an unknown module X2 recently (Bodmer et al., 2002, supra). It is likely that there are novel interactions among these unique ligand-receptor couples accounting for their high affinity (Liu et al., 2002, *Cell* 108:383-394; Bodmer et al., 2002, supra). Therefore, to begin to understand the structure and function relationship of TALL-1 and its receptors, and to take advantage of this information to design valuable therapeutic tools, it is necessary to determine the crystal structure of sTALL-1 and its receptors.

SUMMARY OF THE INVENTION

One embodiment of the invention relates to a TALL-1 antagonist protein, wherein the protein comprises an amino acid sequence that differs from SEQ ID NO:2, or from an amino acid sequence consisting of positions 134 to 285 of SEQ ID NO:2, by at least one modification in the region connecting β strands D and E that reduces the biological activity of the TALL-1 antagonist as compared to wild-type TALL-1. In one aspect, the protein comprises an amino acid sequence that differs from SEQ ID NO:2, or from an amino acid sequence consisting of positions 134 to 285 of SEQ ID NO:2, by a modification in at least one amino acid residue selected from Val217, His218, Val219, Phe220, Gly221, Asp222, Glu223, and Leu224. In one aspect, the TALL-1 antagonist protein comprises an amino acid sequence that differs from SEQ ID NO:2, or from an amino acid sequence consisting of positions 134 to 285 of SEQ ID NO:2, by a modification of at least two amino acid residues selected from Val217, His218, Val219, Phe220, Gly221, Asp222, Glu223, and Leu224. In another aspect, the TALL-1 antagonist protein comprises an amino acid sequence that differs from SEQ ID NO:2, or from an amino acid sequence consisting of positions 134 to 285 of SEQ ID NO:2, by a modification of at least between about 3 and 8 amino acid residues selected from Val217, His218, Val219, Phe220, Gly221, Asp222, Glu223, and Leu224. In yet another aspect, TALL-1 antagonist protein comprises an amino acid sequence that differs from SEQ ID NO:2, or from an amino acid sequence consisting of positions 134 to 285 of SEQ ID NO:2, by at least a deletion of the following amino acid residues: Val217, His218, Val219, Phe220, Gly221, Asp222, Glu223, and Leu224; in one aspect of this embodiment, the TALL-1 antagonist protein further comprises a substitution of at least one non-natural amino acid residue for the deleted residues.

In one aspect, the above-described TALL-1 antagonist protein has a reduced ability to form a trimer with other TALL-1 monomers. In another aspect, the protein, when in a trimer with two other TALL-1 monomers, reduces the ability of the trimer to interact with other TALL-1 trimers. The two other TALL-1 monomers can be selected from: a wild-type TALL-1 monomer and a TALL-1 antagonist protein, as well as mixtures thereof.

In one aspect, the above-identified TALL-1 antagonist protein binds to a TALL-1 receptor selected from BCMA, BAFF-R and TACI. In one embodiment, the TALL-1 antagonist comprises an amino acid sequence that differs from SEQ ID NO:2, or from an amino acid sequence consisting of positions 134 to 285 of SEQ ID NO:2, by at least one additional modification that increases the binding affinity between the TALL-1 antagonist protein and a TALL-1 receptor, as compared to the binding affinity between wild-type TALL-1 and the TALL-1 receptor. In one aspect, the TALL-1 antagonist comprises an amino acid sequence that differs from SEQ ID NO:2, or from an amino acid sequence consisting of positions 134 to 285 of SEQ ID NO:2, by an additional modification in at least one amino acid residue selected from: Tyr163, Tyr206, Leu211, Arg231, Ile233, Pro264, Arg265, Glu266, Leu200, Leu240, Asp273, Asp275, Glu238 and Asp222. In this aspect, the additional modification increases the binding affinity between the TALL-1 antagonist protein and a TALL-1 receptor, as compared to the binding affinity between wild-type TALL-1 and the TALL-1 receptor (e.g., BCMA, BAFF-R and TACI).

Another embodiment of the invention relates to a TALL-1 antagonist protein that comprises an amino acid sequence that differs from SEQ ID NO:2, or from an amino acid sequence consisting of positions 134 to 285 of SEQ ID NO:2, by at least one modification that reduces interaction between a first trimer and a second trimer. In this embodiment the first trimer comprises (a) a monomer of the TALL-1 antagonist protein; and (b) two monomers selected from: wild-type TALL-1 monomers, the TALL-1 antagonist protein monomers, and mixtures thereof. The second trimer comprises monomers selected from wild-type TALL-1 monomers, the TALL-1 antagonist protein monomers, and mixtures thereof. In one embodiment, the TALL-1 antagonist protein comprises an amino acid sequence that differs from SEQ ID NO:2, or from an amino acid sequence consisting of positions 134 to 285 of SEQ ID NO:2, by a modification in at least one amino acid residue located in a region of TALL-1 selected from β strand C, β strand F, and the region connecting β strand D to fβ strand E. In another embodiment, the protein comprises an amino acid sequence that differs from SEQ ID NO:2, or from an amino acid sequence consisting of positions 134 to 285 of SEQ ID NO:2, by a modification in at least one amino acid residue selected from: Ile150, Leu169, Phe172, Tyr192, Lys216, Val217, His218, Val219, Phe220, Gly221, Asp222, Glu223, Leu224, Val227, Leu229, Ile250, Lys252, and Glu254. In another embodiment, the protein comprises an amino acid sequence that differs from SEQ ID NO:2, or from an amino acid sequence consisting of positions 134 to 285 of SEQ ID NO:2, by a modification in at least one amino acid residue selected from: Val217, His218, Val219, Phe220, Gly221, Asp222, Glu223, and Leu224. In another embodiment, protein comprises an amino acid sequence that differs from SEQ ID NO:2, or from an amino acid sequence consisting of positions 134 to 285 of SEQ ID NO:2, by a modification in at least one amino acid residue selected from: Tyr192, Lys252, Glu254, His218, Lys216, Glu223, Leu224, Val227, Leu229, Val219, Ile150, Leu169, Phe220, Tyr192, Ile250 and Phe172. In another embodiment, the protein comprises an amino acid sequence that differs from SEQ ID NO:2, or from an amino acid sequence consisting of positions 134 to 285 of SEQ ID NO:2, by a modification in at least one amino acid residue selected from: Tyr192, Lys252, Glu254, and His218. In yet another embodiment, protein comprises an amino acid sequence that differs from SEQ ID NO:2, or from an amino acid sequence consisting of positions 134 to 285 of SEQ ID NO:2, by a modification in at least one amino acid residue selected from: Lys216, Glu223, Leu224, Val227, and Leu229. In another embodiment, protein comprises an amino acid sequence that differs from SEQ ID NO:2, or from an amino acid sequence consisting of positions 134 to 285 of SEQ ID NO:2, by a modification in at least one amino acid residue selected from: Val219, Ile150, Leu169, Phe220, Tyr192, Ile250 and Phe172.

Preferably, the TALL-1 antagonist protein binds to a TALL-1 receptor selected from BCMA, BAFF-R and TACI. In one aspect, the TALL-1 antagonist comprises an amino acid sequence that differs from SEQ ID NO:2, or from an amino acid sequence consisting of positions 134 to 285 of SEQ ID NO:2, by at least one additional modification that increases the binding affinity between the TALL-1 antagonist protein and a TALL-1 receptor, as compared to the binding affinity between wild-type TALL-1 and the TALL-1 receptor. In one aspect, the TALL-1 antagonist comprises an amino acid sequence that differs from SEQ ID NO:2, or from an amino acid sequence consisting of positions 134 to 285 of SEQ ID NO:2, by an additional modification in at least one amino acid residue selected from: Tyr163, Tyr206, Leu211, Arg231, Ile233, Pro264, Arg265, Glu266, Leu200, Leu240, Asp273, Asp275, Glu238 and Asp222, wherein the additional modification increases the binding affinity between the TALL-1 antagonist protein and a TALL-1 receptor, as compared to the binding affinity between wild-type TALL-1 and the TALL-1 receptor (e.g., BCMA, BAFF-R and TACI).

In one embodiment, the above-described TALL-1 antagonist protein has a reduced ability to form a trimer with other TALL-1 monomers.

Yet another embodiment of the present invention relates to a TALL-1 antagonist protein that comprises an amino acid sequence that differs from SEQ ID NO:2, or from an amino acid sequence consisting of positions 134 to 285 of SEQ ID NO:2, by a modification of at least one amino acid residue selected from: Phe194, Tyr196, Tyr246, Leu282, Gln144 and Leu285. In one aspect, the protein has a reduced ability to form a trimer with other TALL-1 monomers. In another aspect, the TALL-1 antagonist protein binds to a TALL-1 receptor selected from BCMA, BAFF-R and TACI. In one embodiment, the TALL-1 antagonist comprises an amino acid sequence that differs from SEQ ID NO:2, or from an amino acid sequence consisting of positions 134 to 285 of SEQ ID NO:2, by at least one additional modification that increases the binding affinity between the TALL-1 antagonist protein and a TALL-1 receptor, as compared to the binding affinity between wild-type TALL-1 and the TALL-1 receptor. In another embodiment, the TALL-1 antagonist comprises an amino acid sequence that differs from SEQ ID NO:2, or from an amino acid sequence consisting of positions 134 to 285 of SEQ ID NO:2, by an additional modification in at least one amino acid residue selected from: Tyr163, Tyr206, Leu211, Arg231, Ile233, Pro264, Arg265, Glu266, Leu200, Leu240, Asp273, Asp275, Glu238 and Asp222, wherein the additional modification increases the binding affinity between the TALL-1 antagonist protein and a TALL-1 receptor, as compared to the binding affinity between wild-type TALL-1 and the TALL-1 receptor (e.g., BCMA, BAFF-R and TACI.

Yet another embodiment of the present invention relates to a TALL-1 antagonist protein, wherein the TALL-1 antagonist protein comprises an amino acid sequence that differs from SEQ ID NO:2, or from an amino acid sequence consisting of positions 134 to 285 of SEQ ID NO:2, by a modification of at least one amino acid residue that reduces the biological activity of the antagonist protein as compared to a wild-type TALL-1, wherein the amino acid residue is selected from: Gln144, Ile150, Leu169, Phe172, Tyr192, Phe194, Tyr196, Lys216, Val217, His218, Val219, Phe220, Gly221, Asp222, Glu223, Leu224, Val227, Leu229, Tyr246, Ile250, Lys252, Glu254, Leu282, and Leu285. The amino acid sequence of the TALL-1 antagonist further differs from SEQ ID NO:2, or from an amino acid sequence consisting of positions 134 to 285 of SEQ ID NO:2, by a modification of at least one amino acid residue that increases the binding affinity between the TALL-1 antagonist protein and a TALL-1 receptor, as compared to the binding affinity between wild-type TALL-1 and the TALL-1 receptor, wherein the amino acid residue is selected from: Tyr163, Tyr206, Leu211, Arg231, Ile233, Pro264, Arg265, Glu266, Leu200, Leu240, Asp273, Asp275, Glu238 and Asp222.

Yet another embodiment of the present invention relates to a TALL-1 antagonist protein, wherein the protein comprises an amino acid sequence that differs from SEQ ID NO:2, or from an amino acid sequence consisting of positions 134 to 285 of SEQ ID NO:2, by a modification to at least one amino acid residue selected from: Tyr163, Tyr206, Leu211, Arg231, Ile233, Pro264, Arg265, Glu266, Leu200, Leu240, Asp273, Asp275, Glu238 and Asp222, wherein the TALL-1 antagonist protein has reduced binding to a receptor for TALL-1 as compared to wild-type TALL-1. In one aspect, the protein comprises an amino acid sequence that differs from SEQ ID NO:2, or from an amino acid sequence consisting of positions 134 to 285 of SEQ ID NO:2, by a modification to at least one amino acid residue selected from: Tyr163, Leu211, Ile233, Pro264, and Leu200. In another aspect, the protein comprises an amino acid sequence that differs from SEQ ID NO:2, or from an amino acid sequence consisting of positions 134 to 285 of SEQ ID NO:2, by a modification to at least one amino acid residue selected from: Tyr206 and Leu240. In another aspect, the protein comprises an amino acid sequence that differs from SEQ ID NO:2, or from an amino acid sequence consisting of positions 134 to 285 of SEQ ID NO:2, by a modification to at least one amino acid residue selected from: Arg265, Glu266 and Glu238. In another aspect, the protein comprises an amino acid sequence that differs from SEQ ID NO:2, or from an amino acid sequence consisting of positions 134 to 285 of SEQ ID NO:2, by a modification to at least one amino acid residue selected from: Asp222, Asp 273 and Asp275. In another aspect, the TALL-1 receptor is selected from BCMA, BAFF-R, and TACI.

In one embodiment, the above-identified TALL-1 antagonist protein has reduced ability to bind to at least two of BCMA, BAFF-R and TACI. In one aspect, the TALL-1 antagonist protein has reduced ability to bind to each of BCMA, BAFF-R and TACI.

Another embodiment of the invention relates to a composition comprising any of the above-identified TALL-1 antagonist proteins.

Another embodiment of the invention relates to an April agonist protein, wherein the protein comprises an amino acid sequence that differs from SEQ ID NO:4 by at least one modification that increases the binding affinity between the APRIL agonist protein and an APRIL receptor, as compared to the binding affinity between wild-type APRIL and the APRIL receptor. In one aspect, the protein comprises an amino acid sequence that differs from SEQ ID NO:4 by a modification in at least one amino acid residue selected from: Val133, Thr177, Val181, Ile197, Pro230, Leu58, Tyr96, Phe176, Arg206, and Arg265, wherein the modification increases the binding affinity between the APRIL agonist protein and an APRIL receptor, as compared to the binding affinity between wild-type APRIL and the APRIL receptor. In another aspect, the APRIL receptor is selected from BCMA and TACI. In one embodiment, the at least one modification results in binding of the APRIL to BAFF-R.

Another embodiment of the invention relates to a composition comprising any of the above-identified APRIL agonist proteins.

Another embodiment of the invention relates to a method to inhibit TALL-1 biological activity in a mammal, comprising administering to the mammal any of the above-identified TALL-1 antagonist or APRIL agonist proteins. In one aspect, the protein is a competitive inhibitor of wild-type TALL-1 for binding to a TALL-1 receptor. In another aspect, the mammal has, or is at risk of developing, a disease or condition associated with hyperactive B cell development or B cell hyperproliferation. In one aspect, the mammal has, or is at risk of developing, a disease or condition characterized by increased numbers of mature B-lymphocytes, splenomegaly, anti-DNA antibodies, proteinuria, or glomerulonephritis. In one aspect, the disease is systemic lupus erythematosus.

Yet another embodiment of the invention relates to a recombinant nucleic acid molecule comprising a nucleic acid sequence encoding the amino acid sequence of any one of the above-identified TALL-1 antagonist or APRIL agonist proteins, operatively linked to a transcription control sequence. Yet another embodiment of the invention relates to a method to inhibit TALL-1 biological activity in a mammal, comprising administering to the mammal any of such recombinant nucleic acid molecules, wherein the protein is expressed by a host cell in the mammal. In one embodiment, the protein associates with wild-type TALL-1 monomers expressed by the cell to produce TALL-1 trimers containing the protein with reduced TALL-1 biological activity, as compared to a trimer of wild-type TALL-1 monomers. In another aspect, the protein associates with wild-type TALL-1 monomers expressed by the cell to produce TALL-1 trimers containing the protein with reduced ability to bind to a TALL-1 receptor, as compared to a trimer of wild-type TALL-1 monomers.

Another embodiment of the present invention relates to a BCMA antagonist, wherein the receptor antagonist comprises an amino acid sequence that differs from SEQ ID NO:6 by a modification in at least one amino acid residue selected from: Tyr13, Asp15, Leu17, Leu18, His19, Ile22, Leu26, Arg27, and Pro34, wherein the BCMA antagonist has an increased binding affinity for TALL-1 as compared to wild-type BCMA. In one aspect, the amino acid residue is selected from Leu17 and Leu18. In another aspect, the amino acid residue is selected from Ile22 and Leu26. In another aspect, the amino acid residue is selected from Asp15, Arg27 and Tyr13. In another aspect, the amino acid residue is His19. In another aspect, the amino acid residue is selected from Tyr13, Leu17, Leu18 and Ile22. In another aspect, the amino acid residue is substituted with an amino acid residue selected from: Ile, Met, Phe or Tyr. In one aspect the BCMA antagonist is a soluble protein.

Yet another embodiment of the present invention relates to a BAFF-R antagonist, wherein the receptor antagonist comprises an amino acid sequence that differs from SEQ ID NO:8 by a modification in at least one amino acid residue selected from: Asp26, Leu28, Val29, Arg30, Val33, Leu37, Leu38, and Arg42, and Pro45, wherein the BAFF-R antagonist has an increased binding affinity for TALL-1 as compared to wild-type BAFF-R. In one aspect, the amino acid residue is selected from Leu28 and Val29. In another aspect, the amino acid residue is selected from Val33, Leu37, Leu38 and Pro45. In another aspect, the amino acid residue is selected from Asp26 and Arg 42. In another aspect, the amino acid residue is selected from Arg30. the amino acid residue is selected from Leu28, Val29 and Val33. In another aspect, the amino acid residue is substituted with an amino acid residue selected from: Ile, Met, Phe or Tyr. In another aspect, the BAFF-R antagonist is a soluble protein.

Another embodiment of the invention relates to a method to inhibit TALL-1 receptor biological activity in a mammal, comprising administering to the mammal any of the above-identified BCMA or BAFF-R antagonists. In one aspect, the antagonist is a competitive inhibitor of a wild-type TALL-1 receptor for binding to TALL-1.

Yet another embodiment of the invention relates to a method to inhibit the biological activity of TALL-1, comprising administering to a cell that expresses TALL-1 a recombinant nucleic acid molecule comprising a nucleic acid sequence encoding APRIL, or a biologically active fragment thereof.

Another embodiment of the invention relates to an isolated BAFF-R antagonist, wherein the BAFF-R antagonist consists essentially of the amino acid sequence represented by SEQ ID NO:9, or homologues thereof with substantially the same biological activity.

Yet another embodiment of the invention relates to a method to identify a compound that is a competitive inhibitor of TALL-1 binding to its receptor. The method includes the steps of: (a) contacting a TALL-1 receptor or a TALL-1 binding fragment thereof with a homologue of a TALL-1 protein, wherein the homologue comprises an amino acid sequence with a modification in at least one amino acid residue selected from Tyr163, Tyr206, Leu21, Arg231, Ile233, Pro264, Arg265, Glu266, Leu200, Leu240, Asp273, Asp275, and Glu238; and (b) detecting whether the homologue binds to the TALL-1 receptor or fragment thereof. Homologues that bind to the TALL-1 receptor or fragment thereof potential competitive inhibitors for binding of wild-type TALL-1 to its receptor. In one aspect the method further includes a step (c) of detecting whether homologues that bind to the TALL-1 receptor or fragment thereof in (b) have a TALL-1 biological activity selected from: an ability to activate signal transduction in the TALL-1 receptor, an ability to form a trimer with two other TALL-1 monomers, an ability to form a trimer with TALL-1 two other TALL-1 monomers that is capable of interacting with other TALL-1 trimers. Homologues that have a decreased TALL-1 biological activity as compared to wild-type TALL-1 are identified as TALL-1 antagonists, and wherein homologues that have an increased TALL-1 biological activity as compared to wild-type TALL-1 are identified as TALL-1 agonists. In one aspect, step (b) further comprises comparing the binding affinity the homologue to the TALL-1 receptor or fragment of thereof to the binding affinity of wild-type TALL-1 and the TALL-1 receptor, and the method further comprises step (d) of selecting homologues which have an increased binding affinity to the TALL-1 receptor or fragment of and a decreased TALL-1 biological activity.

Yet another embodiment of the invention relates to a method of structure-based identification of compounds which potentially bind to TALL-1, comprising: (a) obtaining atomic coordinates that define the three dimensional structure of TALL-1; and (b) selecting candidate compounds for binding to the TALL-1 by performing structure based drug design with the structure of (a), wherein the step of selecting is performed in conjunction with computer modeling. The atomic coordinates are selected from: (i) atomic coordinates determined by X-ray diffraction of a crystalline TALL-1; (ii) atomic coordinates selected from: (1) atomic coordinates represented in any one of Tables 2-12; (2) atomic coordinates that define a three dimensional structure having an average root-mean-square deviation (RMSD) of equal to or less than about 1.7 Å over the backbone atoms in secondary structure elements of at least 50% of the residues in a three dimensional structure represented by the atomic coordinates of (1); and (3) atomic coordinates in any one of Tables 2-12 defining a portion of the TALL-1, wherein the portion of the TALL-1 comprises sufficient structural information to perform step (b); and/or (iii) atomic coordinates defining the three dimensional structure of TALL-1 molecules arranged in a crystalline manner in a space group $P6_322$ so as to form a unit cell having approximate dimensions of a=b=234 Å, c=217 Å.

In one aspect of the above-identified method, the method further comprises a step (c) of selecting candidate compounds of (b) that inhibit the biological activity of TALL-1. In this aspect, the step (c) of selecting can include: (i) contacting the candidate compound identified in step (b) with TALL-1; and (ii) measuring the biological activity of the TALL-1, as compared to in the absence of the candidate compound.

In another aspect of the above-identified method, the method further comprises a step (c) of selecting candidate compounds of (b) that inhibit the binding of TALL-1 to a TALL-1 receptor. In this aspect, the step (c) of selecting can include (i) contacting the candidate compound identified in step (b) with the TALL-1 or a fragment thereof and a TALL-1 receptor or TALL-1 receptor binding fragment thereof under conditions in which a TALL-1-TALL-1 receptor complex can form in the absence of the candidate compound; and (ii) measuring the binding of the TALL-1 or fragment thereof to bind to the TALL-1 receptor or fragment thereof, wherein a candidate inhibitor compound is selected when there is a decrease in the binding of the TALL-1 or fragment thereof to the TALL-1 receptor or fragment thereof, as compared to in the absence of the candidate inhibitor compound. Preferably, the TALL-1 receptor is selected from BCMA, BAFF-R and TACI.

In yet another embodiment, step (b) of selecting comprises identifying candidate compounds for binding to a receptor binding site of the TALL-1 protein, the receptor binding site comprising an amino acid residue selected from Tyr163, Tyr206, Leu211, Arg231, Ile233, Pro264, Arg265, Glu266, Leu200, Leu240, Asp273, Asp275, Glu238 and Asp222. In another embodiment, step (b) of selection comprises identifying candidate compounds for binding to the TALL-1 such that trimer-trimer interactions between trimers of TALL-1 monomers is inhibited. In this aspect, the step of selecting can include identifying candidate compounds for binding to TALL-1 at a site including an amino acid residue selected from: Gln144, Ile150, Leu169, Phe172, Tyr192, Phe194, Tyr196, Lys216, Val217, His218, Val219, Phe220, Gly221, Asp222, Glu223, Leu224, Val227, Leu229, Tyr246, Ile250, Lys252, Glu254, Leu282, and Leu285.

Another embodiment of the present invention relates to a therapeutic composition comprising a compound that inhibits the biological activity of TALL-1, the compound being identified by the method described above. Another embodiment of the present invention relates to a method to treat a disease or condition that can be regulated by modifying the biological activity of TALL-1, comprising administering to a mammal with such a disease or condition such a therapeutic composition.

Yet another embodiment of the invention relates to a method to construct a three dimensional model of TALL-1 protein or homologue thereof, comprising: (a) obtaining atomic coordinates that define the three dimensional structure of TALL-1, the atomic coordinates being selected from any of those described above; and (b) performing computer modeling with the atomic coordinates of (a) and to construct a model of a three dimensional structure of a TALL-1 or homologue thereof.

Yet another embodiment of the invention relates to a method of structure-based identification of compounds which potentially bind to a TALL-1 receptor selected from BCMA and BAFF-R, comprising (a) obtaining atomic coordinates that define the three dimensional structure of BCMA or BAFF-R; and (b) selecting candidate compounds for binding to the BCMA or BAFF-R by performing structure based drug design with the structure of (a), wherein the step of selecting is performed in conjunction with computer modeling. In this embodiment, the atomic coordinates are selected from: (i) atomic coordinates determined by X-ray diffraction of a crystalline BCMA or crystalline BAFF-R; (ii) atomic coordinates selected from: (1) atomic coordinates represented in any one of Tables 13-33; (2) atomic coordinates that define a three dimensional structure having an average root-mean-square deviation (RMSD) of equal to or less than about 1.7 Å over the backbone atoms in secondary structure elements of at least 50% of the residues in a three dimensional structure represented by the atomic coordinates of (1); (3) atomic coordinates in any one of Tables 13-22 defining a portion of the BCMA, wherein the portion of the BCMA comprises sufficient structural information to perform step (b); and (4) atomic coordinates in any one of Tables 14-33 defining a portion of the BAFF-R, wherein the portion of the BAFF-R comprises sufficient structural information to perform step (b); and (iii) atomic coordinates defining the three dimensional structure of BCMA molecules or BAFF-R molecules arranged in a crystalline manner in a space group $P6_322$ so as to form a unit cell having approximate dimensions of a=b=234 Å, c=217.

Yet another embodiment of the invention relates to a method to construct a three dimensional model of BCMA, BAFF-R, TACI, or a homologue thereof, comprising: (a) obtaining atomic coordinates that define the three dimensional structure of BCMA or BAFF-R, the atomic coordinates being selected from any of those described above for BCMA or BAFF-R; and (b) performing computer modeling with the atomic coordinates of (a) and an amino acid sequence corresponding to BCMA, BAFF-R or TACI to construct a model of a three dimensional structure of the BCMA, BAFF-R or TACI, or homologue thereof.

Another embodiment of the invention relates to a crystal comprising a TALL-1 protein, wherein the crystal effectively diffracts X-rays for the determination of the atomic coordinates of the TALL-1 protein to a resolution of greater than 3.0 Å, and $P6_322$ so as to form a unit cell having approximate dimensions of a=b=234 Å, c=217.

BRIEF DESCRIPTION OF THE FIGURES OF THE INVENTION

The patent or application file contains at least one drawing executed in color. Copies of this patent or patent application with color drawing will be provided by the Office upon request and payment of the necessary fee.

Figure 3A:
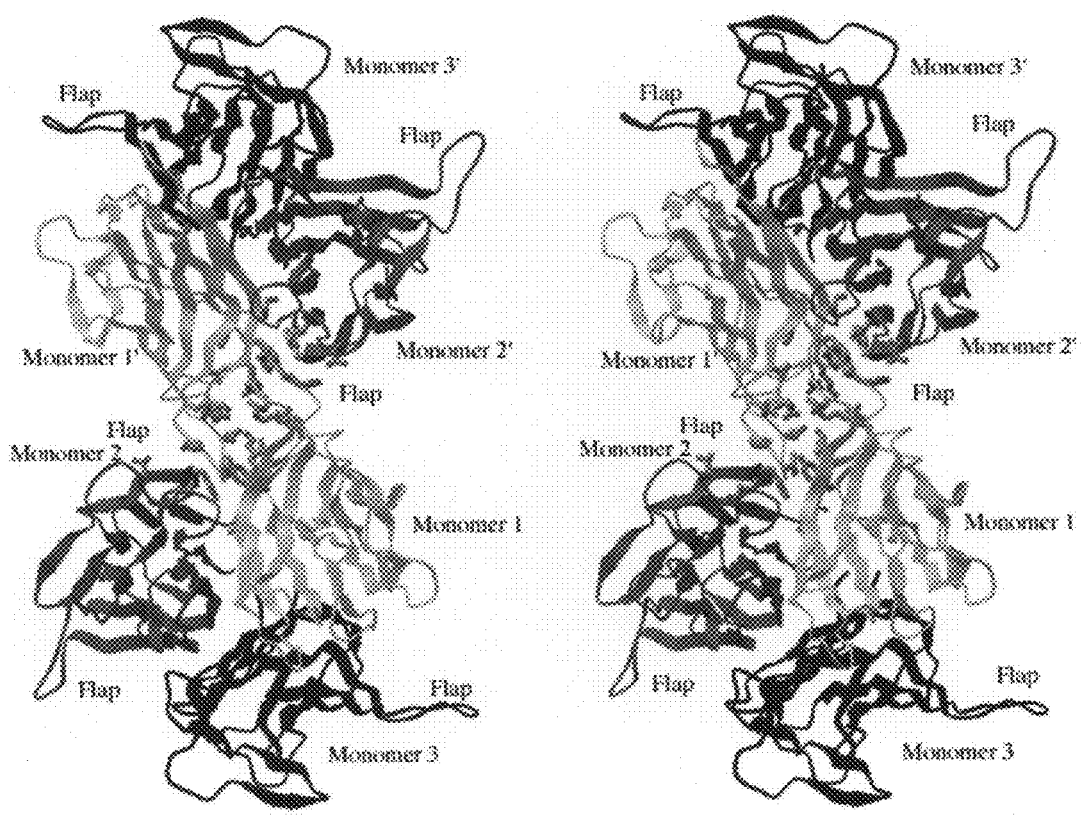

FIG. 3A is a stereo view of the interactions between two sTALL-1 trimers; rimer 1 consists of monomers 1 (light gray), 2 (gray), and 3 (dark); trimer 2 contains monomers 1', 2', and 3'.

Figure 3B:
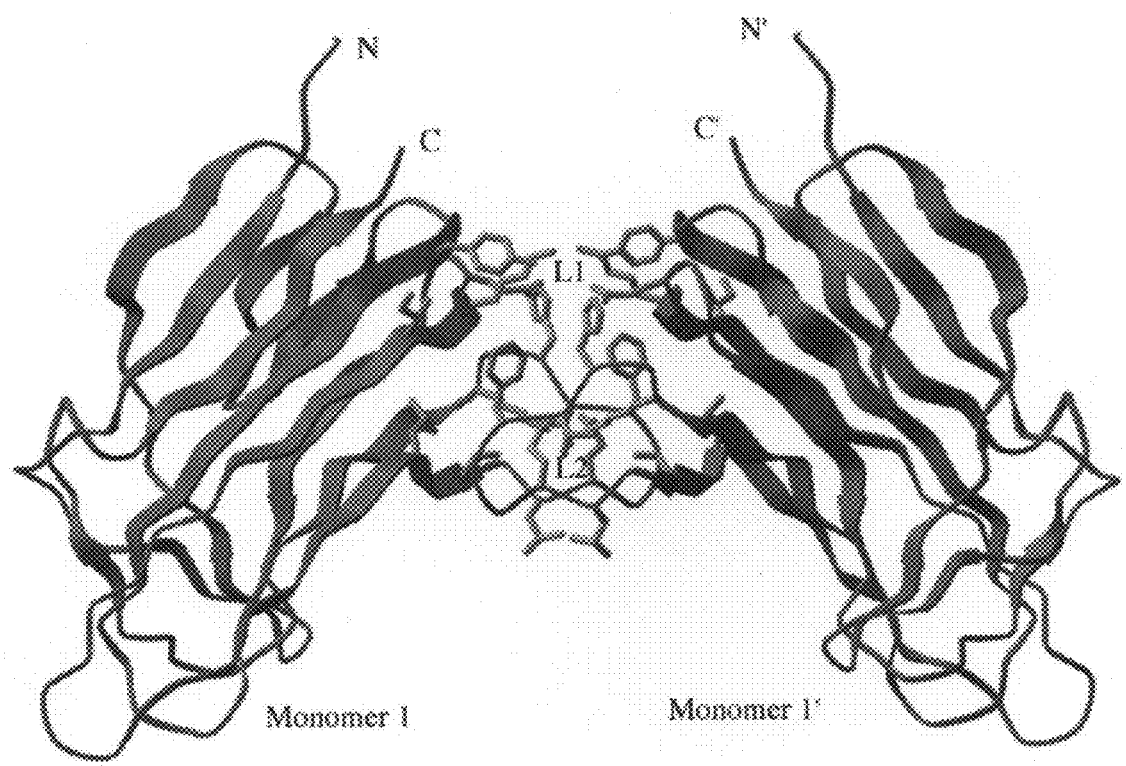

FIG. 3B shows the major interaction is involved in two monomers (monomer 1 and monomer 1'); two layered interactions are termed layer 1 (L1) and layer 2 (L2).

Figure 3C:
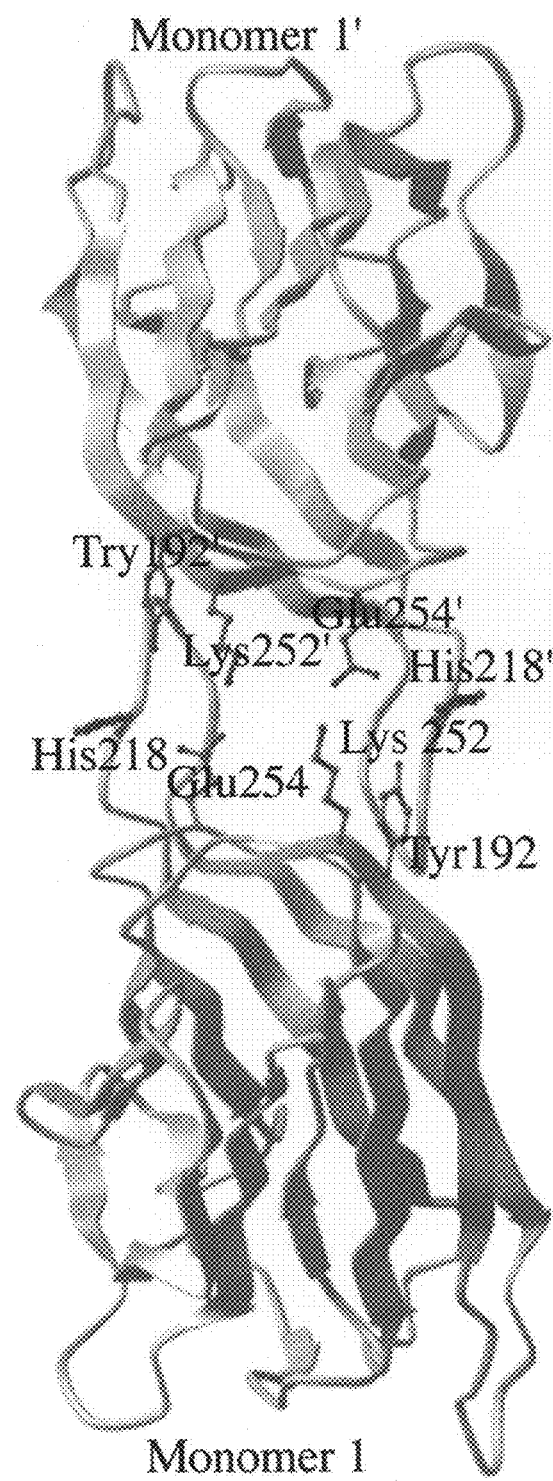

FIG. 3C shows residues and locations of layer 1.

Figure 3D:
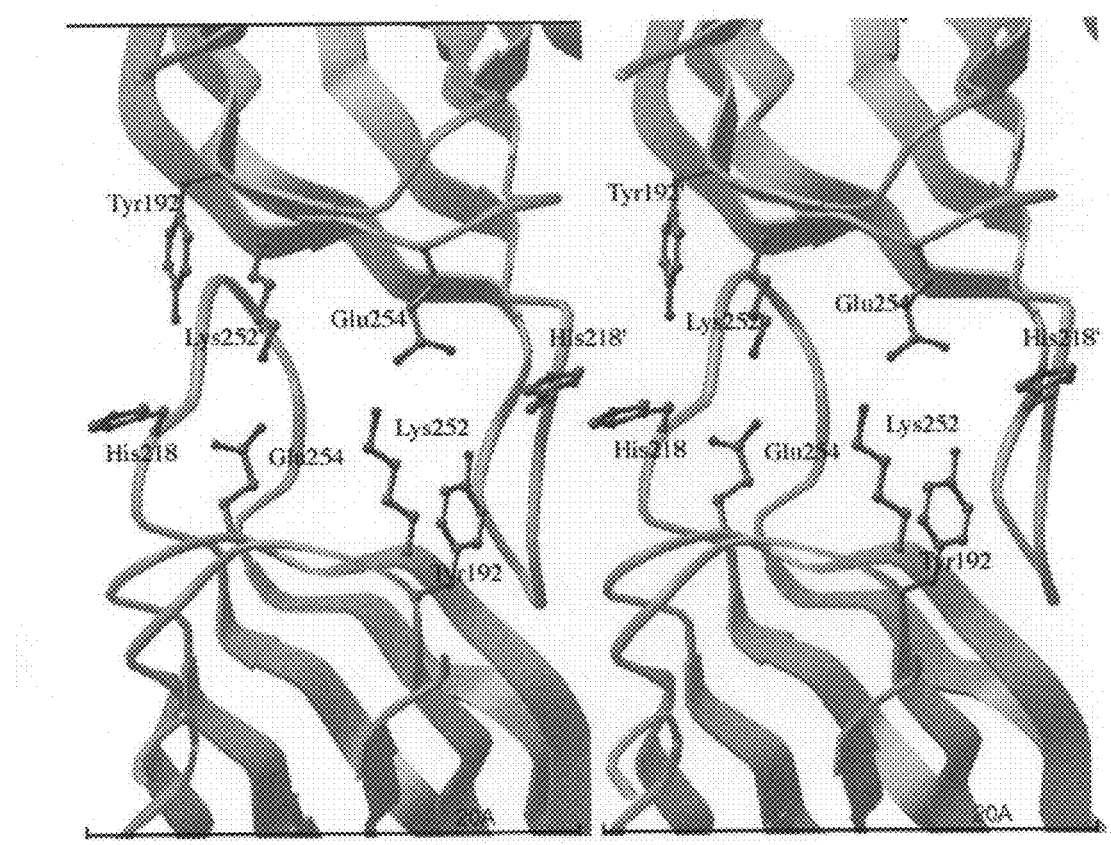

FIG. 3D is a stereo view of the interactions of layer 1.

Figure 3E:
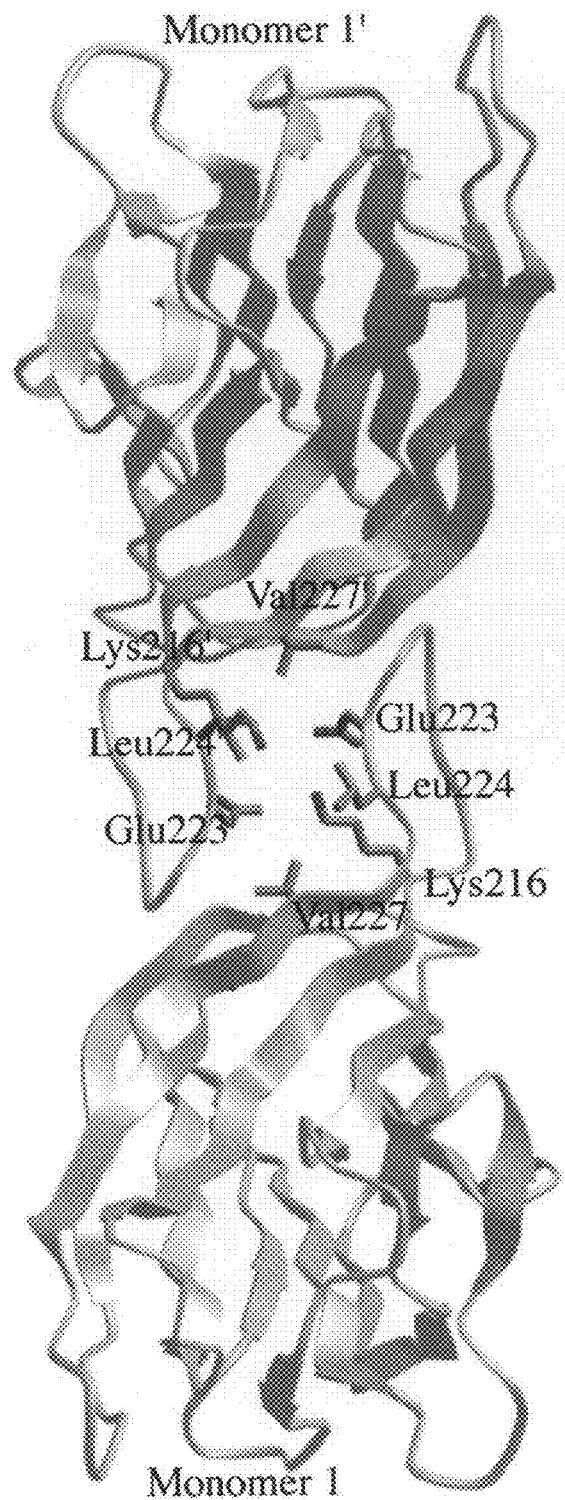

FIG. 3E shows residues and locations of layer 2.

Figure 3F:
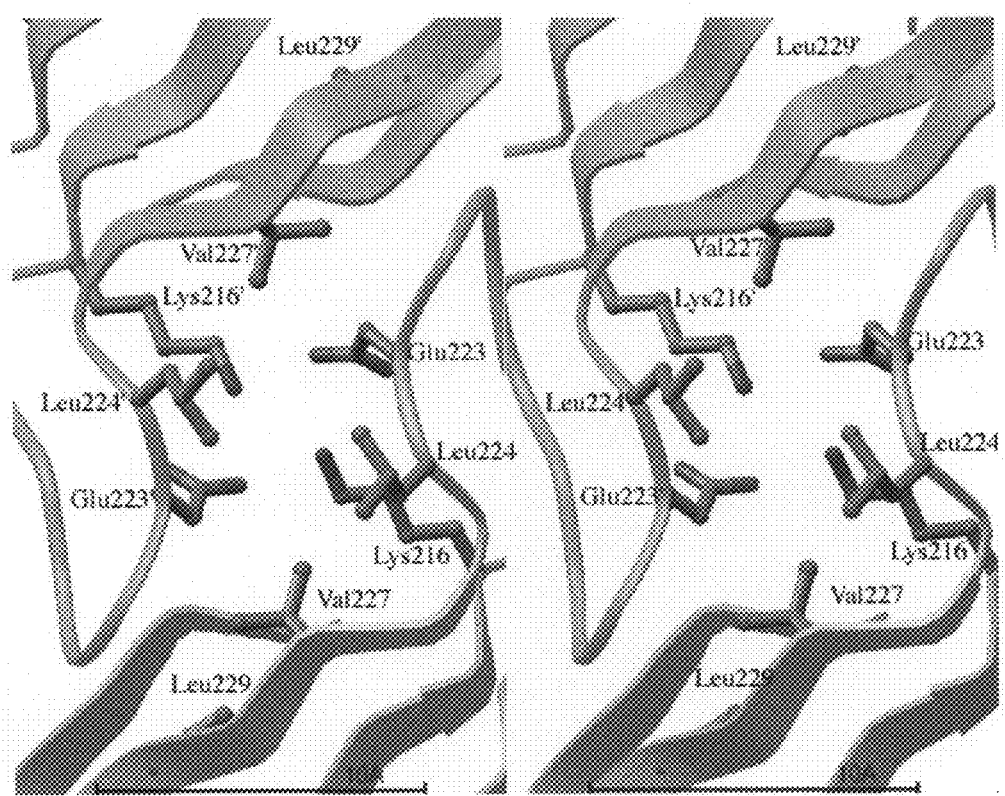

FIG. 3F is a stereo view of the interactions of layer 2.

Figure 3G:
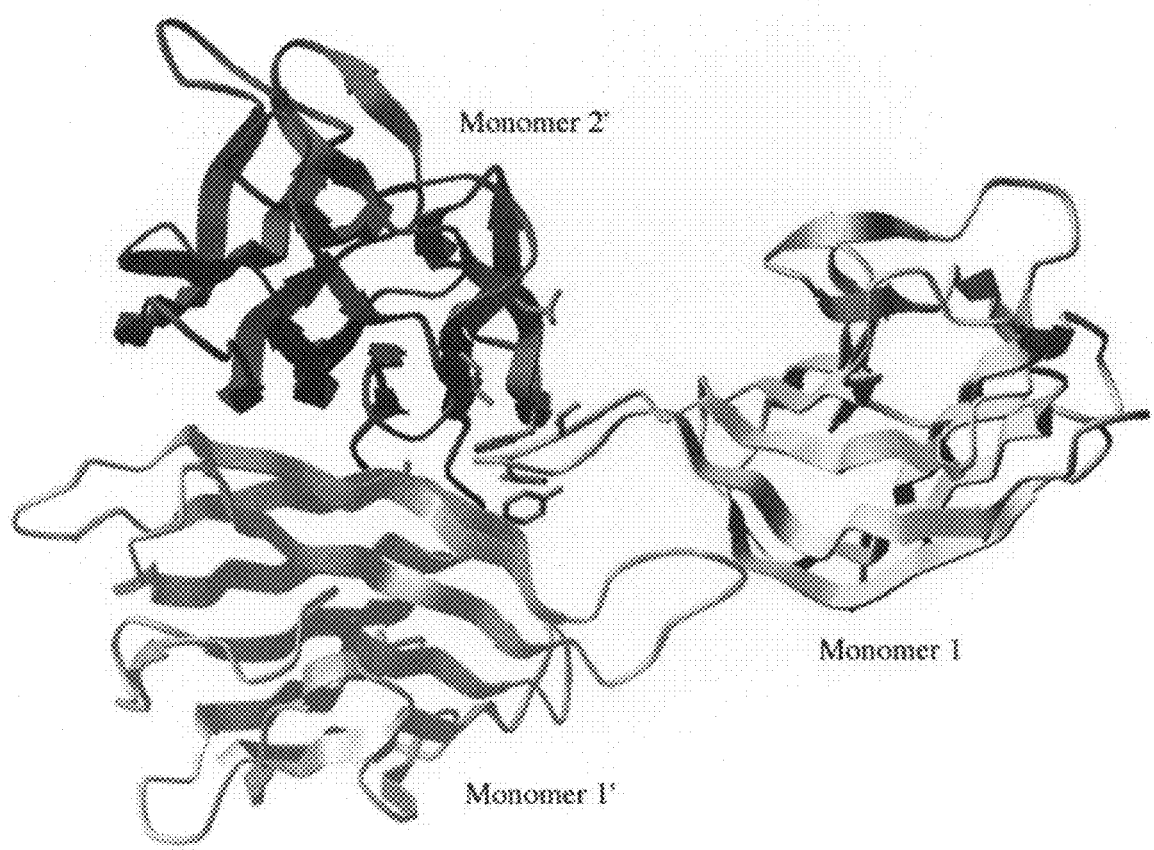

FIG. 3G shows residues and locations of the third layer interactions that involve three monomers; monomers 1 (yellow), 1' (gray), and 2' (dark).

Figure 3H:
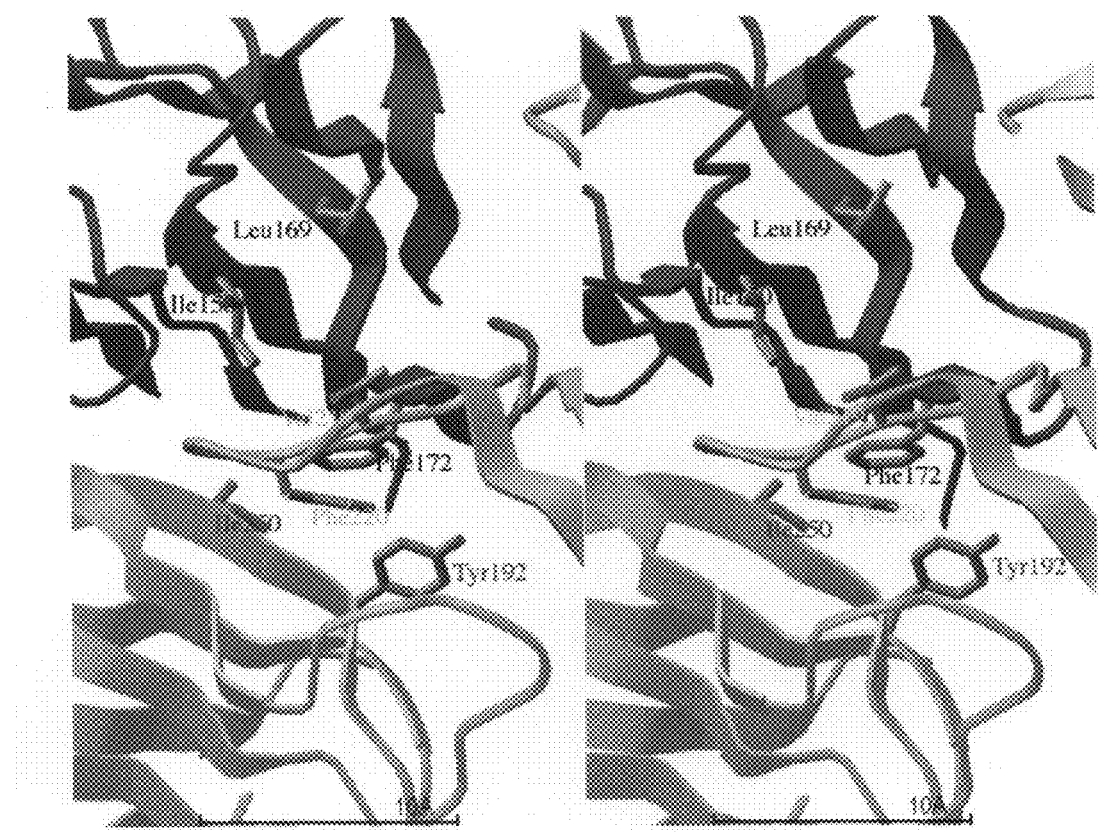

FIG. 3H is a stereo view of the two hydrophobic cores formed by residues from three monomers (residues from monomer 1 are colored red, residues from monomer 1' are colored blue, residues from monomer 2' are colored dark).

Figures 4A, 4B, 4C:
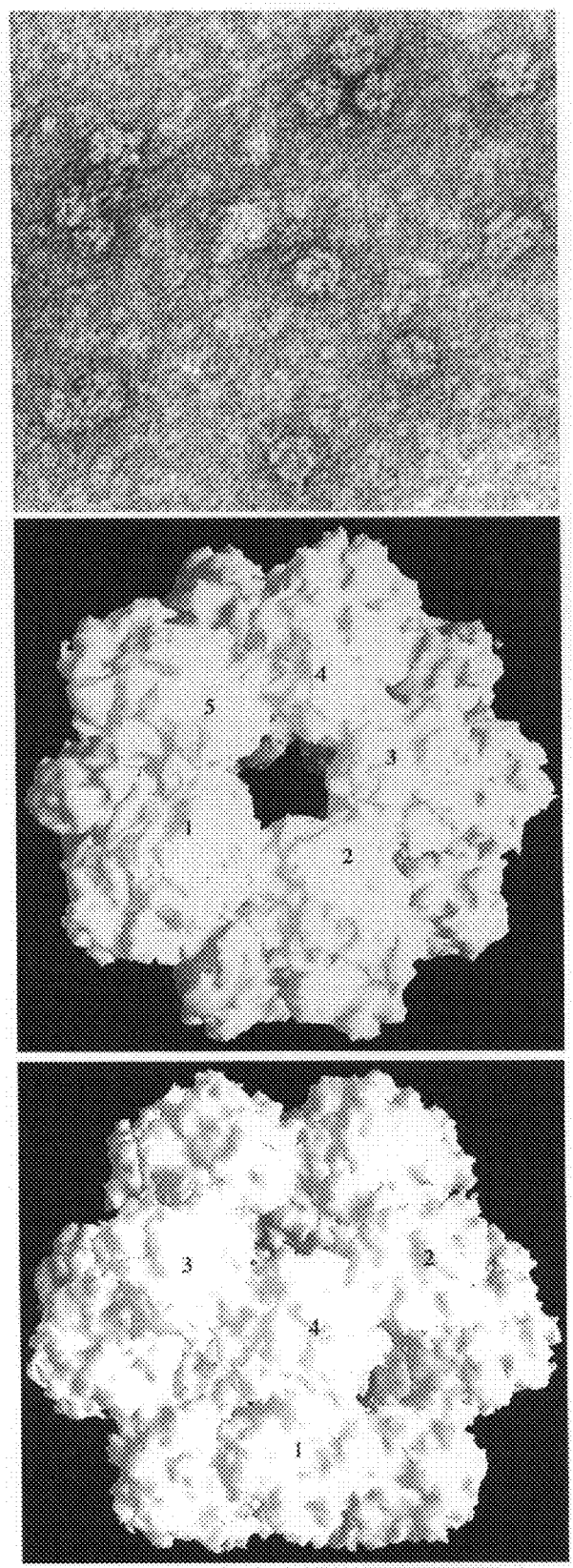

FIG. 4A shows the electron microscopy view of sTALL-1 in solution after negative staining; black bar is 50 nm long and clusters of sTALL-1 are around 20 nm in diameter.

Figures 2A, 2B, 2C:
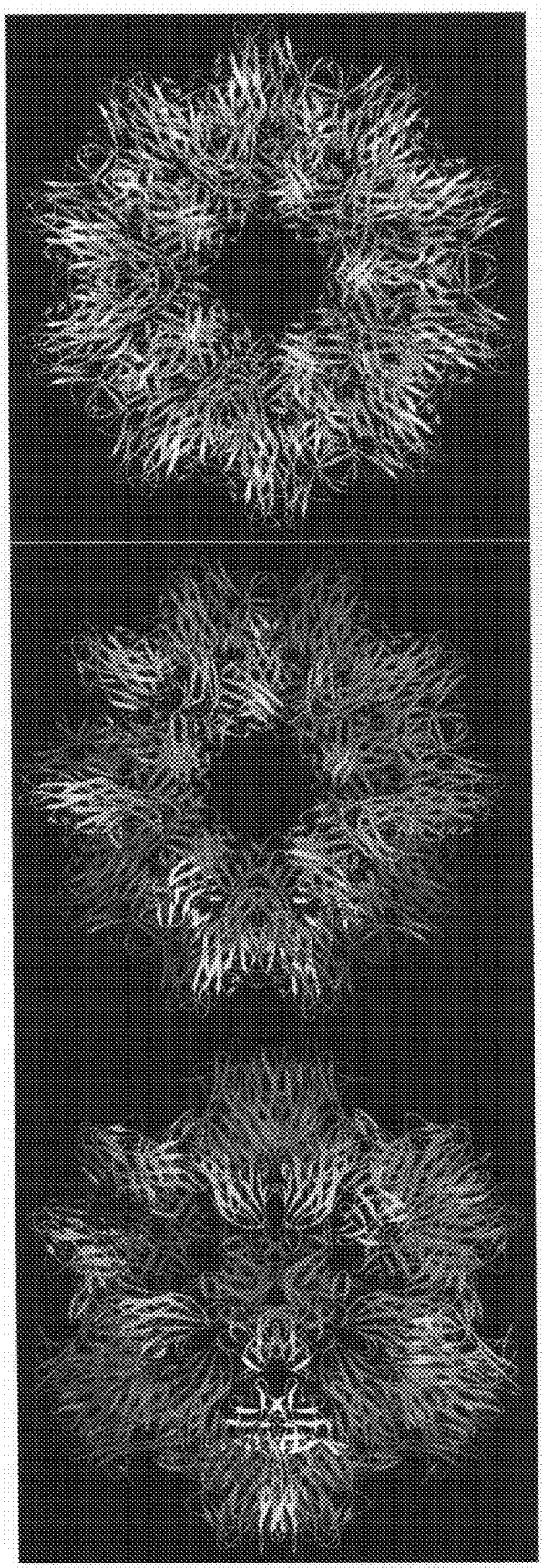
FIG. 2A is a digitized image showing the relative position of an asymmetry unit in the cluster and overall structures of the cluster at different orientations; the 10 monomers (colored yellow) in the asymmetric unit, which generate the left 50 monomers (colored gray) through crystallographic symmetry ($P6_322$) to form the virus-like cluster with total of 60 monomers.
FIG. 2B is a digitized image showing the structure of virus-like cluster (T=1) looking down from the local 5-fold symmetry.
FIG. 2C is a digitized image showing the structure of virus-like cluster looking down from the 3-fold symmetry; all monomers are colored according to chains as default set in RIBBON.

FIG. 4B is a surface presentation of sTALL-1 viewing from the similar orientation as FIG. 2B.

FIG. 4C is a surface presentation of sTALL-1 viewing from the similar orientation as FIG. 2C.

Figure 5A:
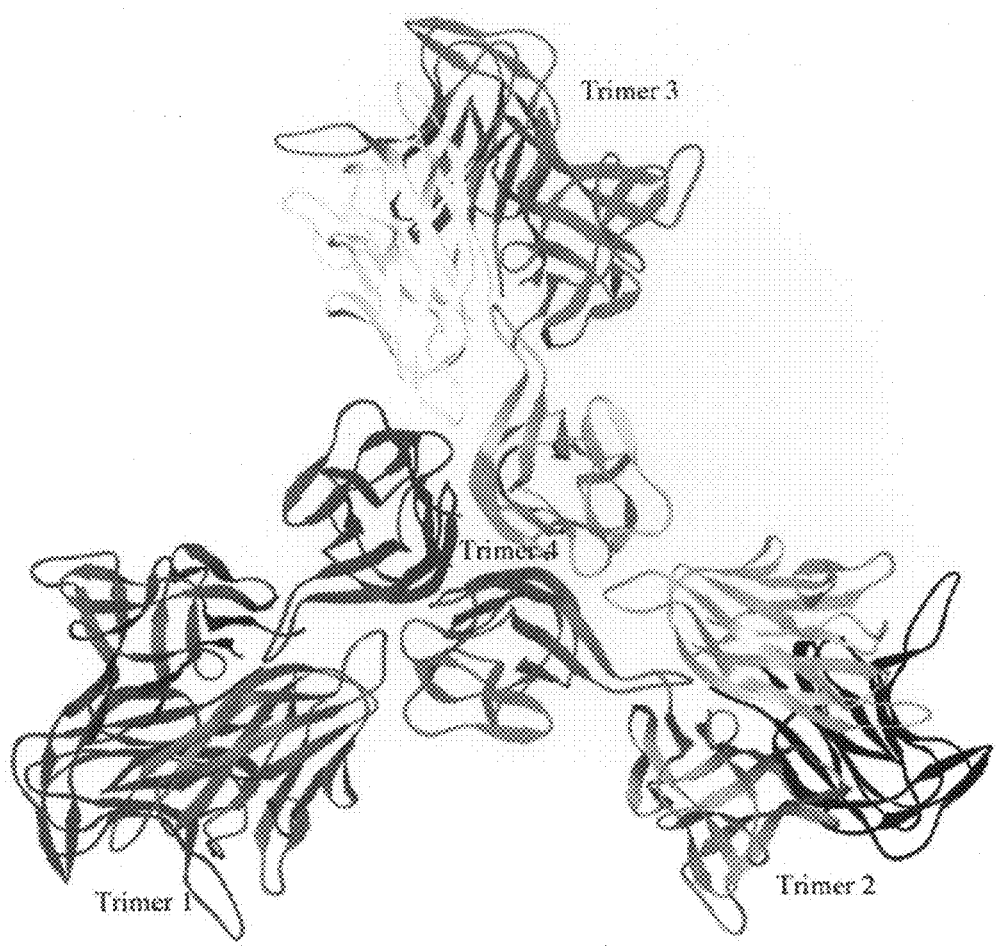

FIG. 5A shows a possible sub-cluster of four trimers (trimers 1, 2, 3, and 4) of sTALL-1 in the virus-like cluster.

Figure 5B:
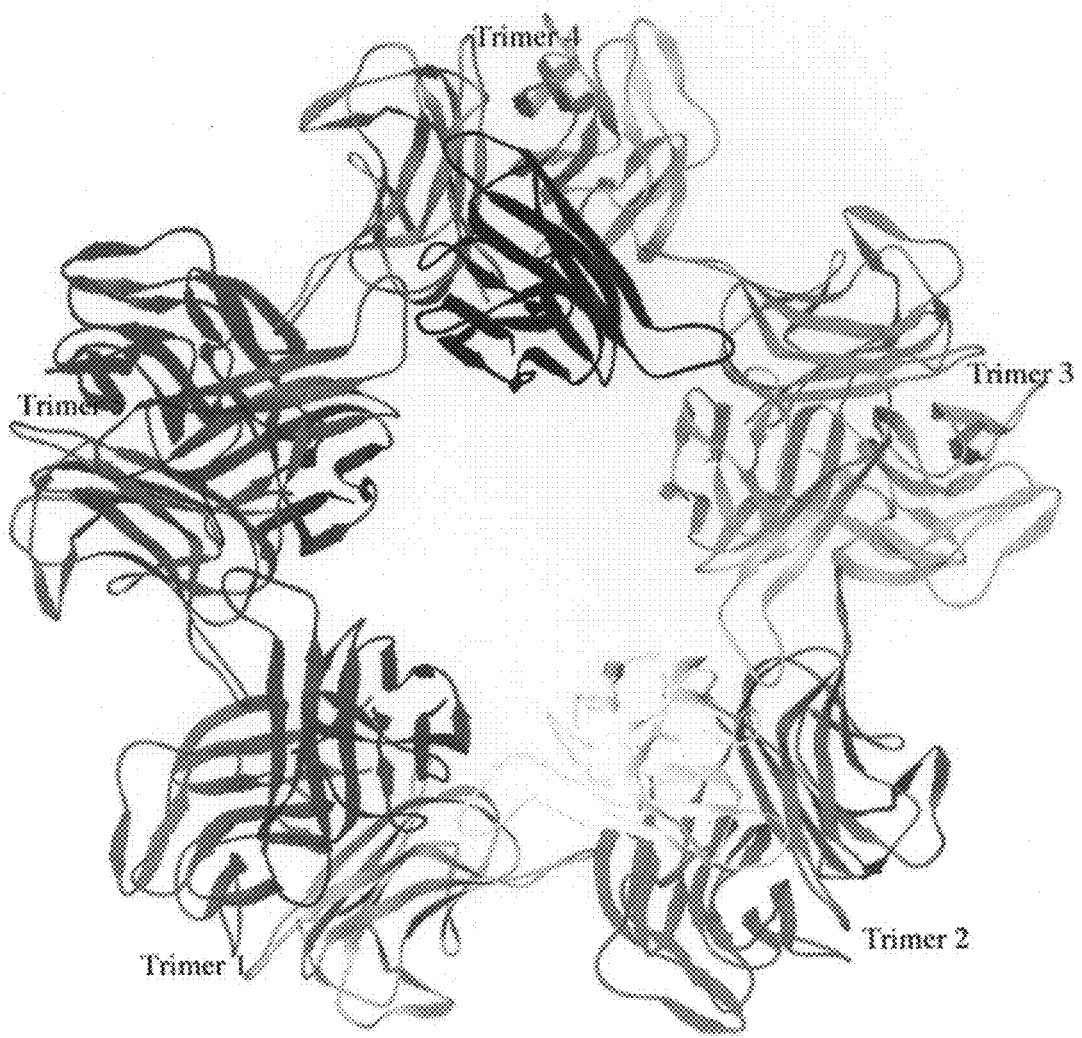

FIG. 5B shows a possible sub-cluster of five trimers (trimers 1, 2, 3, 4, and 5) of sTALL-1.

Figure 6A:
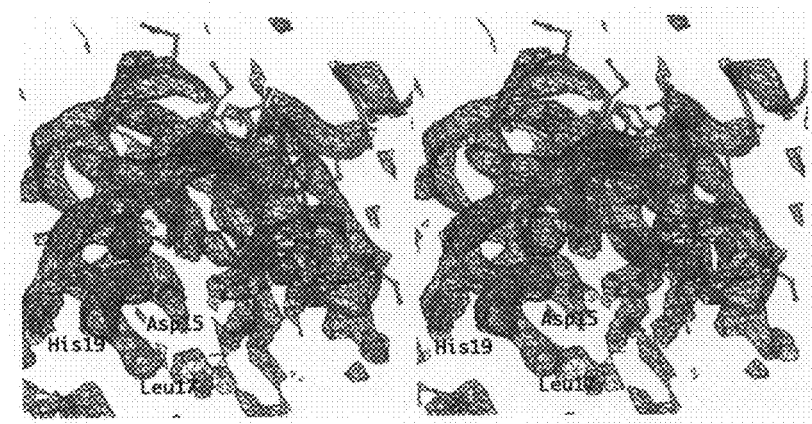

FIG. 6A is an initial Of-Fc map of eBCMA with sTALL-1 at 2a level; phases are calculated from sTALL-1 model (PDB ID, 1JH5); eBCMA is the final refined model; the map part is a representative of all eight binding receptors in the asymmetry unit, with most residues shown with their side-chains.

Figure 6B:
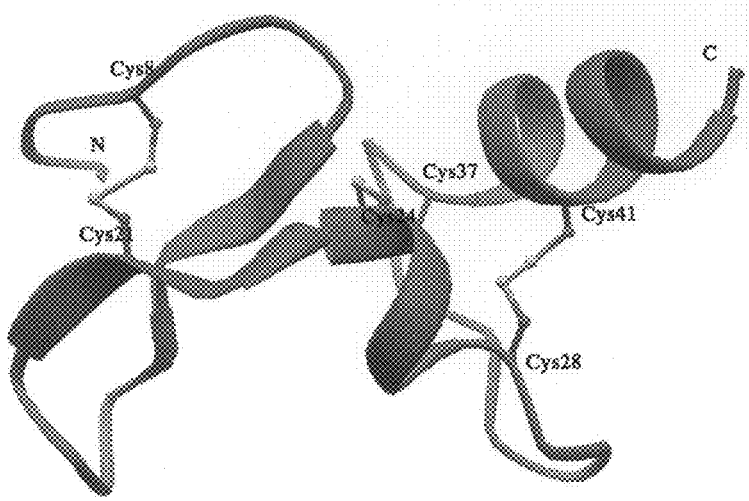

FIG. 6B is a ribbon diagram of the three-dimensional structure of eBCMA (residue 5-43 of SEQ ID NO:6); three disulfide bridges are also shown.

Figure 6C:
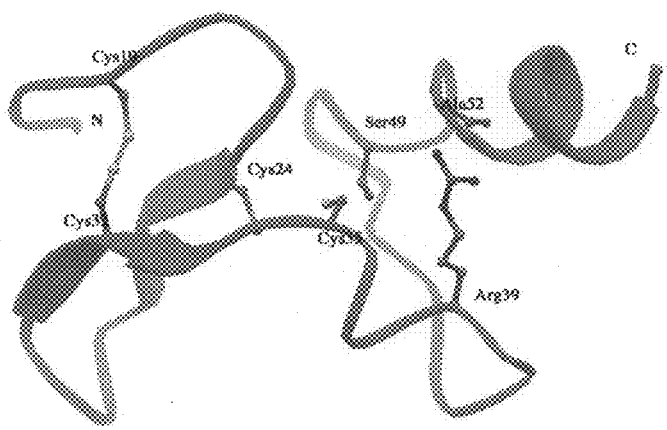

FIG. 6C is a ribbon diagram of the three-dimensional structure of eBAFF-R (residue 16-58 of SEQ ID NO:8); one disulfide bridge and two pseudo disulfide-like connections are also shown.

Figure 7A:
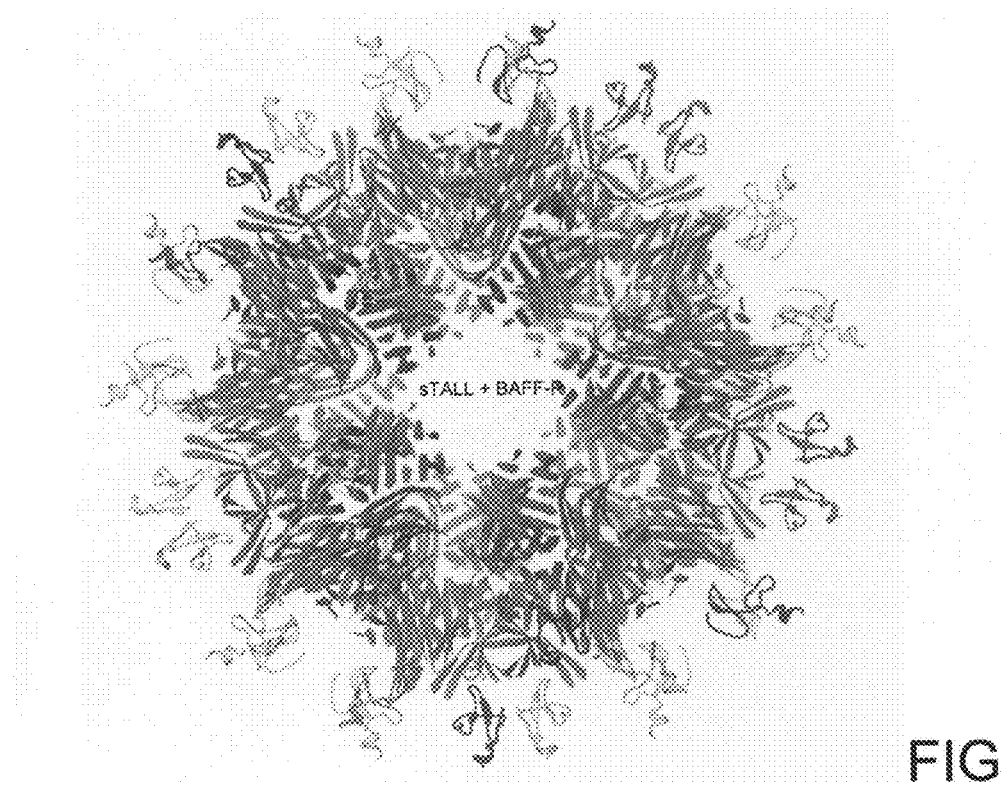

FIG. 7A shows the 60 monomers of sTALL-1 (colored green) and 60 monomers of eBAFF-R (molecules colored yellow are real from the complex structure, molecules colored blue are partially ordered, molecules colored red are missing in the complex due to crystal packing).

Figure 7B:
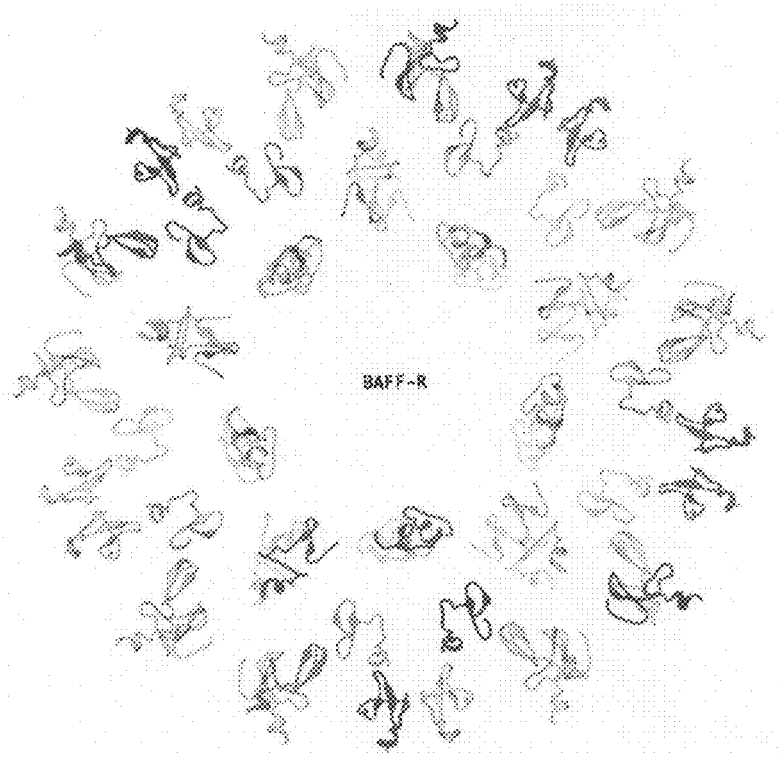

FIG. 7B shows a representation of FIG. 7A without sTALL-1.

Figure 7C:
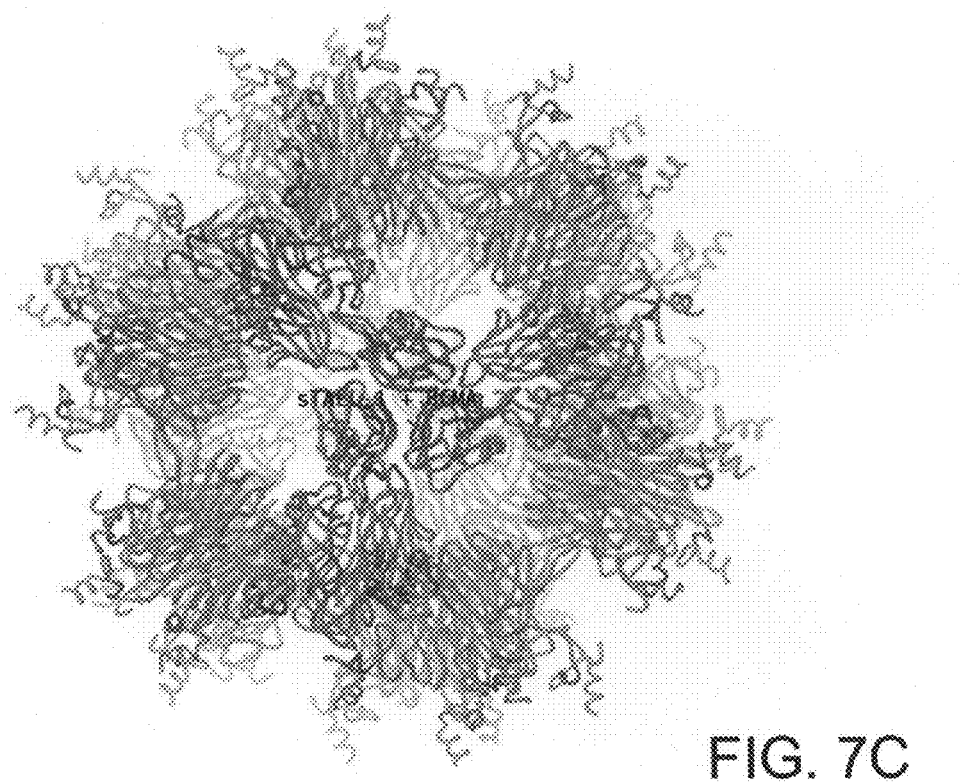

FIG. 7C shows the 60 monomers of sTALL-1 and 60 monomers of eBCMA; all are colored according to secondary structure.

Figure 7D:
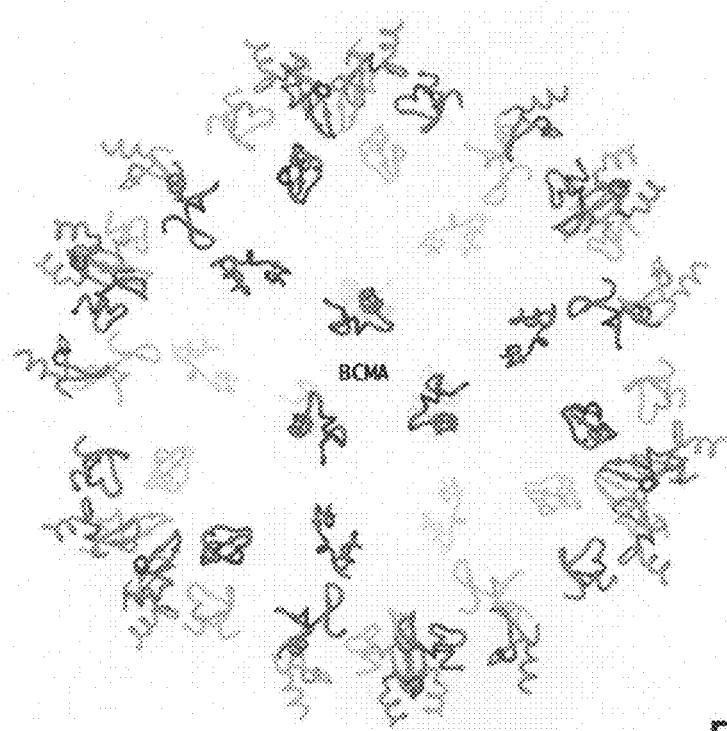

FIG. 7D shows a representation of FIG. 7C without sTALL-1.

Figures 8A, 8B:
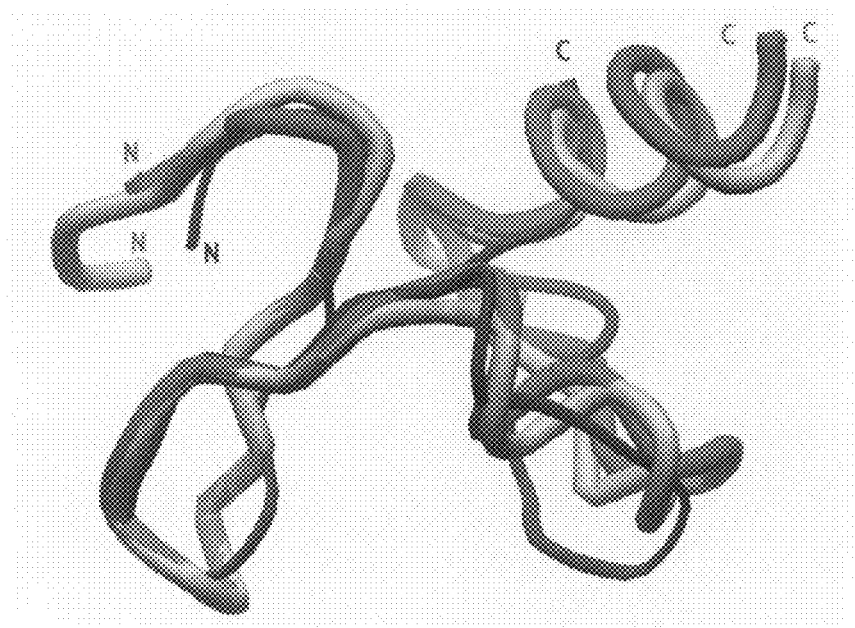

FIG. 8A shows a superposition of eBCMA, eBAFF-R, and the C2 containing CRD from TNF-R1 (Naismith et al., 1998, supra).

FIG. 8B shows a structure based sequence alignment of CRD modules of BCMA (SEQ ID NO:11), BAFF-R (SEQ ID NO:12), TACI1 (SEQ ID NO:13), TACI2 (SEQ ID NO:14), Fn14 (SEQ ID NO:15), and TNF-R1 (SEQ ID NO:16); residues colored red are conserved disulfide bridges or pseudo disulfide bridges, which builds up module A1, D2, and D0; residues colored yellow are not defined; residues colored blue are for the C2 module; residues colored green are putative residues involved in ligand recognition.

Figure 9A:
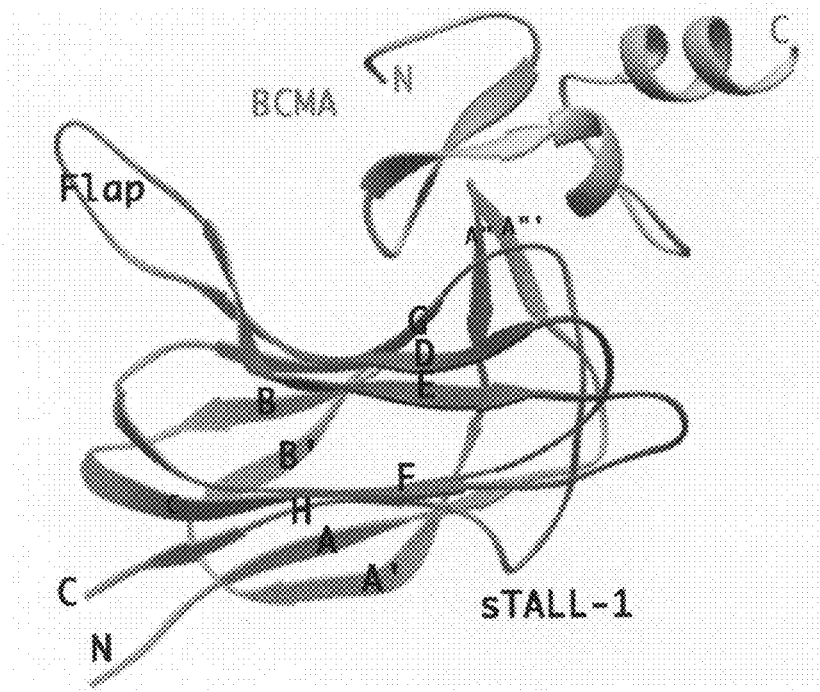

FIG. 9A shows the one to one mode interaction of eBCMA with sTALL-1.

Figure 9B:
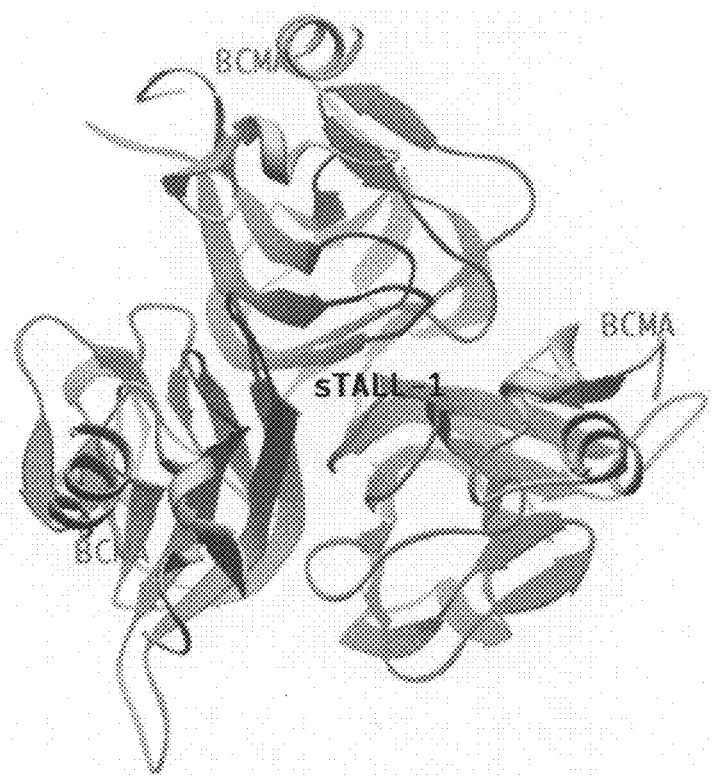

FIG. 9B shows three eBCMA on the trimer sTALL-1.

Figure 9C:
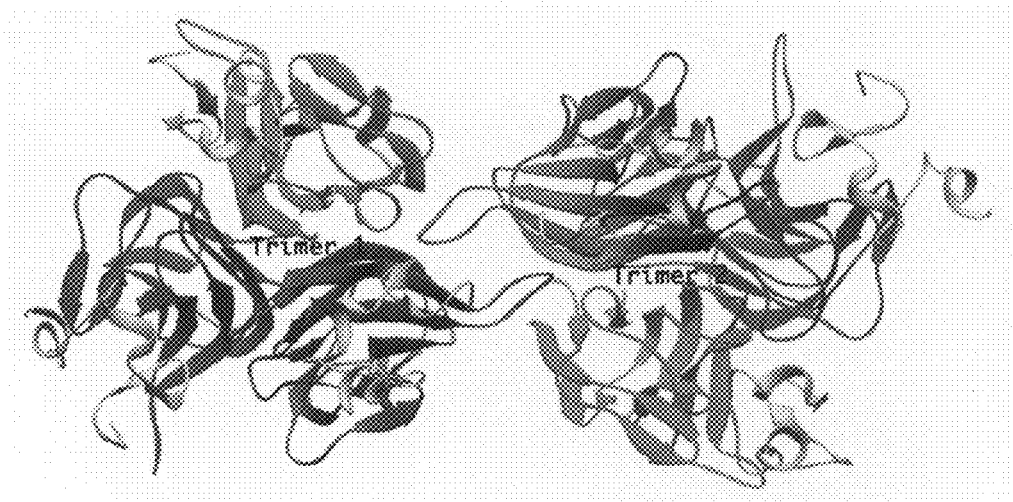

FIG. 9C shows two trimers of eBCMA and sTALL-1 complex.

Figure 9D:
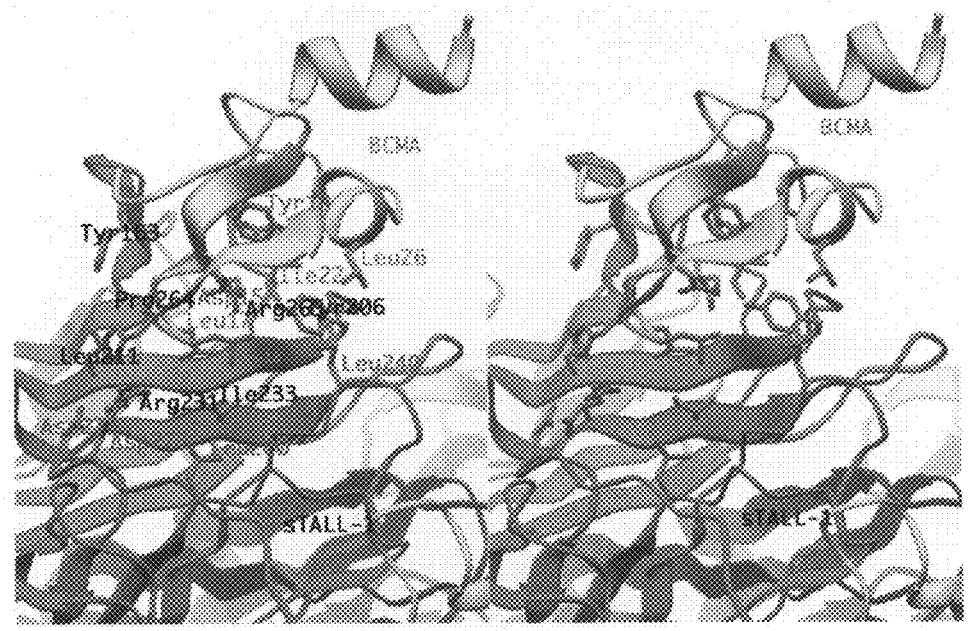

FIG. 9D shows the overall interactions between eBCMA and sTALL-1.

Figure 9E:
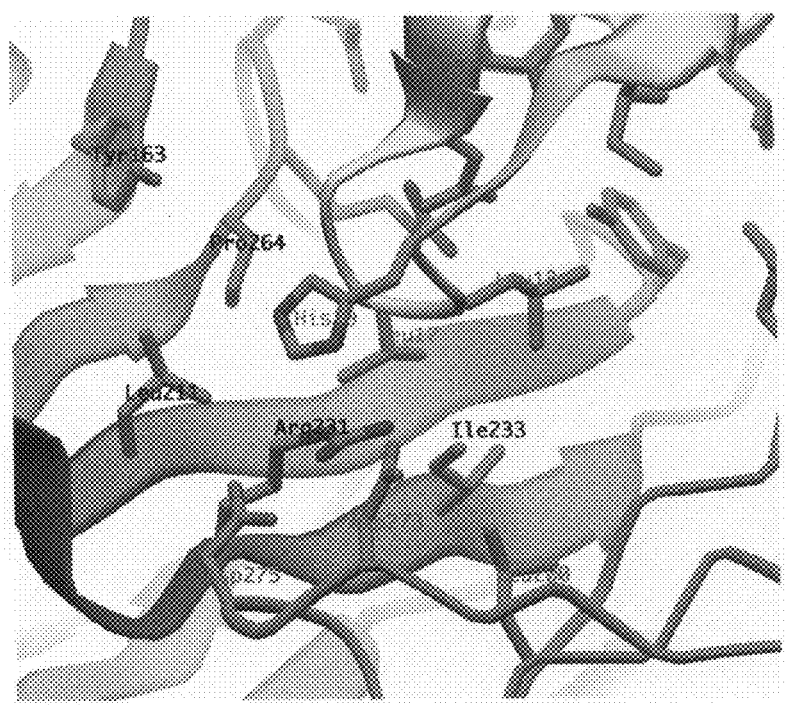

FIG. 9E shows the hydrophobic core 1 for the interaction between eBCMA and sTALL-1.

Figure 9F:
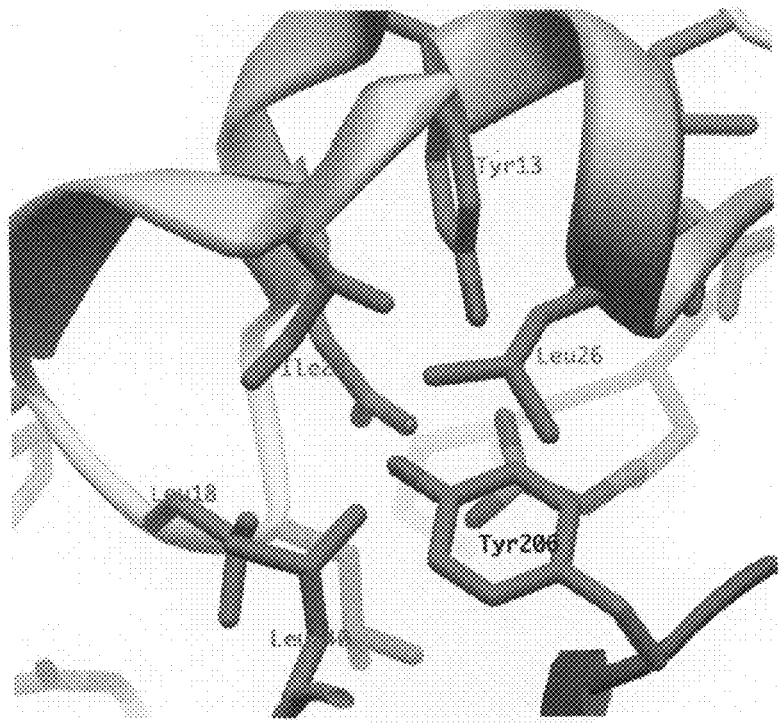

FIG. 9F shows the hydrophobic core 2 for the interaction between eBCMA and sTALL-1.

Figure 9G:
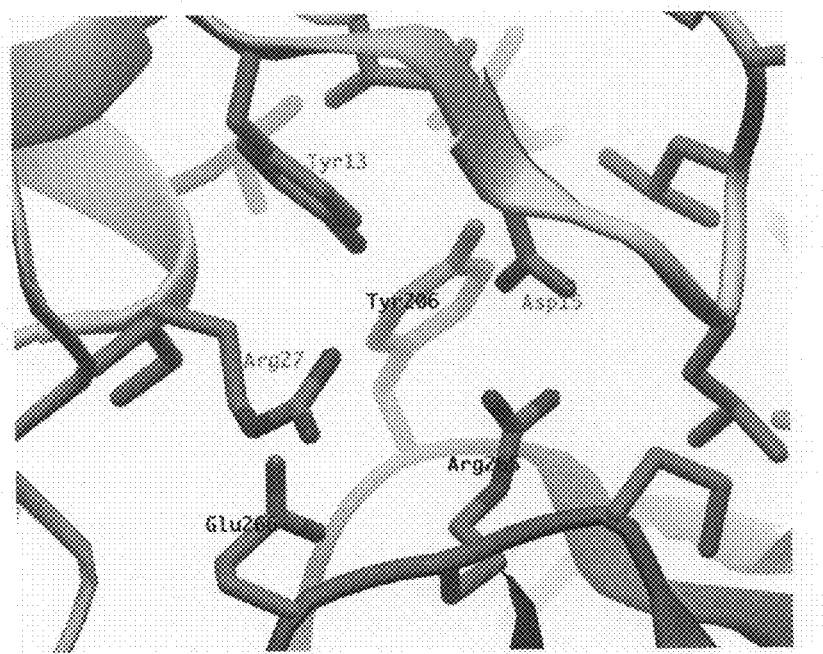

FIG. 9G shows salt bridges 1 and 2 for the interaction between eBCMA and sTALL-1.

Figure 9H:
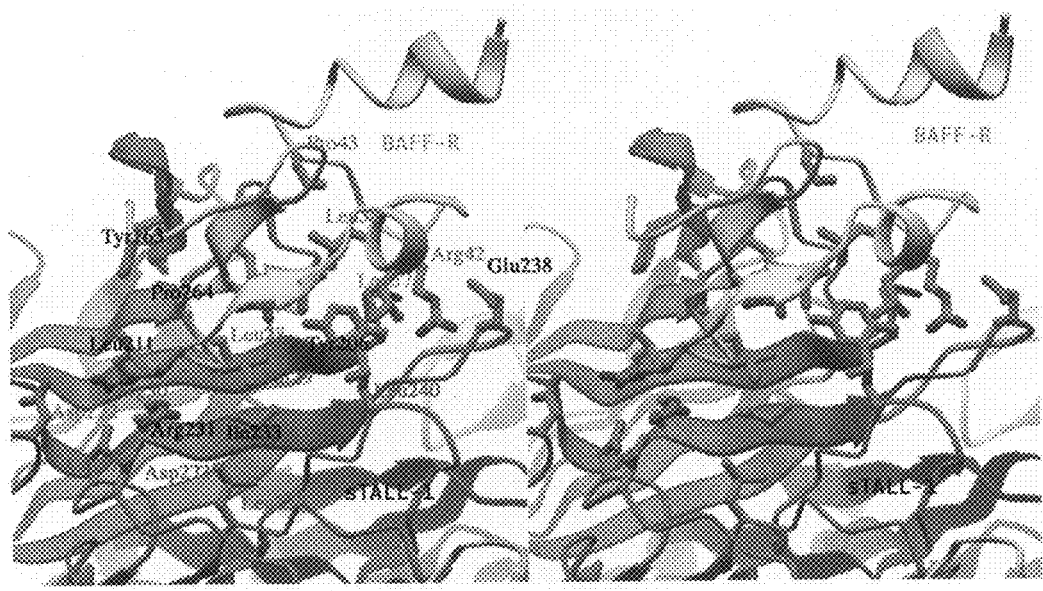

FIG. 9H shows the overall interactions between eBAFF-R and sTALL-1.

Figure 9I:
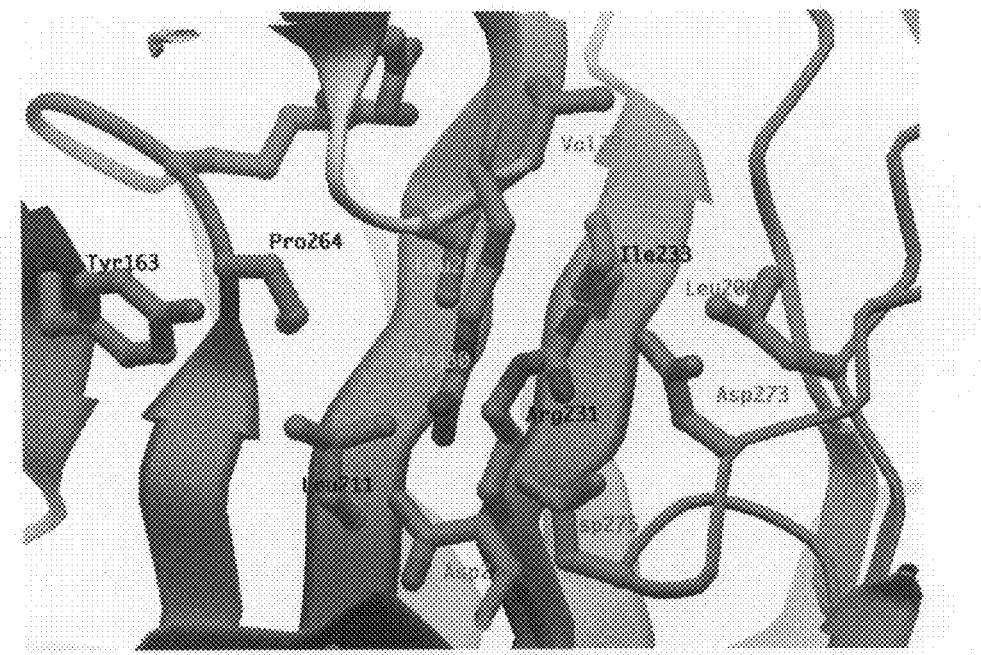

FIG. 9I shows the hydrophobic core 1 for the interaction between eBAFF-R and sTALL-1.

Figure 9J:
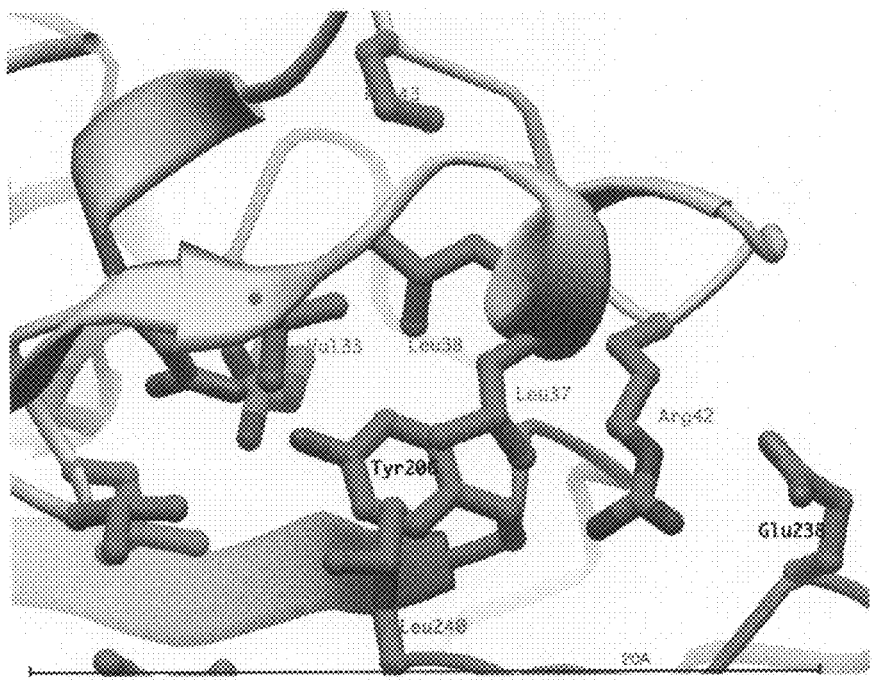

FIG. 9J shows the hydrophobic core 2 for the interaction between eBAFF-R and sTALL-1.

Figure 10A:
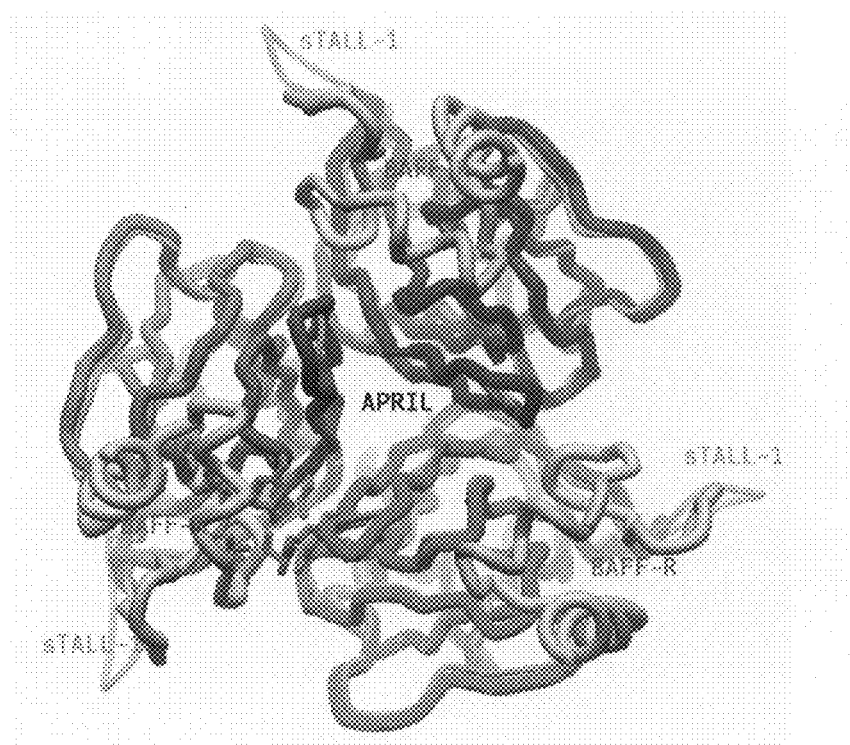

FIG. 10A is a model of APRIL and its superposition on sTALL-1 in the presence of eBAFF-R; three sTALL-1 monomers are colored pink, three models of APRIL are colored gray, magenta, and blue respectively.

Figure 10B:
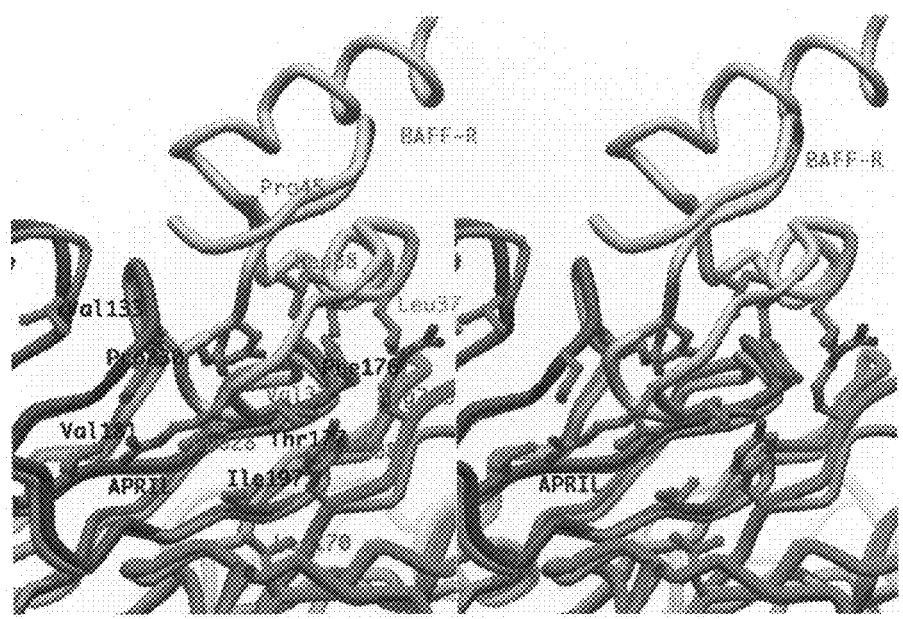

FIG. 10B shows a hypothetical overall interaction between eBAFF-R and APRIL.

DETAILED DESCRIPTION OF THE INVENTION

The present invention relates to the determination of the three-dimensional structure of sTALL-1 and sTALL-1 in complex with the extracellular domains of its cognate receptors, BCMA and BAFF-R, and to the use of such structures to develop agonists and antagonists and lead compounds for drug development in the area of therapeutic agents related to TALL-1 biological activity. The present invention specifically relates to various TALL-1 protein homologues (agonists and antagonists) that were designed using the structural information provided herein, as well as TALL-1 receptor antagonists that were designed in a similar manner. The present invention also relates to agonist homologues of APRIL, and to the use of wild-type APRIL and such homologues in a method to inhibit the activity of TALL-1. The present invention additionally relates to compositions comprising such homologues, agonists and antagonists, and to therapeutic methods of using such compounds and compositions. The invention further relates to crystalline complexes of sTALL-1 and sTALL-1 in complex with either BCMA or BAFF-R; to models of three-dimensional structures of such crystalline complexes and related structures, including models of the three dimensional structures of portions of the sTALL-1/BCMA complex or the sTALL-1/BAFF-R complex; to a method of drug design using any portion of such structures; to the design and/or identification of regulatory peptides derived from the knowledge of the three-dimensional structure of sTALL-1, the extracellular domains of BCMA, the extracellular domains of BAFF-R, and/or the complexes disclosed herein; to the compounds identified by drug design using such structures; and to the use of such compounds in therapeutic compositions and methods. These agents can be used to regulate B cell activity (e.g., B cell proliferation, B cell maturation, antibody production), autoimmunity, apoptosis, tumor cell survival, and other conditions affected by the activity of TALL-1, its receptors, and other TNF family members.

More particularly, the present inventors have determined the crystal structure of the functional soluble TALL-1 (sTALL-1) at 3.0 Å sTALL-1. The inventors have shown that the crystal structure of sTALL-1 forms a virus-like assembly with 200 Å diameter in the crystals, containing 60 sTALL-1 monomers. The cluster formation is mediated by a novel "flap" region of the sTALL-1 monomer. The virus-like assembly was also detected in solution using gel-filtration and electron microscopy. Deletion of the "flap" region disrupted the ability of TALL-1 monomers to form the virus-like assembly. Moreover, the mutant sTALL-1 bound its receptor, but could not activate NF-κB and did not stimulate B lymphocyte proliferation. Finally, the inventors found that the virus-like cluster of sTALL-1 exists in physiological conditions. Details of the structure of TALL-1 are discussed below.

In addition, the present inventors have determined the crystal structures of sTALL-1 complexed with the extracellular domains of BCMA and BAFF-R at 2.6 Å and 3.0 Å, respectively. The single cysteine rich domain (CRD) of BCMA and BAFF-R both have a saddle-like architecture, which sits on the horseback-like groove formed by four coil regions on each individual sTALL-1 monomer. Two novel structural modules D2 and D0 were revealed from these structures. Details of the structure of sTALL-1 in complex with its cognate receptors are also discussed below.

Using the information provided herein regarding the structure of TALL-1 and its receptors, one can design agonists and antagonists of the both TALL-1 and the receptors. The present inventors have identified the residues of TALL-1 that are important for trimer formation, for the interaction between trimers of TALL-1, and for binding of TALL-1 to both BCMA and BAFF-R. Additionally, the inventors have determined residues of BCMA and BAFF-R that are important for binding to TALL-1, and this information is predictive of TALL-1-binding residues of the third known receptor for TALL-1, TACI.

Finally, from sequence alignments, the truncated version of sTALL-1 is similar to APRIL (TALL-2), the closely related family member of TALL-1. Moreover, all residues that take part in the trimer-trimer interactions are not conserved between TALL-1 and TALL-2. It seems impossible for APRIL to form the virus-like cluster. It is suggested that APRIL may act as a decoy ligand in vivo. The inability of APRIL to bind to BAFF-R indicates structural diversity between TALL-1 and APRIL (Schiemann et al., (2001) *Science* 293:2111-2114). The resolution of the TALL-1 structure described herein has allowed the present inventors to model the related protein, APRIL, and to propose novel agonists of APRIL, as well as a novel function for APRIL, as a decoy ligand for TALL-1.

As demonstrated by multiple laboratories, administration of sTALL-1 can cause autoimmune like lupus in mice (Gross et al., (2000) *Nature*, 404:995-999; Mackay et al., (1999) *J Exp Med.* 190:1697-710; Khare et al., (2000) *Proc Natl Acad Sci USA.* 97:3370-5). The present inventors reason that a non-functional mutation of sTALL-1, which still has similar binding affinity to its receptors competing with native sTALL-1, could serve as a therapeutic candidate for treating autoimmune diseases. The truncated version of sTALL-1 lacks the ability to form clusters, is defective in NFκB activation function, but still binds to its cognate receptor, making it a possible candidate for this purpose. Therefore, the present inventors' discoveries have applications for designing novel TALL-1 antagonists (and agonists) and novel TALL-1 receptor antagonists (and agonists) for use in therapeutics to regulate B cell activity (e.g., B cell proliferation, B cell maturation, antibody production), autoimmunity, apoptosis, tumor cell survival, and other conditions affected by the activity of TALL-1, its receptors, and other TNF family members.

According to the present invention, general reference to TALL-1 (e.g., BAFF, THANK, BlyS or zTNF4) refers to a tumor necrosis factor (TNF)/tumor necrosis factor receptor (TNFR) family member which has been characterized as playing a role in B cell development and maturation (Shu et al., 1999, *J. Leukocyte Biology* 65:680-683; Schneider et al., 1999, *J Exp Med.* 189:1747-56; Moore et al., 1999, *Science* 285:260-263; Mukhopadhyay et al., 1999, supra; Shu et al., 2000, *Pro. Natl. Acad. Sci. USA* 97:9156-9161; Gross et al., 2000, *Nature* 404:995-999; Thompson et al., 2000, *J Exp Med* 192:129-35; Marsters et al., 2000, *Curr Biol.* 10:785-8; Xia et al., 2000, *J Exp Med.* 192:137-43; Yan et al., 2000, *Nat. Immunol.* 1:37-41; Thompson et al., 2001, Science 293: 2108-2111). The amino acid sequence of TALL-1 is represented herein by SEQ ID NO:2. SEQ ID NO:2 (encoded by the nucleic acid sequence SEQ ID NO:1) represents the full-length TALL-1 protein sequence. Amino acid positions for TALL-1 described herein are made with reference to SEQ ID NO:2, unless otherwise noted. The amino acid sequence of soluble TALL-1 (sTALL-1) is consists of positions 134 to 285 of SEQ ID NO:2. In general, reference to a TALL-1 protein can include both the full-length TALL-1 represented by SEQ ID NO:2 and the soluble TALL-1 represented by positions 134-285 of SEQ ID NO:2. The crystal structure of the sTALL-1 protein described herein comprises amino acid positions 134-285 of SEQ ID NO:2. The TALL-1 protein used for crystallization included an N-terminal His$_6$ tag, facilitating isolation and purification using nickel-chelating affinity chromatography.

Figure 1A:
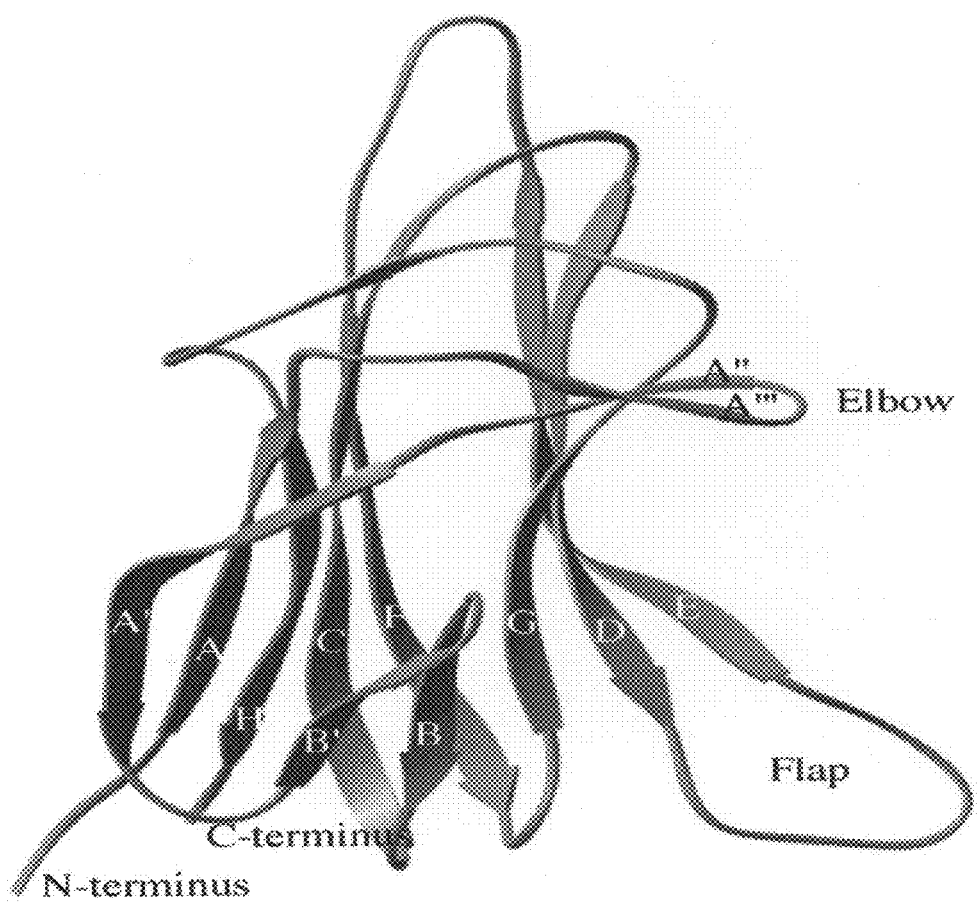
FIG. 1A is a ribbon diagram of the three-dimensional structure of sTALL-1 (residue 142-285); "elbow" and "flap" regions are unique for sTALL-1 and termed for their shapes; starting from the N-terminus, A (146-151)→A'"(158-160)→A"(163-165)→A'(168-174)→B'(178-181)→B(184-187)→C(191-201)→D(208-215)→E(226-235)→F(245-253)→G(258-242)→H(270-283).
Figure 1B:
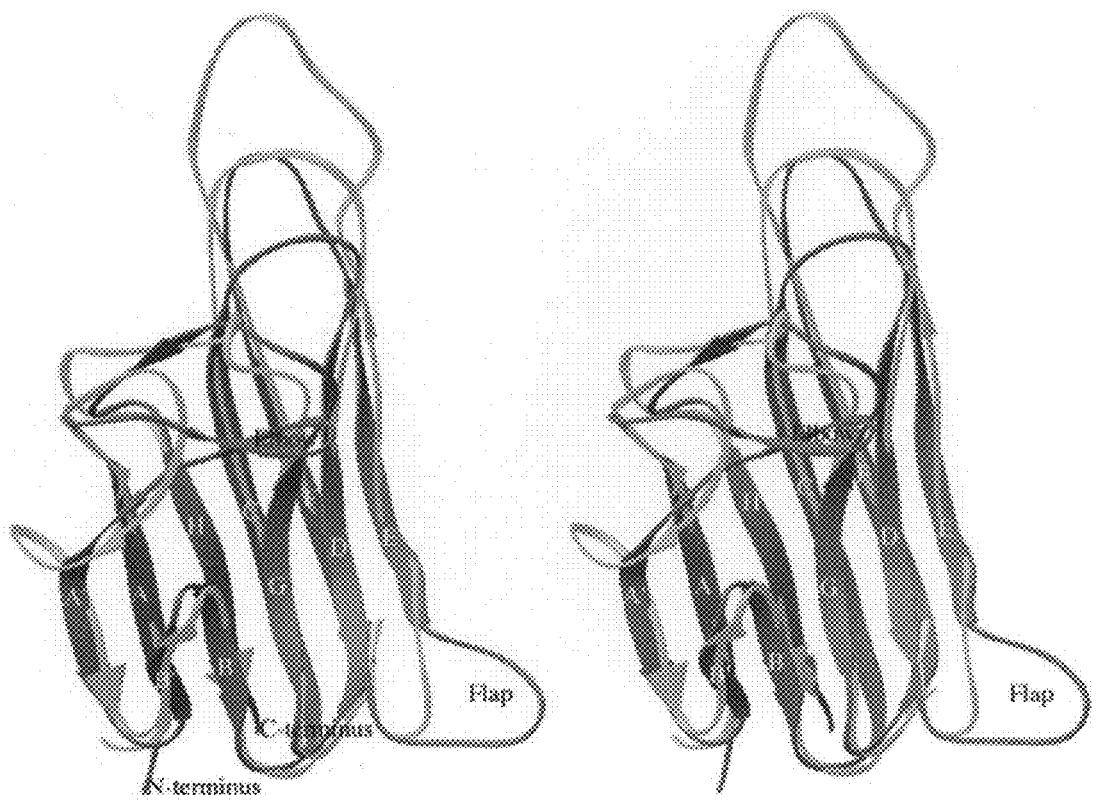
FIG. 1B is a stereo view of superimposing sTALL-1 onto TNFα (PDB ID 1TNF); sTALL-1 is colored green; TNFα is colored yellow.
Figure 1C:
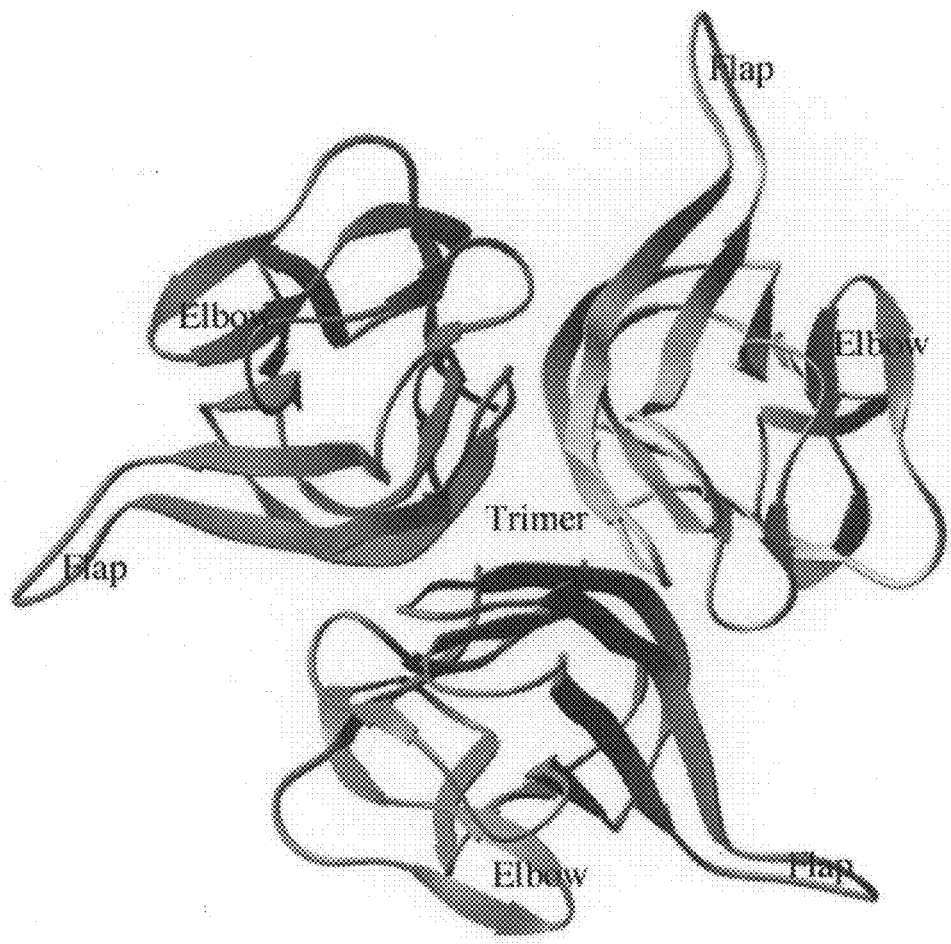
FIG. 1C is a ribbon representation of sTALL-1 trimer, looking down from the 3-axis fold that generates the trimer.
Figure 1D:
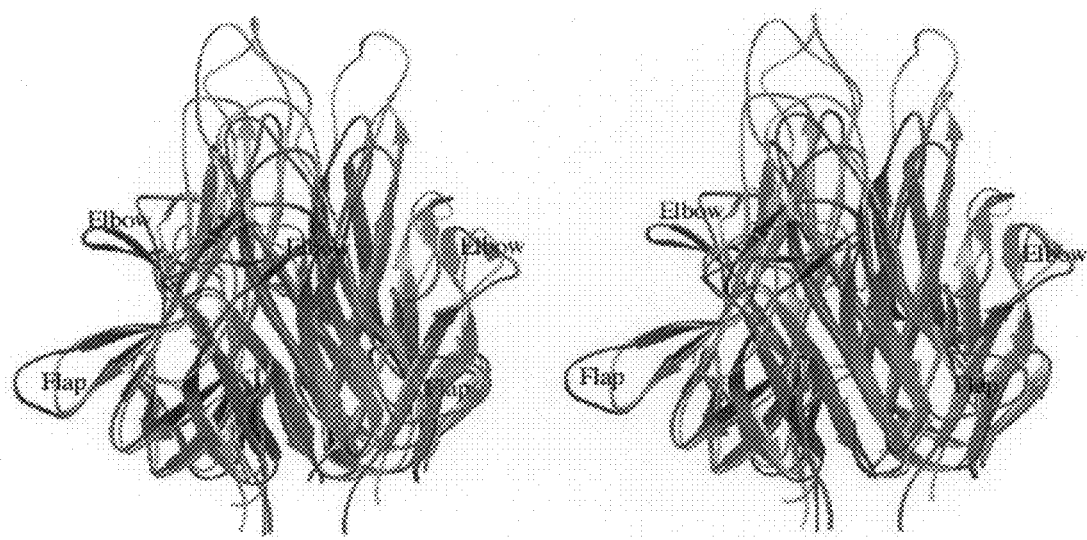
FIG. 1D is a stereo view of superimposing of sTALL-1 trimer and TNFα trimer, viewing from the orientation vertical to the 3-axis fold; sTALL1-1 is colored green, TNFα is colored gray.

The present inventors have determined that the structure of sTALL-1 consists of two layered antiparallel β strands that form a typical jellyroll-like β sandwich, as with other members of the TNF ligand family (Jones et al., (1989) *Nature* 338:225-228; Eck et al., (1989) *J. Biol. Chem.*, 264:17595-17605; Eck et al., (1992) *J. Biol. Chem.* 267:2119-2122; Karpusas et al., (1995) *Structure* 3:1031-1039; Cha et al., 1999, *Immunity* 11:253-261). Compared to known structures of other family members, the overall structure of sTALL-1 is shorter along the 3-fold axis that generates the trimers (FIG. 1B). Two unique features of TALL-1 are termed "elbow" and "flap" regions (FIG. 1A). The "elbow" region contains a short β hair-pin labeled A" and A'". The "flap" region is unique to sTALL-1 based on results of sequence alignments and structural comparisons (FIGS. 1B, 1D). The unique "flap" region of sTALL-1 mediates trimer-trimer interactions that lead to a remarkable virus-like assembly of the sTALL-1 trimers. There are 10 sTALL-1 monomers in the asymmetric unit with a space group of $P6_322$ (FIG. 2A). The 10 monomers interact to form virus-like clusters containing 60 sTALL-1 monomers (20 trimers) (FIGS. 2B, 2C). The trimer-trimer interactions are extensive. They not only include hydrogen bond networks and salt bridges, but also hydrophobic contacts. Residues involved in trimer-trimer interactions are not only from the monomer that contributes the "flap" region but also the neighboring monomer as well (FIGS. 3A and 3B). The fine details of the structure of TALL-1 are described in Example 1. The present inventors additionally showed that the virus-like cluster assembly could be visualized by electron microscopy, that the cluster assembly exists in solution as physiological pH, and that the "flap region" (and by extension the ability to form clusters) was essential for the proper function of sTALL-1 in vivo (see Example 2).

According to the present invention, general reference to a receptor for TALL-1 or a "TALL-1 receptor" generally refers to any of the cognate receptors for TALL-1, including the receptors known as BCMA (B cell maturation factor), BAFF-R (also called BR3), and TACI (Shu et al., 2000, *Pro. Natl. Acad. Sci. USA*. 97:9156-9161; Gross et al., 200, *Nature* 404:995-999; Thompson et al., 2000, *J. Exp Med.* 192:129-35; Marsters et al., 2000, *Curr Biol.* 10:785-8; Xia et al., 2000, *J Exp Med.* 192:137-43; Yan et al., 2000, *Nat. Immunol.* 1:37-41; Thompson et al., 2001, *Science* 293:2108-2111; Yan et al., 2001, *Curr Biol.* 11: 1547-1552; each of which is incorporated herein by reference in its entirety).

The amino acid sequence of BCMA is represented herein by SEQ ID NO:6. SEQ ID NO:6 (encoded by the nucleic acid sequence SEQ ID NO:5) represents the full-length BCMA protein sequence. Amino acid positions for BCMA described herein are made with reference to SEQ ID NO:6, unless otherwise noted. A soluble BCMA can include positions 1-62 of SEQ ID NO:6, or a smaller fragment within positions 1-62 of SEQ ID NO:6. The crystal structure of the eBCMA protein (extracellular domain of BCMA) described herein was produced using amino acid residues 1-52 of SEQ ID NO:6; the residues ordered in the structure model of eBCMA described herein comprises residues 5-43 of SEQ ID NO:6 (FIG. 6B). The amino acid sequence of BAFF-R is represented herein by SEQ ID NO:8. SEQ ID NO:8 (encoded by the nucleic acid sequence SEQ ID NO:7) represents the full-length BAFF-R protein sequence. Amino acid positions for BAFF-R described herein are made with reference to SEQ ID NO:8, unless otherwise noted. The crystal structure of the eBAFF-R protein (extracellular domain of BAFF-R) described herein was produced using amino acid residues 1-62 of SEQ ID NO:8; the residues ordered in the structure model of eBAFF-R described herein comprises residues 16-58 of SEQ ID NO:8 (FIG. 6C). The eBCMA and the eBAFF-R used for crystallization included a GST tag, facilitating isolation and purification using affinity chromatography.

The present inventors have determined the structure of the sTALL-1 (described above) in complex with each of eBCMA and eBAFF-R. The space group of the TALL-1 crystals remained $P6_322$ with the same cell dimensions with or without binding of the receptors. There were two virus-like clusters of TALL-1 in one unit cell, and each cluster had 60 copies of sTALL-1, 42 fully occupied eBCMA or eBAFF-R, and 6 partial copies of eBCMA or eBAFF-R. There were 12 copies of sTALL-1 free of receptors due to crystal packing. All receptors were located on the outer-extreme shell, which expands the ball-like shell another ~20 Å in each direction. The overall arrangement of the receptors on the shell resembled a sunflower with receptors as flower petals and sTALL-1 as a seed bed (FIG. 7). The interactions between sTALL-1 and eBAFF-R are similar to those between sTALL-1 and eBCMA, although details are slightly different. The interaction modes of the eBCMA and eBAFF-R with sTALL-1 are dramatically different from those found in the other TNF family members, containing at least two CRDs that bind to the cleft regions formed by two ligands. For the interactions described here, one saddle-like receptor mostly makes a one to one interaction with its ligand at the extreme end of the ligand (FIGS. 9A-9C). The difference exists not only in the CRD structure but also in the binding locations and modes.

The sequence homology between eBCMA and eTACI (extracellular domain of TACI) is obvious. This is not true for eBCMA and eBAFF-R or for eTACI and eBAFF-R. The structures of eBCMA and eBAFF-R allowed the present inventors to perform a structural based sequence alignment of eBCMA, eBAFF, and eTACI. They found that a strong pattern of similarity emerges (FIGS. 8A and 8B), and thus it can be predicted that TACI will bind to TALL-1 in a manner similar to that of BCMA and BAFF-R described herein. Details regarding the structure of eBCMA and eBAFF-R and the interaction between these receptors and TALL-1 are described in Example 6.

The present inventors' results are not consistent with two published results (Schneider et al., 1999, *J Exp Med* 189: 1747-56; and Kanakaraj et al., 2001, *Cytokine* 13:25-31), both of which claimed that sTALL-1/BAFF existed only as trimers. Moreover, two publications of TALL-1 structure published subsequent to the filing of the priority document for this application did not report the assembly of TALL-1 monomers into the virus-like cluster described herein (Oren et al., Feb. 25, 2002, *Nat. Struct. Biol.* 9(4):288-292; Karpusas et al., Feb. 1, 2002, *J. Mol. Biol.* 315:1145-1154).

However, four lines of evidence support the present inventors' belief that the crystal structure described herein reflects the actual interactions of the complexes in solution and in vivo. First, co-expression of sTALL-1 with eBCMA or eBAFF-R generates the virus-like cluster in solution as judged by gel-filtration column and SDS-phage analysis at a ratio of 1:1 (sTALL-1: eBCMA or eBAFF-R). Different salt concentrations (from 100 mM to 1M NaCl) produce the same elution profile, in which complexes of sTALL-1 with eBCMA or eBAFF-R elute at a void volume on superdex-200. Thus, binding between ligand and receptors is stable and insensitive to salt concentrations. Purified samples of the preformed complexes were subjected to crystallization trials. Crystals of both complexes have been obtained, however neither of them diffracted. The results further confirmed that the "flap" region of TALL-1 which is involved in clustering, is not part of the receptor binding site. Furthermore, these results suggest that the pre-binding of receptors to sTALL-1 disrupts the original molecular packing in the sTALL-1 crystals and that the receptors are located on the surface of the sTALL-1 cluster. Second, in the receptor soaked sTALL-1 crystals, all seven fully occupied receptors and one partial receptor have equivalent binding sites on sTALL-1 in the asymmetry unit, so the binding is highly specific. Third, eBCMA and eBAFF-R have a similar binding mode and occupy the same site on sTALL-1. Fourth, each of the three C-termini of eBCMA and eBAFF-R on the sTALL-1 trimer point to the same direction, the putative membrane surface for trimerization (FIGS. 7C and 7D). Therefore, without being bound by theory, the present inventors believe that the interactions revealed from the complex structures represent the actual interactions between TALL-1/BCMA and TALL-1/BAFF-R in vivo.

Finally, the present inventors have modeled APRIL based on the sTALL-1 structure, benefiting from the high primary sequence homology between TALL-1 and APRIL.

According to the present invention, general reference to APRIL refers to a tumor necrosis factor (TNF)/tumor necrosis factor receptor (TNFR) family member which is the closest family member to TALL-1, and is represented herein by SEQ ID NO:4 (encoded by the nucleic acid sequence SEQ ID NO:3). APRIL has low abundance in normal tissues, but is present at high level in transformed cell lines and in variety of human cancers (Hahne et al., 1998, *J. Exp. Med.* 188:1185-1190). More recent data show that BAFF-R does not bind APRIL (Thompson et al., 2001, *Science* 293:2108-2111; Yan et al., 2001, *Curr Biol.* 11: 1547-1552), suggesting that APRIL is dispensable for B cell maturation (Thompson et al., 2001, supra; Yan et al., 2001, supra; Schneider et al., 2001, *J. Exp. Med.* 194:1691-1697), although it binds to BCMA and TACI with an affinity similar to sTALL-1 (Yu et al. 2000, *Nature immunol.* 1:252-256). Nevertheless, APRIL-deficient mice die in utero (Mackay et al., 2002, *TRENDS in Immunology* 23:113-115), leaving the role of APRIL in vivo at the time of this invention a mystery.

The final built model of APRIL was imported to the minimization program in CNS (Brunger et al., 1998, *Acta Cryst* D54:905-921, and the output coordinates were superimposed on the sTALL-1 structure (FIG. 10A). All residues from eBAFF-R that are involved in the interactions between the eBAFF-R and sTALL-1 are displayed (FIG. 10B). All equivalent residues in APRIL, which are close to the receptor binding surface in sTALL-1 are also shown (FIG. 10B). To the present inventors' surprise, the interactions were extremely similar to those found in the complexes of eBCMA or eBAFF-R with sTALL-1. The most obvious difference between sTALL-1 and APRIL is in the "flap" region (8 residues; 217-224 of SEQ ID NO:2) of sTALL-1, which is missing in APRIL (Shu et al., 1999, *J. Leukocyte Biology* 65:680-683). The present inventors have reported a mutated version of sTALL-1 with 8 residues of the "flap" region replaced by two glycine residues, and this mutant was not functional in transfection assays or in the B-cell stimulation assays, but had a binding affinity to its receptors similar to that of the native sTALL-1. The present inventors have determined the structure of this mutated sTALL-1 at 1.7 Å resolution by MIR, and it is almost identical to the sTALL-1 except for the missing flap (data not shown). Moreover, this mutated sTALL-1 is a close model of APRIL. Therefore, without being bound by theory, the present inventors believe that APRIL may be serving as a decoy ligand, reducing the opportunity for sTALL-1 to bind to the same receptor. This role is similar to the decoy death receptors, which are essential for cells to survive (Cha et al., 1999, *Immunity* 11:253-261; Mongkolsapaya et al., 1999, *Nat. Struct. Biol.* 6:1048-1053; Hymowitz et al., 1999, *Mol. Cell.* 4:563-571). As shown in Example 6, although APRIL does not bind to BAFF-R under physiological conditions (pH7.5), the present inventors have produced at least two homologues of BAFF-R that can bind to APRIL under physiological conditions. Also, the present inventors have demonstrated that APRIL can form heterotrimers with sTALL-1 under physiological conditions. These results and the implications therefore are discussed in detail below.

As discussed above, various details of the structure of TALL-1, of the TALL-1 receptors BCMA and BAFF-R, and of the interactions between TALL-1 monomers and between TALL-1 and its receptors are described herein and particularly in the Examples section. This information can now be used to design novel agonists and antagonists of TALL-1 and its cognate receptors, embodiments of which are described in detail below.

Accordingly, one embodiment of the present invention relates to a variety of TALL-1 homologues and particularly, TALL-1 agonist and TALL-1 antagonist proteins, that are designed using the structural information provided herein. The following discussion is made with reference to TALL-1 proteins, including homologues thereof, but it is to be understood, however, that the general definitions of terms and methods are intended to apply to the discussion of an isolated TALL-1 receptor and homologues thereof, as well as to discussion of APRIL and homologues thereof, unless otherwise modified within the specific discussion of the TALL-1 receptor or APRIL.

An isolated protein (e.g., an isolated TALL-1 protein), according to the present invention, is a protein that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. Preferably, an isolated protein, and particularly, an isolated TALL-1 (including fragments and homologues thereof), is produced recombinantly. The terms "fragment", "segment" and "portion" can be used interchangeably herein with regard to referencing a part of a protein. It will be appreciated that, as a result of the determination of the tertiary structure of biologically active portions of TALL-1 and the extracellular domains of two of its receptors herein, various portions and residues of TALL-1 and it receptors will now be considered to be particularly valuable for mutational analyses and various biological assays, as well as for the development of therapeutic proteins and compounds or lead compounds for drug design, and also for computer-assisted drug design methods, as discussed herein. Such portions of TALL-1 and its receptors and methods of using such portions are explicitly contemplated to be part of the present invention.

According to the present invention, general reference to TALL-1 is reference to a protein that typically contains any biologically active portion of a native or wild-type TALL-1 protein (e.g., a portion that can exhibit at least one biological activity associated with native (wild-type) TALL-1 or a portion that at least binds to a given receptor), and includes full-length TALL-1, soluble proteins, biologically active fragments of TALL-1, TALL-1 fusion proteins, or any homologue of a naturally occurring TALL-1, as described in detail below.

Similarly, general reference to a TALL-1 receptor is reference to a protein that typically contains any biologically active portion of a native or wild-type TALL-1 receptor (e.g., a portion that can exhibit at least one biological activity associated with native (wild-type) TALL-1 receptor or a portion that at least binds to a given ligand, such as TALL-1), and includes full-length TALL-1 receptor, soluble receptors, biologically active fragments of TALL-1 receptors, TALL-1 receptor fusion proteins, or any homologue of a naturally occurring TALL-1 receptor, as described in detail below. General reference to APRIL herein is a reference to a protein that typically contains any biologically active portion of a native or wild-type APRIL protein (e.g., a portion that can exhibit at least one biological activity associated with native (wild-type) APRIL or a portion that at least binds to a given receptor), and includes full-length APRIL, soluble proteins, biologically active fragments of APRIL, APRIL fusion proteins, or any homologue of a naturally occurring APRIL (including both agonists and antagonists), as described in detail below.

Reference herein to a protein from a specific organism, such as a "human TALL-1", by way of example, refers to a TALL-1 protein from a human or to a TALL-1 protein that has been otherwise produced from the knowledge of the primary structure (e.g., sequence) and/or the tertiary structure of a naturally occurring TALL-1 protein from Homo sapiens. In other words, a human TALL-1 protein includes any TALL-1 protein that has the structure and function of a naturally occurring TALL-1 from Homo sapiens or that has a structure and function that is sufficiently similar to a human TALL-1 such that the TALL-1 protein is a homologue of a naturally occurring TALL-1 from Homo sapiens. As such, a human TALL-1 protein, by way of example, can include purified, partially purified, recombinant, mutated/modified and synthetic proteins.

A homologue of any protein described herein includes proteins which differ from a naturally occurring protein in that at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol). In other words, a homologue of a protein according to the invention includes proteins that have been mutated or modified, as compared to the wild-type protein. According to the present invention, the terms "modification" and "mutation" can be used interchangeably, particularly with regard to the modifications/mutations to the amino acid sequences of TALL-1, APRIL or TALL-1 receptors (or nucleic acid sequences) described herein. A homologue can have either enhanced, decreased, or substantially similar properties (including combinations thereof, when different properties are assessed) as compared to the naturally occurring protein or peptide. A homologue can include an agonist of a protein or an antagonist of a protein.

Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

Modification of proteins described herein typically result in homologues that have agonistic and/or antagonistic biological activities as compared to the naturally occurring (wild-type) protein. In general, the biological activity or biological action of a protein refers to any function(s) exhibited or performed by the protein that is ascribed to the naturally occurring form of the protein as measured or observed in vivo (i.e., in the natural physiological environment of the protein) or in vitro (i.e., under laboratory conditions). Modifications of a protein, such as in a homologue or mimetic (discussed below), may result in proteins having the substantially the same biological activity as the naturally occurring protein, or in proteins having decreased or increased biological activity as compared to the naturally occurring protein. Modifications which result in a decrease in protein expression or a decrease in the activity of the protein, can be referred to as inactivation (complete or partial), down-regulation, or decreased action of a protein. Similarly, modifications which result in an increase in protein expression or an increase in the activity of the protein, can be referred to as amplification, overproduction, activation, enhancement, up-regulation or increased action of a protein.

According to the present invention, an isolated protein described herein, including a biologically active homologue (agonist or antagonist) or fragment thereof, has at least one characteristic biological activity of the wild-type, or naturally occurring protein (which can vary depending on whether the homologue or fragment is an agonist, antagonist, or mimic of the wild-type protein). For example, the biological activity of TALL-1 can include, but is not limited to, binding to at least one TALL-1 receptor (e.g., BCMA, BAFF-R, TACI); activation of at least one TALL-1 receptor; formation of trimers with other TALL-1 monomers, formation of viral-like clusters among TALL-1 trimers, an ability to costimulate B lymphocyte proliferation; an ability to costimulate B lymphocyte activation; and/or an ability to support B lymphocyte survival and development. Biological activity of a TALL-1 receptor can include, but is not limited to: an ability to bind to a ligand, including TALL-1 or APRIL; receptor translocation within a cell upon ligand binding; NFκB activation; TRAF5, TRAF6, NIK, IKKα and/or IKKβ activation; costimulation of B cell proliferation; costimulation of B cell activation; and enhancement of B cell survival. Biological activity of APRIL can include, but is not limited to: binding to at least one APRIL receptor (e.g., BCMA, TACI); regulation of B cell survival, development or maturation. Biological activities of TALL-1, APRIL and TALL-1/APRIL receptors are known in the art and are described in: Shu et al., 1999, J. Leukocyte Biology 65:680-683; Schneider et al., 1999, J Exp Med. 189:1747-56; Moore et al., 1999, Science 285:260-263; Mukhopadhyay et al., 1999, supra; Shu et al., 2000, Pro. Natl. Acad. Sci. USA 97:9156-9161; Gross et al., 2000, Nature 404:995-999; Thompson et al., 2000, J Exp Med 192:129-35; Marsters et al., 2000, Curr Biol. 10:785-8; Xia et al., 2000, J Exp Med. 192:137-43; Yan et al., 2000, Nat. Immunol. 1:37-41; Yu et al., 2000, Nat. Immunol. 1:252-6; Thompson et al., 2001, Science 293: 2108-2111; and Yan et al., 2001, Curr Biol. 11(19):1547-52; each of which is incorporated herein by reference in its entirety.

Methods of detecting and measuring such biological activity, including measuring agonist or antagonist activity, include, but are not limited to measurement of transcription of the protein; measurement of translation of the protein; measurement of secretion of soluble forms of the protein (TALL-1 and APRIL); measurement of binding of the protein to its receptor (TALL-1 and APRIL); measurement of binding of the protein to its ligand (BCMA, BAFF-R, TACI); measurement of B cell proliferation; measurement of B cell activation; measurement of B lymphocyte cytokine production; measurement of NFκB activation; measurement of TRAF5, TRAF6, NIK, IKKα or IKKβ activation; measurement of immunoglobulin maturation; measurement of immunoglobulin production and secretion; measurement of calcium mobilization; or measurement of phosphorylation of signal transduction proteins. It is noted that homologue of a protein according to the present invention is not required have all of the biological activities of the wild-type protein. For example, a TALL-1 homologue may bind to a TALL-1 receptor, but may not be able to activate the receptor. Various homologues are useful as agonists or antagonists of the wild-type protein and in addition, some homologues are useful in diagnostic assays, as lead compounds for drug design, or in screening assays, for example, or for other purposes such as antibody production.

In general, methods to measure protein expression levels include, but are not limited to: western blotting, immunocytochemistry, flow cytometry or other immunologic-based assays; assays based on a property of the protein including but not limited to DNA binding, ligand binding, or interaction with other protein partners. Binding assays are also well known in the art. For example, a BIAcore machine can be used to determine the binding constant of a complex between two proteins. The dissociation constant for the complex can be determined by monitoring changes in the refractive index with respect to time as buffer is passed over the chip (O'Shannessy et al. Anal. Biochem. 212:457-468 (1993); Schuster et al., Nature 365:343-347 (1993)). Other suitable assays for measuring the binding of one protein to another include, for example, immunoassays such as enzyme linked immunoabsorbent assays (ELISA) and radioimmunoassays (RIA), or determination of binding by monitoring the change in the spectroscopic or optical properties of the proteins through fluorescence, UV absorption, circular dichroism, or nuclear magnetic resonance (NMR).

Measurement of expression of transcripts can be performed by any of a variety of known methods in the art. For RNA expression, methods include but are not limited to, extraction of cellular mRNA and northern blotting using labeled probes that hybridize to transcripts encoding all or part of the mRNA encoding the protein of interest; amplification of mRNA using sequence-specific primers and reverse transcriptase-polymerase chain reaction (RT-PCR), followed by quantitative detection of the product by any of a variety of means; extraction of total RNA from the cells, which is then labeled and used to probe cDNAs. The term "quantifying" or "quantitating" when used in the context of quantifying transcription levels of a gene can refer to absolute or to relative quantification. Absolute quantification may be accomplished by inclusion of known concentration(s) of one or more target nucleic acids and referencing the hybridization intensity of unknowns with the known target nucleic acids (e.g. through generation of a standard curve). Alternatively, relative quantification can be accomplished by comparison of hybridization signals between two or more genes, or between two or more treatments to quantify the changes in hybridization intensity and, by implication, transcription level.

Included in the invention are both agonists and antagonists of proteins described herein. As used herein, reference to an agonist, as in a "TALL-1 agonist" or "APRIL agonist" refers to any compound that is characterized by the ability to agonize (e.g., stimulate, induce, increase, enhance, or mimic) the biological activity of the naturally occurring protein (TALL-1 or APRIL, respectively) as described herein (e.g., by interaction/binding with and/or activation of a receptor for the naturally occurring protein). More particularly, an agonist as set forth above can include any compound that selectively binds to and/or activates or increases the activation of a TALL-1 receptor or APRIL receptor, respectively, or otherwise mimics or enhances the activity of the natural ligand, TALL-1 or APRIL, respectively. Similarly, reference to a "TALL-1 receptor agonist" or "APRIL receptor agonist" refers to any compound that is characterized by its ability to agonize (e.g., stimulate, induce, increase, enhance) the biological activity of the naturally occurring receptor as described herein (e.g., by interaction/binding with ligands of the receptor and mimicking or enhancing the biological activity of the receptor).

Agonists can include, but are not limited to, a protein, a peptide, a nucleic acid, or any product of drug/compound/peptide design or selection and includes any homologue of the protein, binding protein (e.g., an antibody), agent, or any suitable product of drug/compound/peptide design or selection which is characterized by its ability to agonize (e.g., stimulate, induce, increase, enhance) the biological activity of the naturally occurring protein (e.g., TALL-1) in a manner similar to the natural agonist (e.g., TALL-1). Agonists of TALL-1, and TALL-1 receptors of the present invention can be useful in methods for increasing B cell development, B cell proliferation and/or B cell survival. Such agonists might be useful, for example, in conditions or diseases where B lymphocyte deficiency or hypoproliferation is problematic. Interestingly, the present inventors believe that APRIL agonists (compounds that agonize the activity of APRIL) can effectively serve as TALL-1 antagonists (e.g., they may antagonize the activity of TALL-1).

The phrase, "antagonist", as in a "TALL-1 antagonist" or "APRIL antagonist" refers to any compound which inhibits (e.g., antagonizes, reduces, decreases, blocks, reverses, or alters) the effect of a TALL-1 agonist or an APRIL agonist, respectively, as described above. More particularly, a TALL-1 antagonist or APRIL antagonist is capable of associating with a receptor (e.g., a TALL-1 receptor or an APRIL receptor, respectively), or otherwise acts in a manner relative to TALL-1 or APRIL activity, respectively, such that the biological activity of the receptor or of the natural agonist, is decreased in a manner that is antagonistic (e.g., against, a reversal of, contrary to) to the natural action of natural agonist. For example, an antagonist of TALL-1 could competitively inhibit the interaction between a natural TALL-1 and its receptor, and/or could induce a different effect on the receptor as compared to the effect induced by TALL-1. Similarly, a TALL-1 receptor antagonist or an APRIL receptor antagonist is capable of mimicking the structure of the natural receptor, and/or associating with TALL-1 or APRIL, respectively, in a manner that is antagonistic (e.g., against, a reversal of, contrary to) to the natural action of the receptor or the receptor upon binding to the natural ligand. Such antagonists can include, but are not limited to, a protein, peptide, a nucleic acid (including ribozymes and antisense) or product of drug/compound/peptide design or selection that provides the antagonistic effect. Antagonists of TALL-1 or TALL-1 receptor antagonists can be useful in methods for decreasing B cell development, B cell proliferation and/or B cell survival, such as in conditions or diseases where B cell hyperproliferation, or inappropriate B cell development or survival (e.g., autoimmune disease) is problematic.

Proteins of the present invention, including homologues, are preferably retrieved, obtained, and/or used in "substantially pure" form. As used herein, "substantially pure" refers to a purity that allows for the effective use of the protein in vitro, ex vivo or in vivo according to the present invention. For a protein to be useful in an in vitro, ex vivo or in vivo method according to the present invention, it is substantially free of contaminants, other proteins and/or chemicals that might interfere or that would interfere with its use in a method disclosed by the present invention, or that at least would be undesirable for inclusion with the protein when it is used in a method disclosed by the present invention. For example, for a TALL-1 protein, such methods can include crystallization of the protein or use of all or a portion of the protein for mutational analysis, for antibody production, for agonist/antagonist identification assays, and all other methods disclosed herein. For a TALL-1 antagonist protein, such methods include use of the antagonist in a therapeutic composition or in a screening assay. Preferably, a "substantially pure" protein, as referenced herein, is a protein that can be produced by any method (i.e., by direct purification from a natural source, recombinantly, or synthetically), and that has been purified from other protein components such that the protein comprises at least about 80% weight/weight of the total protein in a given composition (e.g., the protein is about 80% of the protein in a solution/composition/buffer), and more preferably, at least about 85%, and more preferably at least about 90%, and more preferably at least about 91%, and more preferably at least about 92%, and more preferably at least about 93%, and more preferably at least about 94%, and more preferably at least about 95%, and more preferably at least about 96%, and more preferably at least about 97%, and more preferably at least about 98%, and more preferably at least about 99%, weight/weight of the total protein in a given composition.

A variety of homologues of TALL-1, APRIL and TALL-1 receptors are described herein. Although specific differences between a homologue and the wild-type protein are described below, in general, the homologue may have other modifications that do not necessarily effect the structure or biological activity of the homologue, but which cause it to have a different linear sequence as compared to the wild-type sequence. For example, a homologue having specified substantive modifications may also have multiple conservative amino acid substitutions so that the overall sequence identity between the wild-type protein and the homologue is less than if just the specified substantive modifications were made. Conservative substitutions typically include substitutions within the following groups: glycine and alanine; valine, isoleucine and leucine; aspartic acid, glutamic acid, asparagine, and glutamine; serine and threonine; lysine and arginine; and phenylalanine and tyrosine. Substitutions may also be made on the basis of conserved hydrophobicity or hydrophilicity (Kyte and Doolittle, *J. Mol. Biol.* (1982) 157: 105-132), or on the basis of the ability to assume similar polypeptide secondary structure (Chou and Fasman, *Adv. Enzymol.* (1978) 47: 45-148, 1978). Therefore, in general, a homologue according to the present invention (e.g., a TALL-1 homologue, an APRIL homologue, or a TALL-1 receptor homologue) has an amino acid sequence that is at least about 50% identical to the amino acid sequence of the naturally occurring, or wild-type protein, (e.g., for TALL-1, the wild-type protein is represented herein as SEQ ID NO:2), and in another aspect at least about 55%, and in another aspect at least about 60%, and in another aspect at least about 65%, and in another aspect at least about 75%, and in another aspect at least about 75%, and in another aspect at least about 80%, and in another aspect at least about 85%, and in another aspect at least about 90%, and in another aspect at least about 95% identical to the amino acid sequence of the naturally occurring protein.

As used herein, unless otherwise specified, reference to a percent (%) identity refers to an evaluation of homology which is performed using: (1) a BLAST 2.0 Basic BLAST homology search using blastp for amino acid searches, blastn for nucleic acid searches, and blastX for nucleic acid searches and searches of translated amino acids in all 6 open reading frames, all with standard default parameters, wherein the query sequence is filtered for low complexity regions by default (described in Altschul, S. F., Madden, T. L., Schäffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST). It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", *FEMS Microbiol Lett.* 174: 247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
  Reward for match=1
  Penalty for mismatch=−2
  Open gap (5) and extension gap (2) penalties
  gap x_dropoff (50) expect (10) word size (11) filter (on)
For blastp, using 0 BLOSUM62 matrix:
  Open gap (11) and extension gap (1) penalties
  gap x_dropoff (50) expect (10) word size (3) filter (on).

In one aspect, a homologue of a protein described herein can also include proteins having an amino acid sequence comprising at least 25 contiguous amino acid residues of the wild-type sequence (i.e., 25 contiguous amino acid residues having 100% identity with 25 contiguous amino acids of the wild-type sequence). In one embodiment, a homologue of the present invention includes proteins having amino acid sequences comprising at least about 30, or at least about 40, or at least about 45, or at least about 50, or at least about 55, or at least about 60, or at least about 65, or at least about 70, or at least about 75, or at least about 80, or at least about 85, or at least about 90, contiguous amino acid residues of the wild-type sequence, and so on, in whole integers up to just less than the full length of the wild-type protein. According to the present invention, the term "contiguous" or "consecutive", with regard to nucleic acid or amino acid sequences described herein, means to be connected in an unbroken sequence. For example, for a first sequence to comprise 30 contiguous (or consecutive) amino acids of a second sequence, means that the first sequence includes an unbroken sequence of 30 amino acid residues that is 100% identical to an unbroken sequence of 30 amino acid residues in the second sequence. Similarly, for a first sequence to have "100% identity" with a second sequence means that the first sequence exactly matches the second sequence with no gaps between nucleotides or amino acids.

Further, any of the amino acid sequences described herein can be produced with from at least one, and up to about 20, additional heterologous amino acids flanking each of the C- and/or N-terminal ends of the specified amino acid sequence.

The resulting protein or polypeptide can be referred to as "consisting essentially of" the specified amino acid sequence. According to the present invention, the heterologous amino acids are a sequence of amino acids that are not naturally found (i.e., not found in nature, in vivo) flanking the specified amino acid sequence, or that are not related to the function of the specified amino acid sequence, or that would not be encoded by the nucleotides that flank the naturally occurring nucleic acid sequence encoding the specified amino acid sequence as it occurs in the gene, if such nucleotides in the naturally occurring sequence were translated using standard codon usage for the organism from which the given amino acid sequence is derived. Similarly, the phrase "consisting essentially of", when used with reference to a nucleic acid sequence herein, refers to a nucleic acid sequence encoding a specified amino acid sequence that can be flanked by from at least one, and up to as many as about 60, additional heterologous nucleotides at each of the 5' and/or the 3' end of the nucleic acid sequence encoding the specified amino acid sequence. The heterologous nucleotides are not naturally found (i.e., not found in nature, in vivo) flanking the nucleic acid sequence encoding the specified amino acid sequence as it occurs in the natural gene or do not encode a protein that imparts any additional function to the protein or changes the function of the protein having the specified amino acid sequence.

With regard to specific embodiments of the invention, one aspect of the invention relates to a TALL-1 antagonist protein. A TALL-1 antagonist protein is a TALL-1 homologue (i.e., mutant) that antagonizes the biological activity of a wild-type, or naturally occurring TALL-1 protein, as discussed above. A TALL-1 antagonist is generally a TALL-1 homologue which comprises at least one amino acid modification as compared to a naturally occurring TALL-1 or is a portion of TALL-1 that contains the modification. The modifications to the amino acid sequence of the mutant TALL-1 can include any of the modifications to any amino acid position corresponding to any of the target residues identified herein based on the determination of the structure of TALL-1. In one embodiment of the invention, an antagonist TALL-1 protein is disclosed that has an amino acid sequence comprising at least one modification as compared to a naturally occurring TALL-1, wherein the modification is in a region selected from: (1) the "flap" region of TALL-1 (discussed in detail below); (2) a region other than the "flap" that participates in trimer-trimer associations or "clustering" of TALL-1 trimers; (3) a region that is involved in formation of TALL-1 trimers; and/or (4) a region of TALL-1 that is associated with binding to a TALL-1 receptor (e.g., BCMA, BAFF-R or TACI). Specific regions of TALL-1 and amino acid residues that are associated with each of these functions are described in detail in the Examples section.

In a first embodiment, the TALL-1 antagonist protein comprises an amino acid sequence that differs from the amino acid sequence of the wild-type protein (e.g., SEQ ID NO:2) by a modification in at least one region of the protein or in at least one amino acid residue of the protein that was determined by the present inventors, based on the structural analysis of TALL-1 disclosed herein, to play a role in the biological activity of TALL-1, other than the binding of TALL-1 to its receptor. Resulting TALL-1 antagonist proteins will have reduced biological activity as compared to a wild-type protein and can serve as competitive inhibitors of TALL-1, for example. Preferably, these TALL-1 antagonists will retain the ability to bind to a TALL-1 receptor and in a most preferred embodiment, these TALL-1 antagonists will have modifications that result in increased binding affinity for a TALL-1 receptor as compared to the binding affinity between wild-type TALL-1 and the receptor.

In one aspect, the above-described TALL-1 antagonist comprises an amino acid sequence that differs from SEQ ID NO:2 by at least one modification in the region connecting β strands D and E that reduces the biological activity of the TALL-1 antagonist as compared to wild-type TALL-1. As discussed in detail above and in the Examples, the present inventors have discovered that TALL-1 has a unique structure denoted the "flap" which mediates the viral-like clustering of TALL-1 trimers and which the inventors have shown is necessary for the biological activity of TALL-1. The region connecting β strands D and E of TALL-1 (see examples and figures) forms this flap, which includes amino acid residues 217-224 of SEQ ID NO:2. The present inventors have also produced a mutant TALL-1 in which these residues were deleted and replaced with two glycine residues (see Example 3). This mutant, while still able to bind to the TALL-1 receptors, was not able to activate the receptor or stimulate B cell proliferation (i.e., overall, it did not have TALL-1 biological activity). Moreover, the present inventors have shown that this deletion abolished the cluster forming ability of TALL-1 homologue and had a negative effect on the formation of TALL-1 trimers (see Examples). In one embodiment, this TALL-1 antagonist protein comprises an amino acid sequence that differs from SEQ ID NO:2 by a modification in at least one amino acid residue selected from: Val217, His218, Val219, Phe220, Gly221, Asp222, Glu223, and Leu224. In another aspect, this TALL-1 antagonist protein comprises an amino acid sequence that differs from SEQ ID NO:2 by a modification in at least two, three, four, five, six, seven, or all eight of the above-identified amino acid residues. It is noted that throughout the application, amino acid residues are denoted using the art-recognized 3 letter code.

According to the invention, the residues can be deleted, derivatized to reduce the ability of the residues to interact with residues on other TALL-1 monomers as described herein for the flap region residues, or substituted with non-natural amino acid residues that reduce the ability of the homologue to interact with residues on other TALL-1 monomers as described herein for the flap region residues. As used throughout this disclosure, reference to "non-natural" residues describes amino acid residues that are used to modify a protein (e.g., by insertion), but which do not naturally occur at the insertion position in the wild-type protein. In addition, one or more non-natural amino acid residues can be inserted to replace one or more (not necessarily an equivalent number) of deleted residues in the homologue sequence. For example, as exemplified herein, two glycine residues were inserted in place of a deletion of the entire 8 amino acid flap sequence to produce a TALL-1 antagonist with reduced biological activity.

Modifications in this region can produce a TALL-1 antagonist protein that has a reduced ability to form a trimer with other TALL-1 monomers. "Other TALL-1 monomers", as used herein, can refer to any TALL-1 monomer other than the monomer that is the reference homologue, including wild-type TALL-1 monomers and/or other TALL-1 homologue monomers (having the same or different modifications as the reference homologue). Therefore, a TALL-1 antagonist monomer can associate (e.g., to form a trimer, or when already in a trimer, to associate with another trimer), or attempt to associate, with wild-type monomers, with other TALL-1 antagonist monomers, or with mixtures thereof (e.g., to form heterotrimers), in vitro or in vivo. Modifications in this region can also produce a TALL-1 antagonist that has a reduced or abolished ability, when in a trimer with two other TALL-1 monomers, to interact with other TALL-1 trimers, such as to form the viral-like cluster of trimers described herein. According to the present invention, to reduce binding between a TALL-1 homologue and another protein (e.g., monomers, trimers, receptors) refers to any detectable decrease in the binding affinity as compared to the binding affinity between the wild-type TALL-1 monomer and the same other protein. To abolish binding between a TALL-1 homologue and another protein refers to a substantial abolition (reduction, elimination, prevention) of binding affinity as compared to the binding affinity between the wild-type TALL-1 monomer and the same other protein, wherein the binding affinity is reduced by at least about 50%, and more preferably by at least about 60%, and more preferably by at least about 70%, and more preferably by at least about 80%, and more preferably at least about 90%, and more preferably at least about 95%, and more preferably at least about 96%, and more preferably at least about 97%, and more preferably at least about 98%, and more preferably at least about 99%, and most preferably, wherein binding of the mutated TALL-1 monomer to another protein is undetectable using standard binding assays. Similarly, to increase binding between a TALL-1 antagonist and another protein (e.g., a receptor; see discussion below) refers to any detectable increase in the binding affinity as compared to the binding affinity between the wild-type TALL-1 monomer and the same other protein. Assays for detecting and measuring binding, including binding affinity, between two proteins are well known in the art and have been discussed previously herein.

As discussed above, it is preferred that the above-described TALL-1 antagonist protein retain the ability to bind to a TALL-1 receptor, including, but not limited to, BCMA, BAFF-R and TACI. In this way, the TALL-1 antagonist can competitively inhibit wild-type TALL-1 by binding to, but not activating, TALL-1 receptors. In one aspect, the TALL-1 antagonist protein retain some or all of the amino acid residues that participate in binding to a TALL-1 receptor, including, but not limited to, Tyr163, Tyr206, Leu211, Arg231, Ile233, Pro264, Arg265, Glu266, Leu200, Leu240, Asp273, Asp275, Glu238 and Asp222 of SEQ ID NO:2. The residues are spatially arranged in the amino acid sequence of the TALL-1 homologue in a manner that is similar enough to the spatial arrangement in the wild-type TALL-1, so that binding to a TALL-1 receptor is retained. At a minimum, this includes the amino acid residues that occur in positions 163-275 in the wild-type protein. However, it is to be understood that the positions of these residues within the mutated TALL-1 protein can vary somewhat from the corresponding positions in the wild-type protein, as long as the mutated TALL-1 protein maintains the ability to bind to a TALL-1 receptor. For example, one might be able to construct a TALL-1 antagonist protein where the Tyr that occurs at position 163 of the wild-type protein appears at position 162 or 164 in the mutant. Moreover, to the extent that intervening residues are required to maintain the approximate distance between the critical receptor binding residues, one can construct the mutated TALL-1 protein accordingly, such as by retaining additional wild-type sequence or by using conservative amino acid substitutions in the intervening residues that maintain the three-dimensional structure of the receptor binding site as disclosed herein. In a particularly preferred aspect, the TALL-1 antagonist protein comprises an amino acid sequence that differs from SEQ ID NO:2 by at least one additional modification (i.e., in addition to the modification to decrease biological activity) that increases the binding affinity between the TALL-1 antagonist protein and a TALL-1 receptor, as compared to the binding affinity between wild-type TALL-1 and said TALL-1 receptor. Such modifications are preferably made at one or more of the following positions with respect to SEQ ID NO:2: Tyr163, Tyr206, Leu211, Arg231, Ile233, Pro264, Arg265, Glu266, Leu200, Leu240, Asp273, Asp275, Glu238 and Asp222. The modifications can include deletions, derivatizations, and/or substitutions of amino acids and/or insertion of non-natural amino acids effective to achieve the desired result, as discussed above. Modifications are made to at least one residue, but can be made to two, three, four, or any additional number of the above-identified residues, up to all of these residues.

In yet another embodiment, a TALL-1 antagonist protein that has reduced biological activity as compared to a wild-type TALL-1 protein includes a protein that comprises an amino acid sequence that differs from SEQ ID NO:2 by at least one modification that reduces interaction between a first trimer and a second trimer. As discussed above, TALL-1 monomers form trimers and the present inventors have shown that these trimers interact to form viral-like clusters that are believed to represent the biologically active form of TALL-1 in vivo. Reduction of the ability of the TALL-1 monomers to participate in trimer-trimer interactions will therefore reduce the biological activity of the protein. In addition to the "flap" region discussed above, the present inventors have identified many other residues in TALL-1 that are involved in the trimer-trimer associations (see Examples). An antagonist TALL-1 protein according to this embodiment may form trimers with any other TALL-1 monomers, including wild-type TALL-1 monomers and other TALL-1 homologue monomers (the same or different than the reference monomer), and the trimers can be homotrimers (formed of monomers of all the same type) or heterotrimers (formed of monomers of different types, such as two wild-type monomers with one antagonist monomer). In one aspect, this antagonist may also have a reduced ability to form trimers with other TALL-1 monomers (wild-type or homologues).

In one aspect of this embodiment of the invention, the TALL-1 antagonist protein comprises an amino acid sequence that differs from SEQ ID NO:2 by a modification in at least one amino acid residue located in a region of TALL-1 selected from the group consisting of β strand C, β strand F, and the region connecting β strand D to fβ strand E. In another aspect, the antagonist comprises an amino acid sequence that differs from SEQ ID NO:2 by a modification in at least one amino acid residue selected from: Ile150, Leu169, Phe172, Tyr192, Lys216, Val217, His218, Val219, Phe220, Gly221, Asp222, Glu223, Leu224, Val227, Leu229, Ile250, Lys252, and Glu254. In further embodiments, any number of residues greater than one and up to all of these residues can be modified. In one aspect, the antagonist comprises an amino acid sequence that differs from SEQ ID NO:2 by a modification in at least one amino acid residue selected from: Val217, His218, Val219, Phe220, Gly221, Asp222, Glu223, and Leu224. In another aspect, the antagonist comprises an amino acid sequence that differs from SEQ ID NO:2 by a modification in at least one amino acid residue selected from the group consisting of: Tyr192, Lys252, Glu254, His218, Lys216, Glu223, Leu224, Val227, Leu229, Val219, Ile150, Leu169, Phe220, Tyr192, Ile250 and Phe172. In another embodiment, the antagonist comprises an amino acid sequence that differs from SEQ ID NO:2 by a modification in at least one amino acid residue selected from the group consisting of: Tyr192, Lys252, Glu254, and His218. In yet another embodiment, the antagonist comprises an amino acid sequence that differs from SEQ ID NO:2 by a modification in at least one amino acid residue selected from the group consisting of: Lys216, Glu223, Leu224, Val227, and Leu229. In yet another embodiment, the antagonist comprises an amino acid sequence that differs from SEQ ID NO:2 by a modification in at least one amino acid residue selected from the group consisting of: Val219, Ile150, Leu169, Phe220, Tyr192, Ile250 and Phe172.

As described above for modifications to the flap region, the modified amino acid residues can be deleted, derivatized to reduce the ability of the residues to interact with residues on other TALL-1 monomers as described herein for the trimer-trimer associations, or substituted with non-natural amino acid residues that reduce the ability of the homologue to interact with residues on other TALL-1 monomers as described herein for the trimer-trimer associations. In addition, one or more non-natural amino acid residues can be inserted to replace one or more (not necessarily an equivalent number) of deleted residues in the homologue sequence. Modifications are made to at least one residue, but can be made to two, three, four, or any additional number of the above-identified residues, up to all of these residues.

Preferably, this TALL-1 antagonist protein binds to a TALL-1 receptor, including, but not limited to, BCMA, BAFF-R and TACI. In a more preferred embodiment, the TALL-1 antagonist comprises an amino acid sequence that differs from SEQ ID NO:2 by at least one additional modification that increases the binding affinity between the TALL-1 antagonist protein and a TALL-1 receptor, as compared to the binding affinity between wild-type TALL-1 and the TALL-1 receptor. For example, as discussed above, the TALL-1 antagonist can comprise an amino acid sequence that differs from SEQ ID NO:2 by an additional modification in at least one amino acid residue selected from the group consisting of: Tyr163, Tyr206, Leu211, Arg231, Ile233, Pro264, Arg265, Glu266, Leu200, Leu240, Asp273, Asp275, Glu238 and Asp222, where the additional modification increases the binding affinity between the TALL-1 antagonist protein and a TALL-1 receptor, as compared to the binding affinity between wild-type TALL-1 and the TALL-1 receptor. Modifications are made to at least one residue, but can be made to two, three, four, or any additional number of the above-identified residues, up to all of these residues.

In another embodiment, a TALL-1 antagonist protein that has reduced biological activity as compared to a wild-type TALL-1 protein includes a protein that comprises an amino acid sequence that differs from SEQ ID NO:2 by a modification of at least one amino acid residue selected from the group consisting of: Phe194, Tyr196, Tyr246, Leu282, Gln144 and Leu285. According to the present invention, these residues have been identified by the present inventors as being associated with the ability of TALL-1 monomers to form trimers, which is generally agreed in the art to be necessary for TALL-1 activity. A TALL-1 antagonist that has a reduced, or even abolished ability to form trimers, preferably retains the ability to bind to a TALL-1 receptor. The present inventors have shown that TALL-1 and its receptor bind in mostly one to one ratio, although a second monomer from a TALL-1 trimer does contribute to the interaction. Therefore, although binding to a single receptor by a monomer may be less stable than binding of a TALL-1 trimer, it is believed that a TALL-1 antagonist according to this embodiment will be able to compete at least to some extent with wild-type TALL-1 for binding to a receptor and thereby act as a competitive inhibitor. Moreover, introduction into this TALL-1 antagonist of additional modifications that increase the binding of the antagonist to the receptor, as described previously herein, can increase the efficacy of this antagonist as an inhibitor. Therefore, in one aspect, this TALL-1 antagonist comprises an amino acid sequence that differs from SEQ ID NO:2 by at least one additional modification that increases the binding affinity between the TALL-1 antagonist protein and a TALL-1 receptor, as compared to the binding affinity between wild-type TALL-1 and the TALL-1 receptor, such residues including, but not limited to: Tyr163, Tyr206, Leu211, Arg231, Ile233, Pro264, Arg265, Glu266, Leu200, Leu240, Asp273, Asp275, Glu238 and Asp222, where the additional modification increases the binding affinity between the TALL-1 antagonist protein and a TALL-1 receptor, as compared to the binding affinity between wild-type TALL-1 and the TALL-1 receptor. The modifications can include deletions, derivatizations, and/or substitutions of amino acids and/or insertion of non-natural amino acids effective to achieve the desired result, as discussed above. Modifications are made to at least one residue, but can be made to two, three, four, or any additional number of the above-identified residues, up to all of these residues.

In yet another embodiment of the invention, a TALL-1 antagonist protein that has reduced biological activity as compared to a wild-type TALL-1 protein includes a protein that comprises an amino acid sequence that differs from SEQ ID NO:2 by a modification of at least one amino acid residue that reduces the biological activity of the antagonist protein as compared to a wild-type TALL-1, wherein the amino acid residue is selected from: Gln144, Ile150, Leu169, Phe172, Tyr192, Phe194, Tyr196, Lys216, Val217, His218, Val219, Phe220, Gly221, Asp222, Glu223, Leu224, Val227, Leu229, Tyr246, Ile250, Lys252, Glu254, Leu282, and Leu285. This antagonist further differs from SEQ ID NO:2 by a modification of at least one amino acid residue that increases the binding affinity between the TALL-1 antagonist protein and a TALL-1 receptor, as compared to the binding affinity between wild-type TALL-1 and the TALL-1 receptor, wherein the amino acid residue is selected from: Tyr163, Tyr206, Leu211, Arg231, Ile233, Pro264, Arg265, Glu266, Leu200, Leu240, Asp273, Asp275, Glu238 and Asp222. The modifications can include deletions, derivatizations, and/or substitutions of amino acids and/or insertion of non-natural amino acids effective to achieve the desired result, as discussed above. Modifications are made to at least one residue, but can be made to two, three, four, or any additional number of the above-identified residues, up to all of these residues.

Yet another embodiment of the present invention relates to a TALL-1 antagonist protein, that has a reduced ability to bind to a receptor for TALL-1, including but not limited to, BCMA, BAFF-R or TACI. In this embodiment, the TALL-1 antagonist may otherwise have substantially normal biological activity as compared to the wild-type TALL-1 protein, or may have reduced biological activity, using the modifications described above, although preferably, this TALL-1 antagonist retains the ability to form trimers and participate in trimer-trimer interactions. This TALL-1 antagonist is useful as an agent the binds to wild-type TALL-1 monomers and thus forms part of trimers and clusters that have a reduced ability to bind to TALL-1 receptors, by virtue of the modifications to the receptor-binding portion of the antagonist. This TALL-1 antagonist is likely to be most efficient if delivered to a cell such that the antagonist is expressed by a cell that also expresses wild-type TALL-1 monomers, such that the antagonist can readily form the "defective" trimers as the proteins are expressed by a cell. In this embodiment, a recombinant nucleic acid molecule encoding the antagonist is delivered to the cell so that the cell expresses the antagonist and so that the antagonist can assemble trimers with wild-type TALL-1 monomers. Alternatively, the TALL-1 antagonist can be delivered to a cell or site under conditions whereby TALL-1 trimers may not have formed the viral-like clusters described herein. Without being bound by theory, the present inventors believe that trimers of TALL-1, prior to assembly into clusters, are in equilibrium, so that a TALL-1 antagonist near such trimers could reassemble with the wild-type monomers during this equilibrium. Once the viral-like assembly forms, which can be driven by concentration of trimers at a site, for example, the clustered assembly is not believed to be in equilibrium but rather quite stable. Therefore, if trimers can be formed that incorporate the TALL-1 antagonist prior to cluster formation, the result would be stable clusters with overall reduced receptor binding capability, and thus reduced TALL-1 activity via reduced TALL-1 receptor activation.

In one aspect of this embodiment, the TALL-1 antagonist protein comprises an amino acid sequence that differs from SEQ ID NO:2 by a modification to at least one amino acid residue selected from: Tyr163, Tyr206, Leu211, Arg231, Ile233, Pro264, Arg265, Glu266, Leu200, Leu240, Asp273, Asp275, Glu238 and Asp222, wherein the TALL-1 antagonist protein has reduced binding to a receptor for TALL-1 as compared to wild-type TALL-1. In another aspect, the antagonist comprises an amino acid sequence that differs from SEQ ID NO:2 by a modification to at least one amino acid residue selected from: Tyr163, Leu211, Ile233, Pro264, and Leu200. In another aspect, the antagonist comprises an amino acid sequence that differs from SEQ ID NO:2 by a modification to at least one amino acid residue selected from the group consisting of: Tyr206 and Leu240. In yet another aspect, the antagonist comprises an amino acid sequence that differs from SEQ ID NO:2 by a modification to at least one amino acid residue selected from the group consisting of: Arg265, Glu266 and Glu238. In yet another aspect, the antagonist comprises an amino acid sequence that differs from SEQ ID NO:2 by a modification to at least one amino acid residue selected from the group consisting of: Asp222, Asp 273 and Asp275. In one embodiment, the TALL-1 antagonist has reduced ability to bind to at least two of BCMA, BAFF-R and TACI, and in another embodiment, has a reduced ability to bind to each of BCMA, BAFF-R and TACI. Given the knowledge provided herein of the common and different residues of TALL-1 that are used in receptor binding to at least BCMA and BAFF-R, design and selection of such an antagonist is predicted. The modifications can include deletions, derivatizations, and/or substitutions of amino acids and/or insertion of non-natural amino acids effective to achieve the desired result, as discussed above. Modifications are made to at least one residue, but can be made to two, three, four, or any additional number of the above-identified residues, up to all of these residues.

It is to be expressly understood that any and all of the above-identified amino acid regions and residues that are important for TALL-1 biological activity and receptor binding can also be modified to produce TALL-1 agonists. The modifications can include deletions, derivatizations, and/or substitutions of amino acids and/or insertion of non-natural amino acids effective to achieve the desired result, as discussed above. Modifications are made to at least one residue, but can be made to two, three, four, or any additional number of the above-identified residues, up to all of these residues. A TALL-1 agonist is a TALL-1 homologue (i.e., mutant) that is an agonist of the biological activity of a wild-type, or naturally occurring TALL-1 protein, as discussed above. A TALL-1 agonist is generally a TALL-1 homologue which comprises at least one amino acid modification as compared to a naturally occurring TALL-1 or is a portion of TALL-1 that contains the modification, wherein the result is a homologue with TALL-1 activity or increased activity. The modifications to the amino acid sequence of the mutant TALL-1 can include any of the modifications to any amino acid position corresponding to any of the target residues identified herein based on the determination of the structure of TALL-1. In one embodiment of the invention, an agonist TALL-1 protein is disclosed that has an amino acid sequence comprising at least one modification as compared to a naturally occurring TALL-1, wherein the modification is in a region selected from: (1) the "flap" region of TALL-1 (discussed in detail below); (2) a region other than the "flap" that participates in trimer-trimer associations or "clustering" of TALL-1 trimers; (3) a region that is involved in formation of TALL-1 trimers; and/or (4) a region of TALL-1 that is associated with binding to a TALL-1 receptor (e.g., BCMA, BAFF-R or TACI). In contrast to TALL-1 antagonists, TALL-1 agonists with modifications in these regions have the same or increased ability to form trimers or to participate in trimer-trimer interactions, and/or have the same or increased ability to activate TALL-1 receptors, as compared to a wild-type TALL-1 protein. In addition, TALL-1 agonists can bind to TALL-1 receptors and can have increased binding to TALL-1 receptors as compared to the wild-type protein. Specific regions of TALL-1 and amino acid residues that are associated with each of these functions are described in detail in the Examples section.

Another embodiment of the present invention relates to an APRIL agonist protein. As discussed above, the present inventors, without being bound by theory, believe that APRIL may be serving as a decoy ligand, reducing the opportunity for sTALL-1 to bind to the same receptor. This role is similar to the decoy death receptors, which are essential for cells to survive. Therefore, agonists of APRIL, as well as wild-type APRIL itself, can effectively serve as TALL-1 antagonists according to the present invention. Therefore, the invention contemplates the production of homologues of APRIL which retain the biological activity of APRIL and which preferably bind to APRIL receptors (two of which are shared by TALL-1-BCMA and TACI). In a more preferred embodiment, the APRIL agonist has an increased ability to bind to an APRIL or TALL-1 receptor, and in another preferred embodiment, the receptor binding site of APRIL is modified so that APRIL binds to TALL-1 receptor such as BAFF-R (see Example 6). In one embodiment, the APRIL agonist protein comprises an amino acid sequence that differs from SEQ ID NO:4 by at least one modification that increases the binding affinity between the APRIL agonist protein and an APRIL receptor, as compared to the binding affinity between wild-type APRIL and the APRIL receptor. For example, in one aspect, such an agonist comprises an amino acid sequence that differs from SEQ ID NO:4 by a modification in at least one amino acid residue selected from: Val133, Thr177, Val181, Ile197, Pro230, Leu58, Tyr96, Phe176, Arg206, and Arg265, where the modification increases the binding affinity between the APRIL agonist protein and an APRIL receptor, as compared to the binding affinity between wild-type APRIL and the APRIL receptor. The modifications can include deletions, derivatizations, and/or substitutions of amino acids and/or insertion of non-natural amino acids effective to achieve the desired result, as discussed above. Modifications are made to at least one residue, but can be made to two, three, four, or any additional number of the above-identified residues, up to all of these residues.

In another embodiment, APRIL antagonists are contemplated. APRIL antagonists can have any one or more of the modifications in preferred amino acid residues, or in the regions surrounding these residues as described above for APRIL agonists, except the selected result is a modification that provides a homologue with biological activity that is antagonistic to the biological activity of wild-type APRIL.

Another embodiment of the present invention relates to antagonists of TALL-1 receptors, including antagonists of BCMA and/or BAFF-R, as well as antagonists of TACI. A TALL-1 receptor antagonist is a TALL-1 receptor homologue (i.e., mutant) that antagonizes the biological activity of a wild-type, or naturally occurring TALL-1 receptor, as discussed above. A TALL-1 receptor antagonist is generally a TALL-1 receptor homologue which comprises at least one amino acid modification as compared to a naturally occurring TALL-1 receptor or is a portion of a TALL-1 receptor that contains the modification. The modifications to the amino acid sequence of the mutant TALL-1 receptor can include any of the modifications to any amino acid position corresponding to any of the target residues identified herein based on the determination of the structure of the extracellular domains of the TALL-1 receptors BCMA and BAFF-R and can extend to TACI, given the amino acid similarity between BCMA and TACI and the prediction of similar structures. In one embodiment of the invention, an antagonist TALL-1 receptor protein is disclosed that has an amino acid sequence comprising at least one modification as compared to a naturally occurring TALL-1 receptor, wherein the modification is in a region that interacts with the natural ligand for the receptor (e.g., TALL-1 or APRIL). Specific regions of TALL-1 and amino acid residues that are associated with ligand binding are described in detail in the Examples section. In a preferred embodiment, the TALL-1 receptor antagonist is a soluble TALL-1 receptor, with the modifications to the amino acid sequence of the TALL-1 receptor, described herein. Soluble TALL-1 receptors, such as soluble BCMA, are described in detail in U.S. patent application Ser. No. 09/565,423 to Shu, incorporated herein by reference in its entirety.

In one aspect of this embodiment of the invention, the TALL-1 receptor antagonist is a BCMA antagonist, wherein the receptor antagonist comprises an amino acid sequence that differs from SEQ ID NO:6 by a modification in at least one amino acid residue selected from: Tyr13, Asp15, Leu17, Leu18, His19, Ile22, Leu26, Arg27, and Pro34, wherein the BCMA antagonist has an increased binding affinity for TALL-1 as compared to wild-type BCMA. In one aspect, the amino acid residue to be modified is selected from Leu17 and Leu18. In another aspect, the amino acid residue to be modified is selected from Ile22 and Leu26. In another aspect, the amino acid residue to be modified is selected from Asp15, Arg27 and Tyr13. In yet another aspect, the amino acid residue to be modified is His19. In yet another aspect, the amino acid residue to be modified is selected Tyr13, Leu17, Leu18 and Ile22. In a preferred embodiment, any one or more of Tyr13, Leu17, Leu18 and Ile22 is substituted with any one of the amino acid residues selected from: Ile, Met, Phe or Tyr. In each of these embodiments, the receptor antagonist preferably has an increased affinity for a ligand of the receptor (e.g., TALL-1 or APRIL), so that the receptor can serve as a competitive inhibitor of the natural receptor (wild-type). In addition, to serve as an antagonist of the wild-type receptor, the antagonist should have reduced ability to induce a signal that is associated with activation of the wild-type receptor or preferably, the receptor antagonist should not be able to transduce a signal, such as in a soluble receptor.

In another embodiment, the TALL-1 receptor antagonist is a BCMA antagonist, wherein the receptor antagonist comprises an amino acid sequence that differs from SEQ ID NO:6 by a modification in at least one amino acid residue within 2-5 amino acid residues to either side of any of the above-identified amino acid residues, including the above-identified amino acid residues. The basic tertiary structure of the BCMA receptor (at least the ligand binding region) should be maintained, which can be readily accomplished given the detailed disclosure of the tertiary structure of eBCMA provided herein.

The modified amino acid residues can be deleted, derivatized to increase the ability of the residues to interact with residues on the receptor ligand (e.g., TALL-1 or APRIL), or substituted with non-natural amino acid residues that increase the ability of the homologue to interact with residues on the receptor ligand. In addition, one or more non-natural amino acid residues can be inserted to replace one or more (not necessarily an equivalent number) of deleted residues in the homologue sequence. Modifications are made to at least one residue, but can be made to two, three, four, or any additional number of the above-identified residues, up to all of these residues. Binding affinity for a receptor and ligand can be readily measured as described previously herein.

In another aspect, BCMA homologues are provided with altered binding to APRIL (agonists or antagonists). For example, given the information provided herein (see Example 6), one can produce BCMA homologues with a modification at His19 which has modified binding to APRIL.

In another aspect of this embodiment of the invention, the TALL-1 receptor antagonist is a BAFF-R antagonist, wherein the receptor antagonist comprises an amino acid sequence that differs from SEQ ID NO:8 by a modification in at least one amino acid residue selected from: Asp26, Leu28, Val29, Arg30, Val33, Leu37, Leu38, and Arg42, and Pro45, where the BAFF-R antagonist has an increased binding affinity for TALL-1 as compared to wild-type BAFF-R. In one aspect, the amino acid residue to be modified is selected from Leu28 and Val29. In another aspect, the amino acid residue to be modified is selected from Val33, Leu37, Leu38 and Pro45. In another aspect, the amino acid residue to be modified is selected from Asp26 and Arg 42. In yet another aspect, the amino acid residue to be modified is Arg30. In yet another aspect, the amino acid residue to be modified is selected from Leu28, Val29 and Val33. In another aspect, any one or more of amino acid residues selected from Leu28, Val29 and Val33 is substituted with any one of the following amino acid residues: Ile, Met, Phe or Tyr. In each of these embodiments, the receptor antagonist preferably has an increased affinity for a ligand of the receptor (e.g., TALL-1), so that the receptor can serve as a competitive inhibitor of the natural receptor (wild-type). In addition, to serve as an antagonist of the wild-type receptor, the antagonist should have reduced ability to induce a signal that is associated with activation of the wild-type receptor or preferably, the receptor antagonist should not be able to transduce a signal, such as in a soluble receptor.

In another embodiment, the TALL-1 receptor antagonist is a BAFF-R antagonist, wherein the receptor antagonist comprises an amino acid sequence that differs from SEQ ID NO:8 by a modification in at least one amino acid residue within 2-5 amino acid residues to either side of any of the above-identified amino acid residues, including the above-identified amino acid residues. The basic tertiary structure of the BAFF-R (at least the ligand binding region) should be maintained, which can be readily accomplished given the detailed disclosure of the tertiary structure of eBAFF-R provided herein.

In yet another embodiment, a TALL-1 receptor antagonist or agonist (depending on the referenced function of the homologue) of BAFF-R is produced which binds to APRIL. Using the guidance provided in Example 6, for example, one can modify one or more residues in BAFF-R to provide a homologue of BAFF-R that can bind to APRIL. Such residues include, but are not limited to, modification of residues 1-11 or 1-12 of SEQ ID NO:8; modification of Arg30; modification of His31; modification of Val29; and/or modification of Val33. Two mutants of BAFF-R with the ability to bind to APRIL at pH7.5 are described in Example 6 (i.e., (1) deletion of residues 1-11 and Arg30His and His31Arg; (2) deletion of residues 1-11 and Val29Leu and Val33Ile). Other modifications producing similar results will be apparent to those of skill in the art given the structural information for APRIL and BAFF-R provided herein.

The modified amino acid residues can be deleted, derivatized to increase the ability of the residues to interact with residues on the receptor ligand (e.g., TALL-1), or substituted with non-natural amino acid residues that increase the ability of the homologue to interact with residues on the receptor ligand. In addition, one or more non-natural amino acid residues can be inserted to replace one or more (not necessarily an equivalent number) of deleted residues in the homologue sequence. Modifications are made to at least one residue, but can be made to two, three, four, or any additional number of the above-identified residues, up to all of these residues. Binding affinity for a receptor and ligand can be readily measured as described previously herein.

It is to be expressly understood that any and all of the above-identified amino acid regions and residues that are important for TALL-1 receptor-ligand binding can also be modified to produce TALL-1 receptor agonists, if desired. Also, it is to be understood that, using the structural information disclosed herein, one can predict the corresponding residues of TACI that will interact with BCMA or APRIL, and design antagonists of this receptor.

Given the structural information provided herein, one of skill in the art will also be able to design polypeptides of TALL-1 or its receptors which fall within the scope of the embodiments described above and serve as agonists or antagonists of TALL-1 or its receptors. By way of example, yet another embodiment of the present invention relates to an isolated BAFF-R antagonist that consists essentially of the amino acid sequence represented herein by SEQ ID NO:9. Positions 2-26 of SEQ ID NO:9 correspond to amino acid positions 15-29 of SEQ ID NO:8, with the following substitutions. At position 2 of SEQ ID NO:9, a Ser is substituted for the Ala that occurs in BAFF-R (position 15 of SEQ ID NO:8); at position 16 of SEQ ID NO:9, a Leu is substituted for the Val that occurs in BAFF-R (position 29 of SEQ ID NO:8); and at position 19 of SEQ ID NO:9, an Ile is substituted for the Val that occurs in BAFF-R (position 33 of SEQ ID NO:8). Without being bound by theory, the present inventors believe that extension of amino acid side chains in the ligand binding region of the receptor will increase the affinity of the receptor homologue for the ligand.

Another embodiment of the invention relates to a regulatory peptide having the amino acid sequence of SEQ ID NO:10, which is a peptide from the flap region of TALL-1 disclosed herein.

Another embodiment of the invention relates to a regulatory peptide or a homologue thereof having the amino acid sequence of any one of SEQ ID NO:11-SEQ ID NO:16. These sequences are illustrated in FIG. 8B and show the strong pattern of similarity between BCMA (SEQ ID NO:11), BAFF-R (SEQ ID NO:12), TACI1 (SEQ ID NO:13), TACI2 (SEQ ID NO:14), Fn14 (SEQ ID NO:15), and TNF-R1 (SEQ ID NO:16). Shown in FIG. 8B are residues (colored red) that are believed to be conserved disulfide bridges or pseudo disulfide bridges, which builds up module A1, D2, and D0. Residues colored yellow are not defined. Residues colored blue are for the C2 module. Residues colored green are putative residues involved in ligand recognition. Any of these residues, and particularly those that are at or near positions of defined proposed function (e.g., the green residues that are proposed to be involved in ligand recognition), can be targeted for modification in any of these proteins to produce novel homologues of the specified protein with altered biological activity and ligand binding, as described herein in detail for BCMA and BAFF-R.

Another embodiment of the invention relates to a homologue of any of TACI1, TACI2, Fn14, and TNF-R1, wherein the amino acid sequence of the homologue differs from the amino acid sequence of the wild type modifications (the wild-type protein comprising the amino acid sequence shown in SEQ ID NOs:13-16, respectively) by at least one modification to at least one amino acid residue that modifies the biological activity of the protein. In a preferred embodiment, modifications are made to any of the amino acid positions that are associated with the binding of the receptor to its ligand, as identified herein (see FIG. 8). For example, a TACI receptor can be modified at amino acid positions 39, 41, 43, 52 or 53 of the wild-type protein (TACI1; FIG. 8; corresponding to positions 6, 8, 10, 19 and 20 of SEQ ID NO:13, respectively) or at positions 78, 80, 82, 91 or 92 of the wild-type protein (TACI2; FIG. 8; corresponding to positions 8, 10, 12, 21 and 22 of SEQ ID NO:14, respectively). The complete nucleic acid sequence encoding TACI and the amino acid sequence therefore is provided in GenBank Accession No. AF023614, incorporated herein by reference in its entirety. The complete nucleic acid sequence encoding Fn14 and the amino acid sequence therefore is provided in GenBank Accession No. NM_016639, incorporated herein by reference in its entirety. The complete nucleic acid sequence encoding TNF-R1 and the amino acid sequence therefore is provided in GenBank Accession No. M75866, incorporated herein by reference in its entirety.

Another embodiment of the present invention relates to a fusion protein comprising any of the heretofore described proteins and homologues attached to one or more fusion segments. Suitable fusion segments for use with the present invention include, but are not limited to, segments that can: enhance a protein's stability; provide other desirable biological activity (e.g., a therapeutic protein/peptide to be delivered to a site); and/or assist with the purification of a protein (e.g., by affinity chromatography). A suitable fusion segment can be a domain of any size that has the desired function (e.g., imparts increased stability, solubility, biological activity; and/or simplifies purification of a protein). Fusion segments can be joined to amino and/or carboxyl termini of the protein of interest (e.g., a TALL-1 homologue) and can be susceptible to cleavage in order to enable straight-forward recovery of protein of interest. Fusion proteins are preferably produced by culturing a recombinant cell transfected with a nucleic acid molecule that encodes a protein including the fusion segment attached to either the carboxyl and/or amino terminal end of the protein of interest.

Another embodiment of the present invention relates to an isolated nucleic acid molecule that encodes any of the proteins and homologues described herein. In accordance with the present invention, an isolated polynucleotide, or an isolated nucleic acid molecule, is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. An isolated nucleic acid molecule can include a gene or a portion of a gene (e.g., the regulatory region or promoter). An isolated nucleic acid molecule that includes a gene is not a fragment of a chromosome that includes such gene, but rather includes the coding region and regulatory regions associated with the gene, but no additional genes naturally found on the same chromosome. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. Preferably, an isolated nucleic acid molecule of the present invention is produced using recombinant DNA technology (e.g., polymerase chain reaction (PCR) amplification, cloning) or chemical synthesis. If the polynucleotide is an oligonucleotide, such as a probe or primer, the oligonucleotide preferably ranges from about 5 to about 50 or about 500 nucleotides, more preferably from about 10 to about 40 nucleotides, and most preferably from about 15 to about 40 nucleotides in length.

Isolated nucleic acid molecules can include coding regions and/or regulatory regions (e.g. promoters), and can include nucleic acid sequences that have been modified by nucleotide insertions, deletions, substitutions, and/or inversions in a manner to encode the various homologues of TALL-1, APRIL or the receptors described herein. An isolated nucleic acid molecule can include degeneracies. As used herein, nucleotide degeneracy refers to the phenomenon that one amino acid can be encoded by different nucleotide codons. Thus, the nucleic acid sequence of a nucleic acid molecule that encodes a protein of the present invention can vary due to degeneracies.

Preferably, an isolated nucleic acid molecule of the present invention is produced using recombinant DNA technology (e.g., polymerase chain reaction (PCR) amplification, cloning) or chemical synthesis. A nucleic acid molecule homologue can be produced using a number of methods known to those skilled in the art (see, for example, Sambrook et al., ibid.). For example, nucleic acid molecules can be modified using a variety of techniques including, but not limited to, classical mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid and/or by hybridization with a wild-type gene.

The minimum size of a nucleic acid molecule of the present invention is a size sufficient to encode a protein having the desired biological activity, or sufficient to form a probe or oligonucleotide primer that is capable of forming a stable hybrid with the complementary sequence of a nucleic acid molecule encoding the desired protein (e.g., under moderate, high or very high stringency conditions, and preferably under very high stringency conditions). As such, the size of a nucleic acid molecule of the present invention can be dependent on nucleic acid composition and percent homology or identity between the nucleic acid molecule and complementary sequence as well as upon hybridization conditions per se (e.g., temperature, salt concentration, and formamide concentration). The minimal size of a nucleic acid molecule that is used as an oligonucleotide primer or as a probe is typically at least about 12 to about 15 nucleotides in length if the nucleic acid molecules are GC-rich and at least about 15 to about 18 bases in length if they are AT-rich. There is no limit, other than a practical limit, on the maximal size of a nucleic acid molecule of the present invention, in that the nucleic acid molecule can include any functional portion of a protein-encoding sequence (e.g., a TALL-1 homologue-encoding sequence).

One embodiment of the present invention relates to a recombinant nucleic acid molecule which comprises the isolated nucleic acid molecule described above which is operatively linked to at least one transcription control sequence. More particularly, according to the present invention, a recombinant nucleic acid molecule typically comprises a recombinant vector and the isolated nucleic acid molecule as described herein. According to the present invention, a recombinant vector is an engineered (i.e., artificially produced) nucleic acid molecule that is used as a tool for manipulating a nucleic acid sequence of choice and/or for introducing such a nucleic acid sequence into a host cell. The recombinant vector is therefore suitable for use in cloning, sequencing, and/or otherwise manipulating the nucleic acid sequence of choice, such as by expressing and/or delivering the nucleic acid sequence of choice into a host cell to form a recombinant cell. Such a vector typically contains heterologous nucleic acid sequences, that is, nucleic acid sequences that are not naturally found adjacent to nucleic acid sequence to be cloned or delivered, although the vector can also contain regulatory nucleic acid sequences (e.g., promoters, untranslated regions) which are naturally found adjacent to nucleic acid sequences of the present invention or which are useful for expression of the nucleic acid molecules of the present invention (discussed in detail below). The vector can be either RNA or DNA, either prokaryotic or eukaryotic, and typically is a plasmid. The vector can be maintained as an extrachromosomal element (e.g., a plasmid) or it can be integrated into the chromosome of a recombinant host cell, although it is preferred if the vector remain separate from the genome for most applications of the invention. The entire vector can remain in place within a host cell, or under certain conditions, the plasmid DNA can be deleted, leaving behind the nucleic acid molecule of the present invention. An integrated nucleic acid molecule can be under chromosomal promoter control, under native or plasmid promoter control, or under a combination of several promoter controls. Single or multiple copies of the nucleic acid molecule can be integrated into the chromosome. A recombinant vector of the present invention can contain at least one selectable marker.

In one embodiment, a recombinant vector used in a recombinant nucleic acid molecule of the present invention is an expression vector. As used herein, the phrase "expression vector" is used to refer to a vector that is suitable for production of an encoded product (e.g., a protein of interest). In this embodiment, a nucleic acid sequence encoding the product to be produced (e.g., a TALL-1 homologue) is inserted into the recombinant vector to produce a recombinant nucleic acid molecule. The nucleic acid sequence encoding the protein to be produced is inserted into the vector in a manner that operatively links the nucleic acid sequence to regulatory sequences in the vector which enable the transcription and translation of the nucleic acid sequence within the recombinant host cell.

In another embodiment of the invention, the recombinant nucleic acid molecule comprises a viral vector. A viral vector includes an isolated nucleic acid molecule of the present invention integrated into a viral genome or portion thereof, in which the nucleic acid molecule is packaged in a viral coat that allows entrance of DNA into a cell. A number of viral vectors can be used, including, but not limited to, those based on alphaviruses, poxviruses, adenoviruses, herpesviruses, lentiviruses, adeno-associated viruses and retroviruses.

According to the present invention, the phrase "operatively linked" refers to linking a nucleic acid molecule to a transcription control sequence in a manner such that the molecule is able to be expressed when transfected (i.e., transformed, transduced, transfected, conjugated or conduced) into a host cell. Transcription control sequences are sequences which control the initiation, elongation, or termination of transcription. Particularly important transcription control sequences are those which control transcription initiation, such as promoter, enhancer, operator and repressor sequences. Suitable transcription control sequences include any transcription control sequence that can function in a host cell or organism into which the recombinant nucleic acid molecule is to be introduced.

Recombinant nucleic acid molecules of the present invention can also contain additional regulatory sequences, such as translation regulatory sequences, origins of replication, and other regulatory sequences that are compatible with the recombinant cell. In one embodiment, a recombinant molecule of the present invention, including those which are integrated into the host cell chromosome, also contains secretory signals (i.e., signal segment nucleic acid sequences) to enable an expressed protein to be secreted from the cell that produces the protein. Suitable signal segments include a signal segment that is naturally associated with the protein to be expressed or any heterologous signal segment capable of directing the secretion of the protein according to the present invention. In another embodiment, a recombinant molecule of the present invention comprises a leader sequence to enable an expressed protein to be delivered to and inserted into the membrane of a host cell. Suitable leader sequences include a leader sequence that is naturally associated with the protein, or any heterologous leader sequence capable of directing the delivery and insertion of the protein to the membrane of a cell.

According to the present invention, the term "transfection" is used to refer to any method by which an exogenous nucleic acid molecule (i.e., a recombinant nucleic acid molecule) can be inserted into a cell. The term "transformation" can be used interchangeably with the term "transfection" when such term is used to refer to the introduction of nucleic acid molecules into microbial cells or plants. In microbial systems, the term "transformation" is used to describe an inherited change due to the acquisition of exogenous nucleic acids by the microorganism and is essentially synonymous with the term "transfection." However, in animal cells, transformation has acquired a second meaning which can refer to changes in the growth properties of cells in culture after they become cancerous, for example. Therefore, to avoid confusion, the term "transfection" is preferably used with regard to the introduction of exogenous nucleic acids into animal cells, and is used herein to generally encompass transfection of animal cells and transformation of plant cells and microbial cells, to the extent that the terms pertain to the introduction of exogenous nucleic acids into a cell. Therefore, transfection techniques include, but are not limited to, transformation, particle bombardment, electroporation, microinjection, lipofection, adsorption, infection and protoplast fusion.

One or more recombinant molecules of the present invention can be used to produce an encoded product (e.g., a TALL-1 antagonist protein, including fusion proteins) of the present invention. In one embodiment, an encoded product is produced by expressing a nucleic acid molecule as described herein under conditions effective to produce the protein. A preferred method to produce an encoded protein is by transfecting a host cell with one or more recombinant molecules to form a recombinant cell. Suitable host cells to transfect include, but are not limited to, any bacterial, fungal (e.g., yeast), insect, plant or animal cell that can be transfected. Host cells can be either untransfected cells or cells that are already transfected with at least one other recombinant nucleic acid molecule.

In one embodiment, one or more protein(s) expressed by an isolated nucleic acid molecule of the present invention are produced by culturing a cell that expresses the protein (i.e., a recombinant cell or recombinant host cell) under conditions effective to produce the protein. In some instances, the protein may be recovered, and in others, the cell may be harvested in whole (e.g., for ex vivo administration), either of which can be used in a composition. A preferred cell to culture is any suitable host cell as described above. Effective culture conditions include, but are not limited to, effective media, bioreactor, temperature, pH and oxygen conditions that permit protein production and/or recombination. An effective medium refers to any medium in which a given host cell is typically cultured. Such medium typically comprises an aqueous medium having assimilable carbon, nitrogen and phosphate sources, and appropriate salts, minerals, metals and other nutrients, such as vitamins. Cells can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant proteins of the present invention may either remain within the recombinant cell; be secreted into the culture medium; be secreted into a space between two cellular membranes; or be retained on the outer surface of a cell membrane. The phrase "recovering the protein" refers to collecting the whole culture medium containing the protein and need not imply additional steps of separation or purification. Proteins produced according to the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

Another embodiment of the present invention relates to compositions comprising any of the proteins (including homologues) and/or nucleic acid molecules described herein, or any of the compounds identified by drug design/selection using the structures of the present invention, which are useful for screening or therapeutic purposes. Such a composition of the present invention can include any carrier with which the protein, nucleic acid molecule or compound is associated by virtue of the protein, nucleic acid molecule or compound preparation method, a purification method, or a preparation of the protein, nucleic acid molecule or compound for use in an in vitro, ex vivo, or in vivo method according to the present invention. For example, such a carrier can include any suitable excipient, buffer and/or delivery vehicle, such as a pharmaceutically acceptable carrier (discussed below), which is suitable for combining with the protein, nucleic acid molecule or compound of the present invention so that the protein, nucleic acid molecule or compound can be used in vitro, ex vivo or in vivo according to the present invention.

The composition typically also includes a pharmaceutically acceptable carrier. According to the present invention, a "pharmaceutically acceptable carrier" includes pharmaceutically acceptable excipients and/or pharmaceutically acceptable delivery vehicles, which are suitable for use in administration of the composition to a suitable in vitro, ex vivo or in vivo site. A suitable in vitro, in vivo or ex vivo site is preferably a monocyte or macrophage, when TALL-1 is the target molecule (i.e., the molecule which is to be regulated or otherwise targeted by the composition), and a B lymphocyte, when a TALL-1 receptor is the target. In some embodiments, a suitable site for delivery is a site of interaction between B lymphocytes and monocytes or macrophages. Preferred pharmaceutically acceptable carriers are capable of maintaining a protein, compound, or recombinant nucleic acid molecule of the present invention in a form that, upon arrival of the protein, compound, or recombinant nucleic acid molecule at the cell target in a culture or in patient, the protein, compound or recombinant nucleic acid molecule is capable of interacting with its target (e.g., a naturally occurring TALL-1 protein, including membrane and/or soluble TALL-1 proteins, or a TALL-1 receptor).

Suitable excipients of the present invention include excipients or formularies that transport or help transport, but do not specifically target a composition to a cell (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Compositions of the present invention can be sterilized by conventional methods and/or lyophilized.

One type of pharmaceutically acceptable carrier includes a controlled release formulation that is capable of slowly releasing a composition of the present invention into a patient or culture. As used herein, a controlled release formulation comprises a compound of the present invention (e.g., a protein (including homologues), an antibody, a nucleic acid molecule, or a mimetic) in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposheres, and transdermal delivery systems. Other carriers of the present invention include liquids that, upon administration to a patient, form a solid or a gel in situ. Preferred carriers are also biodegradable (i.e., bioerodible). When the compound is a recombinant nucleic acid molecule, suitable delivery vehicles include, but are not limited to liposomes, viral vectors or other delivery vehicles, including ribozymes. Natural lipid-containing delivery vehicles include cells and cellular membranes. Artificial lipid-containing delivery vehicles include liposomes and micelles. A delivery vehicle of the present invention can be modified to target to a particular site in a patient, thereby targeting and making use of a compound of the present invention at that site. Suitable modifications include manipulating the chemical formula of the lipid portion of the delivery vehicle and/or introducing into the vehicle a targeting agent capable of specifically targeting a delivery vehicle to a preferred site, for example, a preferred cell type. Other suitable delivery vehicles include gold particles, poly-L-lysine/DNA-molecular conjugates, and artificial chromosomes.

A pharmaceutically acceptable carrier which is capable of targeting is herein referred to as a "delivery vehicle." Delivery vehicles of the present invention are capable of delivering a composition of the present invention to a target site in a patient. A "target site" refers to a site in a patient to which one desires to deliver a composition. For example, a target site can be any cell which is targeted by direct injection or delivery using liposomes, viral vectors or other delivery vehicles, including ribozymes. Examples of delivery vehicles include, but are not limited to, artificial and natural lipid-containing delivery vehicles, viral vectors, and ribozymes. Natural lipid-containing delivery vehicles include cells and cellular membranes. Artificial lipid-containing delivery vehicles include liposomes and micelles. A delivery vehicle of the present invention can be modified to target to a particular site in a mammal, thereby targeting and making use of a compound of the present invention at that site. Suitable modifications include manipulating the chemical formula of the lipid portion of the delivery vehicle and/or introducing into the vehicle a compound capable of specifically targeting a delivery vehicle to a preferred site, for example, a preferred cell type. Specifically, targeting refers to causing a delivery vehicle to bind to a particular cell by the interaction of the compound in the vehicle to a molecule on the surface of the cell. Suitable targeting compounds include ligands capable of selectively (i.e., specifically) binding another molecule at a particular site. Examples of such ligands include antibodies, antigens, receptors and receptor ligands. Manipulating the chemical formula of the lipid portion of the delivery vehicle can modulate the extracellular or intracellular targeting of the delivery vehicle. For example, a chemical can be added to the lipid formula of a liposome that alters the charge of the lipid bilayer of the liposome so that the liposome fuses with particular cells having particular charge characteristics.

One preferred delivery vehicle of the present invention is a liposome. A liposome is capable of remaining stable in an animal for a sufficient amount of time to deliver a nucleic acid molecule described in the present invention to a preferred site in the animal. A liposome, according to the present invention, comprises a lipid composition that is capable of delivering a nucleic acid molecule described in the present invention to a particular, or selected, site in a patient. A liposome according to the present invention comprises a lipid composition that is capable of fusing with the plasma membrane of the targeted cell to deliver a nucleic acid molecule into a cell. Suitable liposomes for use with the present invention include any liposome. Preferred liposomes of the present invention include those liposomes commonly used in, for example, gene delivery methods known to those of skill in the art. More preferred liposomes comprise liposomes having a polycationic lipid composition and/or liposomes having a cholesterol backbone conjugated to polyethylene glycol. Complexing a liposome with a nucleic acid molecule of the present invention can be achieved using methods standard in the art.

Another preferred delivery vehicle comprises a viral vector. A viral vector includes an isolated nucleic acid molecule useful in the present invention, in which the nucleic acid molecules are packaged in a viral coat that allows entrance of DNA into a cell. A number of viral vectors can be used, including, but not limited to, those based on alphaviruses, poxviruses, adenoviruses, herpesviruses, lentiviruses, adeno-associated viruses and retroviruses.

The various agonists and antagonists described herein (including the TALL-1, APRIL and TALL-1 receptor agonists and antagonists described above and the products of drug design described below) can be used in various therapeutic methods to regulate the biological activity of TALL-1, APRIL, or a TALL-1 receptor. For example, one embodiment of the present invention relates to a method to inhibit TALL-1 biological activity in a mammal, comprising administering to the mammal the recombinant nucleic acid molecule encoding a TALL-1 antagonist protein as described herein, wherein the protein is expressed by a host cell in the mammal. In one aspect of this embodiment, where the TALL-1 antagonist protein has reduced biological activity as compared to wild-type TALL-1, the antagonist associates with wild-type TALL-1 monomers expressed by the cell to produce TALL-1 trimers containing the protein with reduced TALL-1 biological activity, as compared to a trimer of wild-type TALL-1 monomers. In another aspect, where the TALL-1 antagonist has reduced ability to bind to a TALL-1 receptor, the protein associates with wild-type TALL-1 monomers expressed by the cell to produce TALL-1 trimers containing the protein with reduced ability to bind to a TALL-1 receptor, as compared to a trimer of wild-type TALL-1 monomers.

Another embodiment relates to a method to inhibit TALL-1 biological activity in a mammal, comprising administering to the mammal any of the TALL-1 antagonist proteins described herein. Preferably, the protein is a competitive inhibitor of wild-type TALL-1 for binding to a TALL-1 receptor.

Another embodiment of the invention relates to a method to inhibit TALL-1 receptor biological activity in a mammal, comprising administering to the mammal a TALL-1 receptor antagonist as described herein. In this embodiment, the antagonist is preferably a competitive inhibitor of a wild-type TALL-1 receptor for binding to TALL-1, such as a modified soluble receptor.

Another embodiment of the invention relates to a method to inhibit the biological activity of TALL-1, comprising administering to a cell that expresses TALL-1 a recombinant nucleic acid molecule comprising a nucleic acid sequence encoding APRIL, or a biologically active fragment thereof. In this embodiment, a recombinant nucleic acid molecule encoding: wild-type APRIL (SEQ ID NO:4), a biologically active fragment thereof, or a homologue thereof, such as the APRIL agonist described herein, is administered to a cell and preferably, a cell that expresses TALL-1, or a cell near a site where TALL-1 acts, so that the APRIL protein can effectively act as an inhibitor of TALL-1 by binding to the receptor for TALL-1.

According to the present invention, the therapeutic methods of the present invention are primarily directed to the regulation of the biological activity of a target cell (i.e., a B lymphocyte, a monocyte or a macrophage) in a patient with the added, but not required, goal of providing some therapeutic benefit to a patient. Modulating the phenotype of a target cell in a patient in the absence of obtaining some therapeutic benefit is useful for the purposes of determining factors involved (or not involved) in a disease and preparing a patient to more beneficially receive another therapeutic composition. In a preferred embodiment, however, the methods of the present invention are directed to the modulation of the phenotype of a target cell which is useful in providing some therapeutic benefit to a patient. As such, a therapeutic benefit is not necessarily a cure for a particular disease or condition, but rather, preferably encompasses a result which can include alleviation of the disease or condition, elimination of the disease or condition, reduction of a symptom associated with the disease or condition, prevention or alleviation of a secondary disease or condition resulting from the occurrence of a primary disease or condition, and/or prevention of the disease or condition. As used herein, the phrase "protected from a disease" refers to reducing the symptoms of the disease; reducing the occurrence of the disease, and/or reducing the severity of the disease. Protecting a patient can refer to the ability of a therapeutic composition of the present invention, when administered to a patient, to prevent a disease from occurring and/or to cure or to treat the disease by alleviating disease symptoms, signs or causes. As such, to protect a patient from a disease includes both preventing disease occurrence (prophylactic treatment) and treating a patient that has a disease or that is experiencing initial symptoms or later stage symptoms of a disease (therapeutic treatment). In particular, protecting a patient from a disease or enhancing another therapy (e.g., vaccination) is accomplished by regulating the interaction between TALL-1 and TALL-1 receptor such that a beneficial effect is obtained. A beneficial effect can easily be assessed by one of ordinary skill in the art and/or by a trained clinician who is treating the patient. The term, "disease" refers to any deviation from the normal health of a mammal and includes a state when disease symptoms are present, as well as conditions in which a deviation (e.g., infection, gene mutation, genetic defect, etc.) has occurred, but symptoms are not yet manifested.

In one embodiment, by performing the method of the present invention, the interaction between TALL-1 and TALL-1 receptor is decreased (e.g., using a TALL-1 or TALL-1 receptor antagonist or an APRIL agonist), such a decrease being sufficient to downregulate B lymphocyte proliferation, activation and/or survival in a patient (or in a culture, if the method is performed in vitro or ex vivo). In one embodiment, when the target cell is an autoreactive B lymphocyte, typically, the patient has or is at risk of developing an autoimmune disease associated with the autoreactive B lymphocyte. Such autoimmune diseases can be any autoimmune disease, and particularly include, rheumatoid arthritis, systemic lupus erythematosus, insulin dependent diabetes mellitus, multiple sclerosis, myasthenia gravis, Grave's disease, autoimmune hemolytic anemia, autoimmune thrombocytopenia purpura, Goodpasture's syndrome, pemphigus vulgaris, acute rheumatic fever, post-streptococcal glomerulonephritis, or polyarteritis nodosa. The autoreactive B lymphocyte in such a patient, prior to the step of administering the composition of the present invention, generally has normal or enhanced proliferation, activation, and/or survival as compared to a B lymphocyte from a patient that does not have and is not at risk of developing the autoimmune disease.

Inhibition of the interaction between TALL-1 and TALL-1 receptor expressed by an autoreactive B lymphocyte can result in a reduction in the proliferation, activation and/or survival of the B lymphocyte, which can be detected as a change in: B lymphocyte cytokine production, a reduction in NFκB activation, a reduction in TRAF5, TRAF6, NIK, IKKα and IKKβ activation, a reduction in immunoglobulin maturation, a reduction in immunoglobulin production and secretion, a reduction in calcium mobilization, or a reduction in phosphorylation of signal transduction proteins. Preferably, inhibition of the interaction between TALL-1 and TALL-1 receptor in the B lymphocytes of the patient produces a result in the patient which includes, but is not limited to, decreased autoantibody production, decreased autoreactive B cell proliferation, decreased autoreactive B cell survival, and/or reduced destruction of autologous cells or tissues, as compared to any of these measurements prior to the conducting of the method of the present invention, or as compared to a patient with the disease who has not been administered the composition of the present invention.

In one embodiment, by performing the method of the present invention, the interaction between TALL-1 and TALL-receptor is increased (e.g., by using TALL-1 agonists), such an increase being sufficient to upregulate B lymphocyte proliferation, activation and/or survival in a patient (or in a culture, if the method is performed in vitro or ex vivo). In one embodiment, the target cell is a normal B lymphocyte (e.g., in a patient receiving a vaccination), an anergic B lymphocyte, or a B lymphocyte in a patient suffering from a suppressed humoral immune response (e.g., in an immune compromised patient). The B lymphocyte in such a patient, prior to the step of administering the composition of the present invention, generally has normal or reduced proliferation, activation, and/or survival as compared to a B lymphocyte from a normal individual, to a patient who is not immune compromised, or to a patient that does not have and is not at risk of developing the disease.

Increasing the interaction between TALL-1 and TALL-1 receptor expressed by a normal or suppressed B lymphocyte can result in an increase in the proliferation, activation and/or survival of the B lymphocyte, which can be detected as a change in: B lymphocyte cytokine production, an increase in NFκB activation, an increase in TRAF5, TRAF6, NIK, IKKα and IKKβ activation, an increase in immunoglobulin maturation, an increase in immunoglobulin production and secretion, an increase in calcium mobilization, and/or an increase in phosphorylation of intracellular signal transduction proteins. Preferably, increasing the interaction between TALL-1 and TALL-1 receptor in the B lymphocytes of the patient produces a result in the patient which includes, but is not limited to, increased antibody production, increased B cell proliferation, and increased B cell survival, as compared to any of these measurements prior to the conducting of the method of the present invention, or as compared to a patient with the disease who has not been administered the composition of the present invention.

More specifically, a therapeutic composition as described herein, when administered to a patient by the method of the present invention, preferably produces a result which can include alleviation of the disease (e.g., reduction of at least one symptom or clinical manifestation of the disease), elimination of the disease, reduction in inflammation associated with the disease, increased clearance of infectious organisms associated with the disease, reduction of a tumor or lesion associated with the disease, elimination of a tumor or lesion associated with the disease, prevention or alleviation of a secondary disease resulting from the occurrence of a primary disease, prevention of the disease, and initial control or induction of effector cell immunity and/or humoral immunity (i.e., adaptive immunity) against the disease.

According to the present invention, an effective administration protocol (i.e., administering a therapeutic composition in an effective manner) comprises suitable dose parameters and modes of administration that result in the desired effect in the patient (e.g., regulation of B cell proliferation, activation and/or survival), preferably so that the patient is protected from the disease (e.g., by disease prevention or by alleviating one or more symptoms of ongoing disease). Effective dose parameters can be determined using methods standard in the art for a particular disease. Such methods include, for example, determination of survival rates, side effects (i.e., toxicity) and progression or regression of disease.

In accordance with the present invention, a suitable single dose size is a dose that results in regulation of B lymphocyte proliferation, activation and/or survival in a patient, or in the amelioration of at least one symptom of a condition in the patient, when administered one or more times over a suitable time period. Doses can vary depending upon the disease being treated. One of skill in the art can readily determine appropriate single dose sizes for a given patient based on the size of a patient and the route of administration. One of skill in the art can monitor the effectiveness of the treatment by measuring, for example, determination of survival rates, side effects (i.e., toxicity), determination of cellular and humoral immune response effects, and/or effects on conditions related to B lymphocyte proliferation, activation and/or survival, and symptoms associated with a specific disease or condition.

As discussed above, a therapeutic composition of the present invention is administered to a patient in a manner effective to deliver the composition to a cell, a tissue, and/or systemically to the patient, whereby the desired result (e.g., regulation of B lymphocyte proliferation, activation and/or survival) is achieved as a result of the administration of the composition. Suitable administration protocols include any in vivo or ex vivo administration protocol. The preferred routes of administration will be apparent to those of skill in the art, depending on the type of condition to be prevented or treated; whether the composition is nucleic acid based, protein based, or cell based; and/or the target cell/tissue. For proteins or nucleic acid molecules, preferred methods of in vivo administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, subcutaneous administration, intraarticular administration, intraventricular administration, inhalation (e.g., aerosol), intracranial, intraspinal, intraocular, intranasal, oral, bronchial, rectal, topical, vaginal, urethral, pulmonary administration, impregnation of a catheter, and direct injection into a tissue. Routes useful for deliver to mucosal tissues include, bronchial, intradermal, intramuscular, intranasal, other inhalatory, rectal, subcutaneous, topical, transdermal, vaginal and urethral routes. Combinations of routes of delivery can be used and in some instances, may enhance the therapeutic effects of the composition.

Ex vivo administration refers to performing part of the regulatory step outside of the patient, such as administering a composition (nucleic acid or protein) of the present invention to a population of cells removed from a patient under conditions such that the composition contacts and/or enters the cell, and returning the cells to the patient. Ex vivo methods are particularly suitable when the target cell type can easily be removed from and returned to the patient.

Many of the above-described routes of administration, including intravenous, intraperitoneal, intradermal, and intramuscular administrations can be performed using methods standard in the art. Aerosol (inhalation) delivery can also be performed using methods standard in the art (see, for example, Stribling et al., Proc. Natl. Acad. Sci. USA 189: 11277-11281, 1992, which is incorporated herein by reference in its entirety). Oral delivery can be performed by complexing a therapeutic composition of the present invention to a carrier capable of withstanding degradation by digestive enzymes in the gut of an animal. Examples of such carriers, include plastic capsules or tablets, such as those known in the art.

One method of local administration is by direct injection. Direct injection techniques are particularly useful for administering a composition to a cell or tissue that is accessible by surgery, and particularly, on or near the surface of the body.

Administration of a composition locally within the area of a target cell refers to injecting the composition centimeters and preferably, millimeters from the target cell or tissue.

Various methods of administration and delivery vehicles disclosed herein have been shown to be effective for delivery of a nucleic acid molecule to a target cell, whereby the nucleic acid molecule transfected the cell and was expressed. In many studies, successful delivery and expression of a heterologous gene was achieved in preferred cell types and/or using preferred delivery vehicles and routes of administration of the present invention. All of the publications discussed below and elsewhere herein with regard to gene delivery and delivery vehicles are incorporated herein by reference in their entirety.

For example, using liposome delivery, U.S. Pat. No. 5,705, 151, issued Jan. 6, 1998, to Dow et al. demonstrated the successful in vivo intravenous delivery of a nucleic acid molecule encoding a superantigen and a nucleic acid molecule encoding a cytokine in a cationic liposome delivery vehicle, whereby the encoded proteins were expressed in tissues of the animal, and particularly in pulmonary tissues. In addition, Liu et al., *Nature Biotechnology* 15:167, 1997, demonstrated that intravenous delivery of cholesterol-containing cationic liposomes containing genes preferentially targets pulmonary tissues and effectively mediates transfer and expression of the genes in vivo. Several publications by Dzau and collaborators demonstrate the successful in vivo delivery and expression of a gene into cells of the heart, including cardiac myocytes and fibroblasts and vascular smooth muscle cells using both naked DNA and Hemagglutinating virus of Japan-liposome delivery, administered by both incubation within the pericardium and infusion into a coronary artery (intracoronary delivery) (See, for example, Aoki et al., 1997, *J. Mol. Cell, Cardiol.* 29:949-959; Kaneda et al., 1997, *Ann N.Y. Acad. Sci.* 811: 299-308; and von der Leyen et al., 1995, *Proc Natl Acad Sci USA* 92:1137-1141).

Delivery of numerous nucleic acid sequences has been accomplished by administration of viral vectors encoding the nucleic acid sequences. Using such vectors, successful delivery and expression has been achieved using ex vivo delivery (See, of many examples, retroviral vector; Blaese et al., 1995, *Science* 270:475-480; Bordignon et al., 1995, *Science* 270: 470-475), nasal administration (CFTR-adenovirus-associated vector), intracoronary administration (adenoviral vector and Hemagglutinating virus of Japan, see above), intravenous administration (adeno-associated viral vector; Koeberl et al., 1997, *Proc Natl Acad Sci USA* 94:1426-1431). A publication by Maurice et al. (1999, *J. Clin. Invest.* 104:21-29) demonstrated that an adenoviral vector encoding a β2-adrenergic receptor, administered by intracoronary delivery, resulted in diffuse multichamber myocardial expression of the gene in vivo, and subsequent significant increases in hemodynamic function and other improved physiological parameters. Levine et al. describe in vitro, ex vivo and in vivo delivery and expression of a gene to human adipocytes and rabbit adipocytes using an adenoviral vector and direct injection of the constructs into adipose tissue (Levine et al., 1998, *J. Nutr. Sci. Vitaminol.* 44:569-572).

In the area of neuronal gene delivery, multiple successful in vivo gene transfers have been reported. Millecamps et al. reported the targeting of adenoviral vectors to neurons using neuron restrictive enhancer elements placed upstream of the promoter for the transgene (phosphoglycerate promoter). Such vectors were administered to mice and rats intramuscularly and intracerebrally, respectively, resulting in successful neuronal-specific transfection and expression of the transgene in vivo (Millecamps et al., 1999, *Nat. Biotechnol.* 17:865-869). As discussed above, Bennett et al. reported the use of adeno-associated viral vector to deliver and express a gene by subretinal injection in the neural retina in vivo for greater than 1 year (Bennett, 1999, ibid.).

Gene delivery to synovial lining cells and articular joints has had similar successes. Oligino and colleagues report the use of a herpes simplex viral vector which is deficient for the immediate early genes, ICP4, 22 and 27, to deliver and express two different receptors in synovial lining cells in vivo (Oligino et al., 1999, *Gene Ther.* 6:1713-1720). The herpes vectors were administered by intraarticular injection. Kuboki et al. used adenoviral vector-mediated gene transfer and intraarticular injection to successfully and specifically express a gene in the temporomandibular joints of guinea pigs in vivo (Kuboki et al., 1999, *Arch. Oral. Biol.* 44:701-709). Apparailly and colleagues systemically administered adenoviral vectors encoding IL-10 to mice and demonstrated successful expression of the gene product and profound therapeutic effects in the treatment of experimentally induced arthritis (Apparailly et al., 1998, *J. Immunol.* 160:5213-5220). In another study, murine leukemia virus-based retroviral vector was used to deliver (by intraarticular injection) and express a human growth hormone gene both ex vivo and in vivo (Ghivizzani et al., 1997, *Gene Ther.* 4:977-982). This study showed that expression by in vivo gene transfer was at least equivalent to that of the ex vivo gene transfer. As discussed above, Sawchuk et al. has reported successful in vivo adenoviral vector delivery of a gene by intraarticular injection, and prolonged expression of the gene in the synovium by pretreatment of the joint with anti-T cell receptor monoclonal antibody (Sawchuk et al., 1996, ibid. Finally, it is noted that ex vivo gene transfer of human interleukin-1 receptor antagonist using a retrovirus has produced high level intraarticular expression and therapeutic efficacy in treatment of arthritis, and is now entering FDA approved human gene therapy trials (Evans and Robbins, 1996, *Curr. Opin. Rheumatol.* 8:230-234). Therefore, the state of the art in gene therapy has led the FDA to consider human gene therapy an appropriate strategy for the treatment of at least arthritis. Taken together, all of the above studies in gene therapy indicate that delivery and expression of a recombinant nucleic acid molecule according to the present invention is feasible.

Another method of delivery of recombinant molecules is in a non-targeting carrier (e.g., as "naked" DNA molecules, such as is taught, for example in Wolff et al., 1990, *Science* 247, 1465-1468). Such recombinant nucleic acid molecules are typically injected by direct or intramuscular administration. Recombinant nucleic acid molecules to be administered by naked DNA administration include an isolated nucleic acid molecule of the present invention, and preferably includes a recombinant molecule of the present invention that preferably is replication, or otherwise amplification, competent. A naked nucleic acid reagent of the present invention can comprise one or more nucleic acid molecules of the present invention including a dicistronic recombinant molecule. Naked nucleic acid delivery can include intramuscular, subcutaneous, intradermal, transdermal, intranasal and oral routes of administration, with direct injection into the target tissue being most preferred. A preferred single dose of a naked nucleic acid vaccine ranges from about 1 nanogram (ng) to about 100 μg, depending on the route of administration and/or method of delivery, as can be determined by those skilled in the art. Suitable delivery methods include, for example, by injection, as drops, aerosolized and/or topically. In one embodiment, pure DNA constructs cover the surface of gold particles (1 to 3 μm in diameter) and are propelled into skin cells or muscle with a "gene gun."

In the method of the present invention, vaccines and therapeutic compositions can be administered to any member of the Vertebrate class, Mammalia, including, without limitation, primates, rodents, livestock and domestic pets. Livestock include mammals to be consumed or that produce useful products (e.g., sheep for wool production). Preferred mammals to protect include humans, dogs, cats, mice, rats, sheep, cattle, horses and pigs, with humans and dogs being particularly preferred, and humans being most preferred.

Conditions to treat using methods of the present invention include any condition, disease in which it is useful to modulate the activity of TALL-1 or its receptor(s). Such conditions include, but are not limited to, any condition in which B lymphocyte, monocyte or macrophage activity can be regulated to provide a therapeutic benefit and preferably, includes diseases characterized by hyperproliferation or hypoproliferation of B lymphocytes or hyperactive or hypoactive B cell development, and in one embodiment, diseases characterized by increased numbers of mature B-lymphocytes, splenomegaly, anti-DNA antibodies, proteinuria, or glomerulonephritis. Such conditions include autoimmune disease, such as rheumatoid arthritis, systemic lupus erythematosus, insulin dependent diabetes mellitus, multiple sclerosis, myasthenia gravis, Grave's disease, autoimmune hemolytic anemia, autoimmune thrombocytopenia purpura, Goodpasture's syndrome, pemphigus vulgaris, acute rheumatic fever, poststreptococcal glomerulonephritis, or polyarteritis nodosa. Such diseases also include conditions in which the target cell is a normal B lymphocyte (e.g., in a patient receiving a vaccination), an anergic B lymphocyte, or a B lymphocyte in a patient suffering from a suppressed humoral immune response (e.g., in an immune compromised patient).

Another embodiment of the present invention relates to a method to identify a compound that is a competitive inhibitor of TALL-1 binding to its receptor. The method includes the steps of (a) contacting a TALL-1 receptor or a TALL-1 binding fragment thereof with a homologue of a TALL-1 protein, wherein the homologue comprises an amino acid sequence with a modification in at least one amino acid residue selected from the group consisting of Tyr163, Tyr206, Leu211, Arg231, Ile233, Pro264, Arg265, Glu266, Leu200, Leu240, Asp273, Asp275, and Glu238; and (b) detecting whether the homologue binds to the TALL-1 receptor or fragment thereof. Homologues that bind to the TALL-1 receptor or fragment thereof potential competitive inhibitors for binding of wild-type TALL-1 to its receptor. The method can further include a step (c) of detecting whether homologues that bind to the TALL-1 receptor or fragment thereof in (b) have a TALL-1 biological activity selected from the group consisting of: an ability to activate signal transduction in the TALL-1 receptor, an ability to form a trimer with two other TALL-1 monomers, an ability to form a trimer with TALL-1 two other TALL-1 monomers that is capable of interacting with other TALL-1 trimers. Homologues that have a decreased TALL-1 biological activity as compared to wild-type TALL-1 are identified as TALL-1 antagonists, and wherein homologues that have an increased TALL-1 biological activity as compared to wild-type TALL-1 are identified as TALL-1 agonists. The method can also include in step (b) comparing the binding affinity the homologue to the TALL-1 receptor or fragment of thereof to the binding affinity of wild-type TALL-1 and the TALL-1 receptor, and a step (d) of selecting homologues which have an increased binding affinity to the TALL-1 receptor or fragment of and a decreased TALL-1 biological activity.

Such methods can include cell-free or a cell-based assays. Binding assays and assays for detecting biological activity have been described above. The step of contacting can be performed by any suitable method. For example, cells expressing a TALL-1 receptor can be grown in liquid culture medium or grown on solid medium in which the liquid medium or the solid medium contains the compound to be tested in the presence or absence of a wild-type TALL-1. In addition, as described above, the liquid or solid medium contains components necessary for cell growth, such as assimilable carbon, nitrogen and micro-nutrients. In another embodiment, the TALL-1 protein, homologue, and/or the TALL-1 receptor and/or cell lysates containing such proteins can be immobilized on a substrate such as: artificial membranes, organic supports, biopolymer supports and inorganic supports. The protein can be immobilized on the solid support by a variety of methods including adsorption, cross-linking (including covalent bonding), and entrapment. Adsorption can be through van del Waal's forces, hydrogen bonding, ionic bonding, or hydrophobic binding. Exemplary solid supports for adsorption immobilization include polymeric adsorbents and ion-exchange resins. Solid supports can be in any suitable form, including in a bead form, plate form, or well form.

The present invention also provides the atomic coordinates that define the three dimensional structure of a sTALL-1, alone and in complex with eBCMA and with eBAFF-R. First, the present inventors have determined the atomic coordinates that define the three dimensional structure of a crystalline TALL-1 (see Example 1 for details). Second, the present inventors have determined the atomic coordinates that define the three dimensional structure of a crystalline TALL-1 in complex with eBCMA (see Example 6 for details). Third, the present inventors have determined the atomic coordinates that define the three dimensional structure of a crystalline TALL-1 in complex with eBAFF-R (see Example 6 for details). Using the guidance provided herein, one of skill in the art will be able to reproduce any of such structures and define atomic coordinates of such a structure.

As used herein, a "structure" of a protein refers to the components and the manner of arrangement of the components to constitute the protein. The "three dimensional structure" or "tertiary structure" of the protein refers to the arrangement of the components of the protein in three dimensions. Such term is well known to those of skill in the art. It is also to be noted that the terms "tertiary" and "three dimensional" can be used interchangeably.

Example 1 describes the production of a sTALL-1, arranged in a crystalline manner in a space group P6$_3$22 so as to form a unit cell having approximate dimensions of a=b=234 Å, c=217 Å. The atomic coordinates determined from the crystal structure of TALL-1 are represented in Table 2. Table 2 represents the coordinates of a structure that has been refined to an R-factor of 23.6% ($R_{free}$-factor of 25.2%) against data extending to 3.0 Å resolution in space group P6$_3$22, with ten sTALL-1 monomers in the asymmetric unit cell having approximate dimensions of a=b=234 Å, c=217 Å. The atomic coordinates for the TALL-1 structure in Table 2 were deposited with the Protein Data Bank (PDB), operated by the Research Collaboratory for Structural Bioinformatics (RCSB) (H. M. Berman, J. Westbrook, Z. Feng, G. Gilliland, T. N. Bhat, H. Weissig, I. N. Shindyalov, P. E. Bourne, *The Protein Data Bank; Nucleic Acids Research*, 28:235-242 (2000)), under PDB Deposit No. 1JH5 in June 2001, and such coordinates are incorporated herein by reference and such coordinates are incorporated herein by reference.

Example 6 describes the production of a sTALL-1 complexed with eBMCA. The structure of sTALL-1 with eBCMA has been refined to an R-factor of 20.9% ($R_{free}$-factor of 23.4%) against data extending to 2.6 Å resolution in space group P6₃22, with ten sTALL-1 monomers and seven entire and one partial eBCMA molecules in the asymmetric unit cell having approximate dimensions of a=b=234 Å, c=217 Å (Table 1B). Due to crystal packing, another two receptor binding sites were left unoccupied. The attached tables of atomic coordinates labeled Tables 3-12 define the coordinates of 10 structures of sTALL-1 determined from 10 complexes of sTALL-1 and BCMA, and the tables of atomic coordinates labeled 13-22 define the coordinates of 10 structures of the extracellular domains of BCMA determined from the same complexes. Each structure of sTALL-1 is determined from the complex with one of the BCMA structures, such that Table 3 corresponds to Table 13, Table 4 corresponds to Table 14, and so on. By way of example, the structure of sTALL-1 represented by the atomic coordinates in Table 3 was determined from a complex of sTALL-1 and BCMA, wherein the structure of the BCMA is represented by the atomic coordinates in Table 13 (i.e., the structure represented by Table 3 was complexed with the structure represented by Table 13). Similarly, the structure of sTALL-1 represented by the atomic coordinates in Table 10 was determined from a complex of sTALL-1 and BCMA, wherein the structure of the BCMA is represented by the atomic coordinates in Table 20, and so on. The 10 different sTALL-1/BCMA complexes represented by the atomic coordinates provided herein are representative of the complexes which together, form the unique virus-like assembly described for TALL-1/receptor (Table 3-Table 13; Table 4-Table 14; Table 5-Table 15; Table 6-Table 16; Table 7-Table 17; Table 8-Table 18; Table 9-Table 19; Table 10-Table 20; Table 1'-Table 21; Table 12-Table 22).

Similar results are true for the sTALL-1 and eBAFF-R complex with a final resolution of 3.0 Å (Table 1B). The attached tables of atomic coordinates labeled Tables 23-32 define the coordinates of 10 structures of the extracellular domains of eBAFF-R determined from the complexes with sTALL-1. Together, the 10 different BAFF-R complexes represented by the atomic coordinates provided herein are representative of the structure of the receptor in the complex which together, form the unique virus-like assembly described for TALL-1/receptor.

One embodiment of the present invention includes a TALL-1, an eBMCA, or an eBAFF-R, in crystalline form. The present invention specifically exemplifies these crystalline forms. As used herein with regard to TALL-1 by way of example, the terms "crystalline TALL-1" and "TALL-1 crystal" both refer to crystallized TALL-1 and are intended to be used interchangeably. Preferably, a crystalline TALL-1 is produced using the crystal formation method described herein, in particular according to the method disclosed in Example 1. A TALL-1 crystal of the present invention can comprise any crystal structure that comes from crystals formed in any of the allowable space groups for proteins (61 of them) and in one embodiment, crystallizes as an orthorhombic crystal lattice. In one aspect, a crystalline TALL-1 of the present invention includes TALL-1 molecules arranged in a crystalline manner in a space group P6₃22, with ten sTALL-1 monomers in the asymmetric unit cell having approximate dimensions of a=b=234 Å, c=217 Å. According to the present invention, a unit cell having "approximate dimensions of" a given set of dimensions refers to a unit cell that has dimensions that are within plus (+) or minus (-) 2.0% of the specified unit cell dimensions. Such a small variation is within the scope of the invention since one of skill in the art could obtain such variance by performing X-ray crystallography at different times on the same crystal. A preferred crystal of the present invention provides X-ray diffraction data for determination of atomic coordinates of the TALL-1 crystal to a resolution of about 4.0 Å, and preferably to about 3.2 Å, and preferably to about 3.0 Å.

One embodiment of the present invention includes a method for producing crystals of TALL-1, TALL-1 in complex with its receptor, comprising combining the TALL-1 protein with a mother liquor and inducing crystal formation to produce the TALL-1 crystals. Although the production of crystals of TALL-1 is specifically described herein, it is to be understood that such processes as are described herein can be adapted by those of skill in the art to produce other crystals of TALL-1.

By way of example (i.e., this discussion applies to other crystals related to the invention, such as crystals of sTALL-1 and eBCMA or eBAFF-R), crystals of TALL-1 can be formed using a solution containing TALL-1 in a mother liquor. A suitable mother liquor of the present invention comprises the solution used for crystallization as described in Example 1 that causes the protein to crystallize. There is some tolerance in the mother liquor conditions so that changes of up to 30% in buffer concentrations, pH units, and temperatures can still yield crystals. Supersaturated solutions comprising TALL-1 can be induced to crystallize by several methods including, but not limited to, vapor diffusion, liquid diffusion, batch crystallization, constant temperature and temperature induction or a combination thereof. In one embodiment, supersaturated solutions of TALL-1 are induced to crystallize by hanging drop vapor diffusion. In a vapor diffusion method, TALL-1 molecule is combined with a mother liquor as described above that will cause the protein solution to become supersaturated and form crystals at a constant temperature. Vapor diffusion is preferably performed under a controlled temperature and, by way of example, can be performed at 18° C. In a preferred embodiment, crystals are formed using the methods described in detail in the Examples section.

The crystalline TALL-1 of the present invention is analyzed by X-ray diffraction and, based on data collected from this procedure, models are constructed which represent the tertiary structure of the TALL-1 monomers. Therefore, one embodiment of the present invention includes a representation, or model, such as a computer model, of the three dimensional structure of TALL-1, as a monomer, trimer, cluster, or in complex with a receptor. A computer model of the present invention can be produced using any suitable software modeling program, including, but not limited to, the graphical display program O (Jones et. al., *Acta Crystallography*, vol. A47, p. 110, 1991), the graphical display program GRASP, MOLSCRIPT 2.0 (Avatar Software AB, Heleneborgsgatan 21C, SE-11731 Stockholm, Sweden), the program CONTACTS from the CCP4 suite of programs (Bailey, 1994, *Acta Cryst. D*50:760-763), or the graphical display program INSIGHT. Suitable computer hardware useful for producing an image of the present invention are known to those of skill in the art (e.g., a Silicon Graphics Workstation).

A representation, or model, of the three dimensional structure of sTALL-1, eBCMA or eBAFF-R for which a crystal has been produced can also be determined using techniques which include molecular replacement or SIR/MIR (single/multiple isomorphous replacement), or MAD (multiple wavelength anomalous diffraction) methods (Hendrickson et al., 1997, *Methods Enzymol.*, 276:494-522). Methods of molecular replacement are generally known by those of skill in the art (generally described in Brunger, *Meth. Enzym.*, vol. 276, pp. 558-580, 1997; Navaza and Saludjian, *Meth. Enzym.*, vol. 276, pp. 581-594, 1997; Tong and Rossmann, *Meth. Enzym.*, vol. 276, pp. 594-611, 1997; and Bentley, *Meth. Enzym.*, vol. 276, pp. 611-619, 1997, each of which are incorporated by this reference herein in their entirety) and are performed in a software program including, for example, AmoRe (CCP4, *Acta Cryst.* D50, 760-763 (1994), SOLVE (Terwilliger et al., 1999, *Acta Crystallogr.*, D55:849-861), RESOLVE (Terwilliger, 2000, *Acta Crystallogr.*, D56:965-972) or XPLOR. Briefly, X-ray diffraction data is collected from the crystal of a crystallized target structure. The X-ray diffraction data is transformed to calculate a Patterson function. The Patterson function of the crystallized target structure is compared with a Patterson function calculated from a known structure (referred to herein as a search structure). The Patterson function of the crystallized target structure is rotated on the search structure Patterson function to determine the correct orientation of the crystallized target structure in the crystal. The translation function is then calculated to determine the location of the target structure with respect to the crystal axes. Once the crystallized target structure has been correctly positioned in the unit cell, initial phases for the experimental data can be calculated. These phases are necessary for calculation of an electron density map from which structural differences can be observed and for refinement of the structure. Preferably, the structural features (e.g., amino acid sequence, conserved di-sulphide bonds, and 1-strands or 1-sheets) of the search molecule are related to the crystallized target structure.

As used herein, the term "model" refers to a representation in a tangible medium of the three dimensional structure of a protein, polypeptide or peptide. For example, a model can be a representation of the three dimensional structure in an electronic file, on a computer screen, on a piece of paper (i.e., on a two dimensional medium), and/or as a ball-and-stick figure. Physical three-dimensional models are tangible and include, but are not limited to, stick models and space-filling models. The phrase "imaging the model on a computer screen" refers to the ability to express (or represent) and manipulate the model on a computer screen using appropriate computer hardware and software technology known to those skilled in the art. Such technology is available from a variety of sources including, for example, Evans and Sutherland, Salt Lake City, Utah, and Biosym Technologies, San Diego, Calif. The phrase "providing a picture of the model" refers to the ability to generate a "hard copy" of the model. Hard copies include both motion and still pictures. Computer screen images and pictures of the model can be visualized in a number of formats including space-filling representations, a carbon traces, ribbon diagrams and electron density maps. A variety of such representations of the sTALL-1, eBCMA or eBAFF-R structural model are shown, for example, in the figures of the invention.

Preferably, a three dimensional structure of sTALL-1 provided by the present invention includes:
  (a) atomic coordinates determined by X-ray diffraction of a crystalline TALL-1;
  (b) atomic coordinates selected from:
    (1) atomic coordinates represented in any one of Tables 2-12;
    (2) atomic coordinates that define a three dimensional structure having an average root-mean-square deviation (RMSD) of equal to or less than about 1.7 Å over the backbone atoms in secondary structure elements of at least 50% of the residues in a three dimensional structure represented by the atomic coordinates of (1); and
    (3) atomic coordinates in any one of Tables 2-12 defining a portion of the TALL-1, wherein the portion of the TALL-1 comprises sufficient structural information to perform step (b); and
  (c) atomic coordinates defining the three dimensional structure of TALL-1 molecules arranged in a crystalline manner in a space group $P6_322$ so as to form a unit cell having approximate dimensions of a=b=234 Å, c=217 Å.

Preferably, a three dimensional structure of BCMA or BAFF-R provided by the present invention includes:
  (a) atomic coordinates determined by X-ray diffraction of a crystalline BCMA or crystalline BAFF-R;
  (b) atomic coordinates selected from:
    (1) atomic coordinates represented in any one of Tables 13-33;
    (2) atomic coordinates that define a three dimensional structure having an average root-mean-square deviation (RMSD) of equal to or less than about 1.7 Å over the backbone atoms in secondary structure elements of at least 50% of the residues in a three dimensional structure represented by said atomic coordinates of (1); and
    (3) atomic coordinates in any one of Tables 13-22 defining a portion of said BCMA, wherein the portion of said BCMA comprises sufficient structural information to perform step (b);
    (4) atomic coordinates in any one of Tables 14-33 defining a portion of said BAFF-R, wherein the portion of said BAFF-R comprises sufficient structural information to perform step (b);
  (c) atomic coordinates defining the three dimensional structure of BCMA molecules or BAFF-R molecules arranged in a crystalline manner in a space group $P6_322$ so as to form a unit cell having approximate dimensions of a=b=234 Å, c=217.

In one aspect as described above, a three dimensional structure of sTALL-1, eBCMA or eBAFF-R provided by the present invention includes a structure wherein the structure has an average root-mean-square deviation (RMSD) of equal to or less than about 1.7 Å over the backbone atoms in secondary structure elements of at least 50% of the residues in a three dimensional structure represented by the atomic coordinates of any one of the referenced tables of atomic coordinates. Such a structure can be referred to as a structural homologue of the sTALL-1, eBCMA or eBAFF-R structures defined by one of the corresponding referenced tables of atomic coordinates. Preferably, the structure has an average root-mean-square deviation (RMSD) of equal to or less than about 1.6 Å over the backbone atoms in secondary structure elements of at least 50% of the residues in a three dimensional structure represented by the atomic coordinates of any one of the corresponding reference tables, or equal to or less than about 1.5 Å, or equal to or less than about 1.4 Å, or equal to or less than about 1.3 Å, or equal to or less than about 1.2 Å, or equal to or less than about 1.1 Å, or equal to or less than about 1.0 Å, or equal to or less than about 0.9 Å, or equal to or less than about 0.8 Å, or equal to or less than about 0.7 Å, or equal to or less than about 0.6 Å, or equal to or less than about 0.5 Å, or equal to or less than about 0.4 Å, or equal to or less than about 0.3 Å, or equal to or less than about 0.2 Å, over the backbone atoms in secondary structure elements of at least 50% of the residues in a three dimensional structure represented by the atomic coordinates of any one of the corresponding reference tables of atomic coordinates. In another aspect, a three dimensional structure of a sTALL-1, eBCMA or eBAFF-R provided by the present invention includes a structure wherein the structure has the recited RMSD over the backbone atoms in secondary structure elements of at least 75% of the residues in a three dimensional structure represented by the atomic coordinates of any one of the corresponding referenced tables of atomic coordinates, and more preferably at least about 80%, and more preferably at least about 85%, and more preferably at least about 90%, and more preferably at least about 95%, and most preferably, about 100% of the residues in a three dimensional structure represented by the atomic coordinates of any one of the corresponding referenced tables.

In one embodiment, the RMSD of a structural homologue of sTALL-1, eBCMA or eBAFF-R can be extended to include atoms of amino acid side chains. As used herein, the phrase "common amino acid side chains" refers to amino acid side chains that are common to both the structural homologue and to the structure that is actually represented by such atomic coordinates (e.g., a structure represented by one of the tables of atomic coordinates). Preferably, at least 50% of the structure has an average root-mean-square deviation (RMSD) from common amino acid side chains in a three dimensional structure represented by the atomic coordinates of one of the referenced tables of equal to or less than about 1.7 Å, or equal to or less than about 1.6 Å, equal to or less than about 1.5 Å, or equal to or less than about 1.4 Å, or equal to or less than about 1.3 Å, or equal to or less than about 1.2 Å, or equal to or less than about 1.3 Å, or equal to or less than about 1.0 Å, or equal to or less than about 0.9 Å, or equal to or less than about 0.8 Å, or equal to or less than about 0.7 Å, or equal to or less than about 0.6 Å, or equal to or less than about 0.5 Å, or equal to or less than about 0.4 Å, or equal to or less than about 0.3 Å, or equal to or less than about 0.2 Å. In another embodiment, a three dimensional structure of sTALL-1, eBCMA or eBAFF-R provided by the present invention includes a structure wherein at least about 75% of such structure has the recited average root-mean-square deviation (RMSD) value, and more preferably, at least about 85% of such structure has the recited average root-mean-square deviation (RMSD) value, and most preferably, about 95% of such structure has the recited average root-mean-square deviation (RMSD) value.

In addition to having the recited RMSD values, a structural homologue of sTALL-1, eBCMA or eBAFF-R should additionally meet the criteria for amino acid sequence identity which was discussed in detail previously herein. For a given amino acid sequence or amino acid residue to correspond to an amino acid region or amino acid position in another sequence, the position of the sequence or residue in the query sequence should align to the position of the region or residue in the compared sequence using a standard alignment program in the art, but particularly, using the programs BLOCKS (GIBBS) and/or MAST (Henikoff et al., 1995, *Gene,* 163, 17-26; Henikoff et al., 1994, *Genomics,* 19, 97-107), using standard manufacturer defaults.

Another structure that is useful in the methods of the present invention is a structure that is defined by the atomic coordinates in any one of the referenced tables of atomic coordinates that define a portion of the sTALL-1, eBCMA or eBAFF-R, wherein the portion of the sTALL-1, eBCMA or eBAFF-R comprises sufficient structural information to perform structure based drug design (described below). Suitable portions of sTALL-1, eBCMA or eBAFF-R that could be modeled and used in structure based drug design will be apparent to those of skill in the art. The present inventors have also identified multiple sites of interest based on the structure of sTALL-1, eBCMA or eBAFF-R (described in detail above and in the Examples). Structures comprising these portions (e.g., a receptor or ligand binding region) would be encompassed by the present invention.

Accordingly, another embodiment of the present invention relates to a method of structure-based identification of compounds which potentially bind to TALL-1. The method includes the steps of: (a) obtaining atomic coordinates that define the three dimensional structure of TALL-1 (described below); and (b) selecting candidate compounds for binding to the TALL-1 by performing structure based drug design with the structure of (a), wherein the step of selecting is performed in conjunction with computer modeling. The atomic coordinates used in the method are selected from:
  (i) atomic coordinates determined by X-ray diffraction of a crystalline TALL-1;
  (ii) atomic coordinates selected from:
    (1) atomic coordinates represented in any one of Tables 2-12;
    (2) atomic coordinates that define a three dimensional structure having an average root-mean-square deviation (RMSD) of equal to or less than about 1.7 Å over the backbone atoms in secondary structure elements of at least 50% of the residues in a three dimensional structure represented by the atomic coordinates of (1); and
    (3) atomic coordinates in any one of Tables 2-12 defining a portion of the TALL-1, wherein the portion of the TALL-1 comprises sufficient structural information to perform step (b); and
  (iii) atomic coordinates defining the three dimensional structure of TALL-1 molecules arranged in a crystalline manner in a space group $P6_322$ so as to form a unit cell having approximate dimensions of a=b=234 Å, c=217 Å.

In one embodiment, the method further comprises a step (c) of selecting candidate compounds of (b) that inhibit the biological activity of TALL-1. In one aspect, this step of selecting comprises (i) contacting the candidate compound identified in step (b) with TALL-1; and (ii) measuring the biological activity of the TALL-1, as compared to in the absence of the candidate compound.

In another embodiment, the method further comprises a step (c) of selecting candidate compounds of (b) that inhibit the binding of TALL-1 to a TALL-1 receptor. In this aspect, the step (c) can include: (i) contacting the candidate compound identified in step (b) with the TALL-1 or a fragment thereof and a TALL-1 receptor or TALL-1 receptor binding fragment thereof under conditions in which a TALL-1-TALL-1 receptor complex can form in the absence of the candidate compound; and (ii) measuring the binding of the TALL-1 or fragment thereof to bind to the TALL-1 receptor or fragment thereof, wherein a candidate inhibitor compound is selected when there is a decrease in the binding of the TALL-1 or fragment thereof to the TALL-1 receptor or fragment thereof, as compared to in the absence of the candidate inhibitor compound. A TALL-1 receptor used in these embodiments can include BCMA, BAFF-R and TACI.

In the general method, the step (b) of selecting can include identifying candidate compounds for binding to a receptor binding site of the TALL-1 protein, the receptor binding site comprising an amino acid residue selected from the group consisting of Tyr163, Tyr206, Leu211, Arg231, Ile233, Pro264, Arg265, Glu266, Leu200, Leu240, Asp273, Asp275, Glu238 and Asp222. In another aspect, step (b) of selecting comprises identifying candidate compounds for binding to the TALL-1 such that trimer-trimer interactions between trimers of TALL-1 monomers is inhibited. For example, the step of selecting can include identifying candidate compounds for binding to TALL-1 at a site including an amino acid residue selected from the group consisting of: Gln144, Ile150, Leu169, Phe172, Tyr192, Phe194, Tyr196, Lys216, Val217, His218, Val219, Phe220, Gly221, Asp222, Glu223, Leu224, Val227, Leu229, Tyr246, Ile250, Lys252, Glu254, Leu282, and Leu285.

Another embodiment of the present invention relates to a method to construct a three dimensional model of TALL-1 protein or homologue thereof. The method includes the steps of: (a) obtaining atomic coordinates that define the three dimensional structure of TALL-1; and (b) performing computer modeling with the atomic coordinates of (a) and to construct a model of a three dimensional structure of a TALL-1 or homologue thereof. the atomic coordinates are the same as those described above for the method of identifying compounds that bind to TALL-1.

Yet another embodiment of the present invention relates to a method of structure-based identification of compounds which potentially bind to a TALL-1 receptor selected from the group consisting of BCMA and BAFF-R, comprising: (a) obtaining atomic coordinates that define the three dimensional structure of BCMA or BAFF-R; and (b) selecting candidate compounds for binding to the BCMA or BAFF-R by performing structure based drug design with the structure of (a), wherein the step of selecting is performed in conjunction with computer modeling. The atomic coordinates used in the method are selected from:
(a) atomic coordinates determined by X-ray diffraction of a crystalline BCMA or crystalline BAFF-R;
(b) atomic coordinates selected from the group consisting of:
  (1) atomic coordinates represented in any one of Tables 13-33;
  (2) atomic coordinates that define a three dimensional structure having an average root-mean-square deviation (RMSD) of equal to or less than about 1.7 Å over the backbone atoms in secondary structure elements of at least 50% of the residues in a three dimensional structure represented by the atomic coordinates of (1);
  (3) atomic coordinates in any one of Tables 13-22 defining a portion of the BCMA, wherein the portion of the BCMA comprises sufficient structural information to perform step (b); and
  (4) atomic coordinates in any one of Tables 14-33 defining a portion of the BAFF-R, wherein the portion of the BAFF-R comprises sufficient structural information to perform step (b); and
(c) atomic coordinates defining the three dimensional structure of BCMA molecules or BAFF-R molecules arranged in a crystalline manner in a space group $P6_322$ so as to form a unit cell having approximate dimensions of a=b=234 Å, c=217.

Yet another embodiment of the present invention relates to a method to construct a three dimensional model of BCMA, BAFF-R, TACI, or a homologue thereof, comprising: (a) obtaining atomic coordinates that define the three dimensional structure of BCMA or BAFF-R (as described for the method above); and, (b) performing computer modeling with the atomic coordinates of (a) and an amino acid sequence corresponding to BCMA, BAFF-R or TACI to construct a model of a three dimensional structure of the BCMA, BAFF-R or TACI, or homologue thereof.

The structures and atomic coordinates used to perform the above-described method have been described in detail above and in the Examples section, and include any structural homologues of TALL-1 described herein or in other embodiments of drug design described below, any structural homologues of a TALL-1 receptor described herein. In general, terms and definitions used to describe this embodiment related to the method of structure-based identification of compounds which potentially bind to TALL-1 will apply to the other methods of structure-based identification of compounds that bind to a TALL-1 receptor, or to methods of designing compounds that mimic the structure of TALL-1 or TALL-1 receptors.

According to the present invention, the phrase "obtaining atomic coordinates that define the three dimensional structure of TALL-1" is defined as any means of obtaining providing, supplying, accessing, displaying, retrieving, or otherwise making available the atomic coordinates defining any three dimensional structure of TALL-1 as described herein. For example, the step of obtaining can include, but is not limited to, accessing the atomic coordinates for the structure from a database or other source; importing the atomic coordinates for the structure into a computer or other database; displaying the atomic coordinates and/or a model of the structure in any manner, such as on a computer, on paper, etc.; and determining the three dimensional structure of TALL-1 described by the present invention de novo using the guidance provided herein.

The second step of the method of structure based identification of compounds of the present invention includes selecting a candidate compound for binding to and/or inhibiting the biological activity of the TALL-1 represented by the structure model by performing structure based drug design with the model of the structure. According to the present invention, the step of "selecting" can refer to any screening process, modeling process, design process, or other process by which a compound can be selected as useful for binding to and enhancing or inhibiting the activity of TALL-1 according to the present invention. Methods of structure based identification of compounds are described in detail below. As discussed above, TALL-1 is involved in the regulation of B cell development, proliferation and survival, and therefore, the selection of compounds that compete with, disrupt or otherwise inhibit the biological activity of TALL-1 (or its receptors) are highly desirable. In addition, in some embodiments, compounds which enhance, increase, or otherwise agonize the biological activity of TALL-1 (or its receptors) may be desirable, such as in immunodeficiency diseases or vaccine administration. Any of such compounds can be designed using structure based drug design using models of the structures disclosed herein. Until the discovery of the three dimensional structure of the present invention, the only information available for the development of therapeutic compounds based on TALL-1 was based on the primary sequence of TALL-1 and perhaps, mutagenesis studies directed to the isolated protein.

Structure based identification of compounds (e.g., structure based drug design, structure based compound screening, or structure based structure modeling) refers to the prediction or design of a conformation of a peptide, polypeptide, protein (e.g., TALL-1), or to the prediction or design of a conformational interaction between such protein, peptide or polypeptide, and a candidate compound, by using the three dimensional structure of the peptide, polypeptide or protein. Typically, structure based identification of compounds is performed with a computer (e.g., computer-assisted drug design, screening or modeling). For example, generally, for a protein to effectively interact with (e.g., bind to) a compound, it is necessary that the three dimensional structure of the compound assume a compatible conformation that allows the compound to bind to the protein in such a manner that a desired result is obtained upon binding. Knowledge of the three dimensional structure of TALL-1 and two of its cognate receptors enables a skilled artisan to design a compound having such compatible conformation, or to select such a compound from available libraries of compounds and/or structures thereof. For example, knowledge of the three dimensional structure of the receptor binding site of TALL-1 or the ligand binding site of a TALL-1 receptor enables one of skill in the art to design or select a compound structure that is predicted to bind to the TALL-1 or its receptor at that site and result in, for example, inhibition of the binding of a wild-type TALL-1 to the receptor, thereby inhibiting a biological response such as activation of B cell proliferation or maturation. In addition, for example, knowledge of the three dimensional structure of TALL-1 enables a skilled artisan to design an analog (structural homologue) of TALL-1 or an analog of TALL-1 receptor.

Suitable structures and models useful for structure based drug design are disclosed herein. Preferred target structures to use in a method of structure based drug design include any representations of structures produced by any modeling method disclosed herein, including molecular replacement and fold recognition related methods.

According to the present invention, the step of selecting or designing a compound for testing in a method of structure based identification of the present invention can include creating a new chemical compound structure or searching databases of libraries of known compounds (e.g., a compound listed in a computational screening database containing three dimensional structures of known compounds). Designing can also be performed by simulating chemical compounds having substitute moieties at certain structural features. The step of designing can include selecting a chemical compound based on a known function of the compound. A preferred step of designing comprises computational screening of one or more databases of compounds in which the three dimensional structure of the compound is known and is interacted (e.g., docked, aligned, matched, interfaced) with the three dimensional structure of a TALL-1 protein or receptor by computer (e.g. as described by Humblet and Dunbar, *Animal Reports in Medicinal Chemistry*, vol. 28, pp. 275-283, 1993, M Venuti, ed., Academic Press). The compound itself, if identified as a suitable candidate by the method of the invention, can be synthesized and tested directly with the TALL-1 protein or a TALL-1 receptor in a biological assay. Methods to synthesize suitable chemical compounds are known to those of skill in the art and depend upon the structure of the chemical being synthesized. Methods to evaluate the bioactivity of the synthesized compound depend upon the bioactivity of the compound (e.g., inhibitory or stimulatory) and are discussed herein.

Various other methods of structure-based drug design are disclosed in Maulik et al., 1997, *Molecular Biotechnology: Therapeutic Applications and Strategies*, Wiley-Liss, Inc., which is incorporated herein by reference in its entirety. Maulik et al. disclose, for example, methods of directed design, in which the user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional receptor structures and small fragment probes, followed by linking together of favorable probe sites.

In a molecular diversity strategy, large compound libraries are synthesized, for example, from peptides, oligonucleotides, carbohydrates and/or synthetic organic molecules, using biological, enzymatic and/or chemical approaches. The critical parameters in developing a molecular diversity strategy include subunit diversity, molecular size, and library diversity. The general goal of screening such libraries is to utilize sequential application of combinatorial selection to obtain high-affinity ligands for a desired target, and then to optimize the lead molecules by either random or directed design strategies. Methods of molecular diversity are described in detail in Maulik, et al., ibid.

Maulik et al. also disclose, for example, methods of directed design, in which the user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional receptor structures and small fragment probes, followed by linking together of favorable probe sites.

In the present method of structure based identification of compounds, it is not necessary to align the structure of a candidate chemical compound (i.e., a chemical compound being analyzed in, for example, a computational screening method of the present invention) to each residue in a target site (target sites will be discussed in detail below). Suitable candidate chemical compounds can align to a subset of residues described for a target site. Preferably, a candidate chemical compound comprises a conformation that promotes the formation of covalent or noncovalent crosslinking between the target site and the candidate chemical compound. In one aspect, a candidate chemical compound binds to a surface adjacent to a target site to provide an additional site of interaction in a complex. When designing an antagonist (i.e., a chemical compound that inhibits the biological activity of an TALL-1), for example, the antagonist should bind with sufficient affinity to the target binding site or substantially prohibit a ligand (e.g., a molecule that specifically binds to the target site) from binding to a target site. It will be appreciated by one of skill in the art that it is not necessary that the complementarity between a candidate chemical compound and a target site extend over all residues specified here in order to inhibit or promote binding of a ligand.

In general, the design of a chemical compound possessing stereochemical complementarity can be accomplished by techniques that optimize, chemically or geometrically, the "fit" between a chemical compound and a target site. Such techniques are disclosed by, for example, Sheridan and Venkataraghavan, *Acc. Chem. Res.*, vol. 20, p. 322, 1987: Goodford, *J. Med. Chem.*, vol. 27, p. 557, 1984; Beddell, *Chem. Soc. Reviews*, vol. 279, 1985; Hol, *Angew. Chem.*, vol. 25, p. 767, 1986; and Verlinde and Hol, *Structure*, vol. 2, p. 577, 1994, each of which are incorporated by this reference herein in their entirety.

One embodiment of the present invention for structure based drug design comprises identifying a chemical compound that complements the shape of TALL-1 or a TALL-1 receptor, including a portion of TALL-1 or a TALL-1 receptor. Such method is referred to herein as a "geometric approach". In a geometric approach, the number of internal degrees of freedom (and the corresponding local minima in the molecular conformation space) is reduced by considering only the geometric (hard-sphere) interactions of two rigid bodies, where one body (the active site) contains "pockets" or "grooves" that form binding sites for the second body (the complementing molecule, such as a ligand).

The geometric approach is described by Kuntz et al., *J. Mol. Biol.*, vol. 161, p. 269, 1982, which is incorporated by this reference herein in its entirety. The algorithm for chemical compound design can be implemented using the software program DOCK Package, Version 1.0 (available from the Regents of the University of California). Pursuant to the Kuntz algorithm, the shape of the cavity or groove on the surface of a structure (e.g., TALL-1) at a binding site or interface is defined as a series of overlapping spheres of different radii. One or more extant databases of crystallographic data (e.g., the Cambridge Structural Database System maintained by University Chemical Laboratory, Cambridge University, Lensfield Road, Cambridge CB2 1EW, U.K.) or the Protein Data Bank maintained by Brookhaven National Laboratory, is then searched for chemical compounds that approximate the shape thus defined.

Chemical compounds identified by the geometric approach can be modified to satisfy criteria associated with chemical complementarity, such as hydrogen bonding, ionic interactions or Van der Waals interactions.

Another embodiment of the present invention for structure based identification of compounds comprises determining the interaction of chemical groups ("probes") with an active site at sample positions within and around a binding site or interface, resulting in an array of energy values from which three dimensional contour surfaces at selected energy levels can be generated. This method is referred to herein as a "chemical-probe approach." The chemical-probe approach to the design of a chemical compound of the present invention is described by, for example, Goodford, *J. Med. Chem.*, vol. 28, p. 849, 1985, which is incorporated by this reference herein in its entirety, and is implemented using an appropriate software package, including for example, GRID (available from Molecular Discovery Ltd., Oxford OX2 9LL, U.K.). The chemical prerequisites for a site-complementing molecule can be identified at the outset, by probing the active site of a TALL-1 protein, for example, (e.g., as represented by the atomic coordinates shown in one of the tables herein) with different chemical probes, e.g., water, a methyl group, an amine nitrogen, a carboxyl oxygen and/or a hydroxyl. Preferred sites for interaction between an active site and a probe are determined. Putative complementary chemical compounds can be generated using the resulting three dimensional pattern of such sites.

According to the present invention, suitable candidate compounds to test using the method of the present invention include proteins, peptides or other organic molecules, and inorganic molecules. Suitable organic molecules include small organic molecules. Peptides refer to small molecular weight compounds yielding two or more amino acids upon hydrolysis. A polypeptide is comprised of two or more peptides. As used herein, a protein is comprised of one or more polypeptides. Preferred therapeutic compounds to design include peptides composed of "L" and/or "D" amino acids that are configured as normal or retroinverso peptides, peptidomimetic compounds, small organic molecules, or homo- or hetero-polymers thereof, in linear or branched configurations.

In one embodiment, the compound that is identified by the method of the present invention originates from a compound having chemical and/or stereochemical complementarity with a site on a TALL-1 protein or a TALL-1 receptor. Such complementarity is characteristic of a compound that matches the surface of the enzyme either in shape or in distribution of chemical groups and binds to TALL-1 or a TALL-1 receptor to inhibit binding of TALL-1 to its receptor, for example, or to otherwise inhibit the biological activity of TALL-1 or its receptor and/or inhibit B cell proliferation, maturation, development or survival in a cell expressing TALL-1 receptor. More preferably, a compound that binds to a receptor binding site on TALL-1 or to a ligand binding site on a TALL-1 receptor associates with an affinity of at least about $10^{-6}$ M, and more preferably with an affinity of at least about $10^{-7}$ M, and more preferably with an affinity of at least about $10^{-8}$ M.

The general sites of both TALL-1 and its receptors as targets for structure based drug design or identification of candidate compounds and lead compounds (i.e., target sites), have been discussed in detail above, although other sites may become apparent to those of skill in the art using the structures provided herein. The sites generally include for TALL-1 the sites involved in trimer formation, trimer-trimer interactions (including the flap region) and receptor binding sites as described in detail herein. For TALL-1 receptors, the sites include the ligand binding sites. Combinations of any of these general sites are also suitable target sites. Even if some of such sites were generally known or hypothesized to be important sites prior to the present invention based on the linear sequence and mutational analysis or binding studies of TALL-1, the present invention actually defines the sites in three dimensions and confirms or newly identifies residues that are important targets that could not be confirmed or identified prior to the present invention. The use of any of these target sites or any other sites that can be elucidated as a result of the determination of the three dimensional structure described herein is novel and encompassed by the present invention. Many of these target sites are further described and illustrated in the Figures and Examples of the invention.

The Examples section provides specific detail regarding the structure of TALL-1 and its receptors BCMA and BAFF-R and target sites of TALL-1, BCMA and BAFF-R based on the three-dimensional structures described herein, including the identification of important residues in the structures. It is to be understood, however, that one of skill in the art, using the description of these specific structures provided herein, will be able to identify compounds that are potential candidates for modulating the biological activity of TALL-1, APRIL and the receptors for TALL-1 and APRIL, including TACI. All such embodiments are encompassed by the present invention.

A candidate compound for binding to or otherwise modulating the activity of TALL-1 or its receptors, including to one of the preferred target sites described above, is identified by one or more of the methods of structure-based identification discussed above. As used herein, a "candidate compound" refers to a compound that is selected by a method of structure-based identification described herein as having a potential for binding to TALL-1 or its receptors on the basis of a predicted conformational interaction between the candidate compound and the target site of TALL-1 or its receptors. The ability of the candidate compound to actually bind to TALL-1 or its receptors can be determined using techniques known in the art, as discussed in some detail below. A "putative compound" is a compound with an unknown regulatory activity, at least with respect to the ability of such a compound to bind to and/or regulate TALL-1 or its receptors as described herein. Therefore, a library of putative compounds can be screened using structure based identification methods as discussed herein, and from the putative compounds, one or more candidate compounds for binding to or mimicking the target TALL-1 or its receptor can be identified. Alternatively, a candidate compound for binding to or mimicking TALL-1 or its receptors can be designed de novo using structure based drug design, also as discussed above.

Accordingly, in one aspect of the present invention, the method of structure-based identification of compounds that potentially bind to or modulate (regulate) the activity of an TALL-1 or its receptors further includes steps which confirm whether or not a candidate compound has the predicted properties with respect to its effect on the actual TALL-1 or receptor. In one embodiment, the candidate compound is predicted to be an inhibitor of the binding of TALL-1 to at least one of its receptors, and the method further includes producing or otherwise obtaining a candidate compound selected in the structure based method and determining whether the compound actually has the predicted effect on the TALL-1 protein or its biological activity. For example, one can additionally contact the candidate compound selected in the structure based identification method with TALL-1 or a fragment thereof under conditions in which the TALL-1 binds to its receptor in the absence of the candidate compound; and measuring the binding affinity of TALL-1 or fragment thereof for its receptor or a fragment thereof. In this example (binding), a candidate inhibitor compound is selected as a compound that inhibits the binding of TALL-1 to its receptor when there is a decrease in the binding affinity of TALL-1 or fragment thereof for the substrate or fragment thereof, as compared to in the absence of the candidate inhibitor compound. This experiment can be used to identify compounds that inhibit the binding of TALL-1 to its receptor via binding to TALL-1 or its receptor by simple manipulation of the order of adding the compounds to the assay, for example.

In another embodiment, the candidate compound is predicted to inhibit the biological activity of TALL-1 or its receptor, and the method further comprises contacting the actual candidate compound selected by the structure-based identification method with TALL-1 or its receptor or a targeted fragment thereof, under conditions wherein in the absence of the compound, TALL-1 and/or its receptor are biologically active, and measuring the ability of the candidate compound to inhibit the activity of TALL-1 or its receptor.

In another embodiment, the candidate compound, or modeled TALL-1 or TALL-1 receptor structure in some embodiments (described below), is predicted to be a mimic or homologue of a natural TALL-1 or its receptor, respectively, and is predicted to have modified biological activity as compared to the natural TALL-1 or its receptor. For example, one can model and then produce and test a TALL-1 homologue that has different receptor binding affinity as compared to the natural TALL-1, or a homologue that increased or decreased biological activity as compared to the natural TALL-1. Such homologues can be useful in various biological assays or as competitive inhibitors.

In one embodiment, the conditions under which TALL-1 or a TALL-1 receptor according to the present invention is contacted with a candidate compound, such as by mixing, are conditions in which the protein is not stimulated (activated) or bound to a natural ligand or receptor if essentially no candidate compound is present. In one aspect, a natural ligand or substrate can be added after contact with the candidate compound to determine the effect of the compound on the biological activity of TALL-1 or its receptor. Alternatively, this aspect can be designed simply to determine whether the candidate compound binds to the TALL-1 or its receptor (i.e., in the absence of any additional testing, such as by addition of the receptor or ligand, respectively). For example, such conditions include normal culture conditions in the absence of a stimulatory compound or binding ligand or receptor.

In another embodiment, the conditions under which TALL-1 or its receptor according to the present invention is contacted with a candidate compound, such as by mixing, are conditions in which the protein is normally bound by a ligand or receptor, or activated, if essentially no candidate compound is present. Such conditions can include, for example, contact of TALL-1 or its receptor with the appropriate binding ligands or other stimulatory molecule. In this embodiment, the candidate compound can be contacted with TALL-1 or its receptor prior to the contact of TALL-1 or its receptor with the binding ligand (e.g., to determine whether the candidate compound blocks or otherwise inhibits the binding of TALL-1 or its receptor to its ligand, or inhibits the biological activity of TALL-1 or its receptor), or after contact of TALL-1 or its receptor with the binding ligand (e.g., to determine whether the candidate compound downregulates, or reduces the biological activity of TALL-1 or its receptor after the initial contact with the binding ligand).

The present methods involve contacting TALL-1 or its receptor with the candidate compound being tested for a sufficient time to allow for binding to, activation or inhibition of the enzyme by the candidate compound. The period of contact with the candidate compound being tested can be varied depending on the result being measured, and can be determined by one of skill in the art. For example, for binding assays, a shorter time of contact with the candidate compound being tested is typically suitable, than when activation is assessed. As used herein, the term "contact period" refers to the time period during which TALL-1 or its receptor is in contact with the compound being tested. The term "incubation period" refers to the entire time during which cells expressing TALL-1 or its receptor, for example, are allowed to grow or incubate prior to evaluation, and can be inclusive of the contact period. Thus, the incubation period includes all of the contact period and may include a further time period during which the compound being tested is not present but during which growth or cellular events are continuing (in the case of a cell based assay) prior to scoring. It will be recognized that shorter incubation times are preferable because compounds can be more rapidly screened.

In accordance with the present invention, a cell-based assay is conducted under conditions that are effective to screen candidate compounds selected in the structure-based identification method to confirm whether such compounds are useful as predicted. Effective conditions include, but are not limited to, appropriate media, temperature, pH and oxygen conditions that permit the growth of the cell that expresses TALL-1 or its receptor. An appropriate, or effective, medium refers to any medium in which a cell that naturally or recombinantly expresses TALL-1 or its receptor, when cultured, is capable of cell growth and expression of TALL-1 or its receptor. Such a medium is typically a solid or liquid medium comprising growth factors and assimilable carbon, nitrogen, sulfur and phosphate sources, as well as appropriate salts, minerals, metals and other nutrients, such as vitamins. Culturing is carried out at a temperature, pH and oxygen content appropriate for the cell. Such culturing conditions are within the expertise of one of ordinary skill in the art.

Cells that are useful in the cell-based assays of the present invention include any cell that expresses TALL-1 or its receptor and particularly, other components related to B cell development, proliferation, maturation or survival.

The assay of the present invention can also be a non-cell based assay. In this embodiment, the candidate compound can be directly contacted with an isolated TALL-1 or its receptor, or a portion thereof (e.g., a portion comprising a receptor or ligand binding region), and the ability of the candidate compound to bind to the protein or portion thereof can be evaluated. The assay can, if desired, additionally include the step of further analyzing whether candidate compounds which bind to TALL-1 or its receptor are capable of increasing or decreasing the activity of TALL-1 or its receptor. Such further steps can be performed by cell-based assay, as described above, or by a non-cell-based assay that measures a parameter of TALL-1 or its receptor activity. For example, TALL-1 or its receptor can be immobilized on a solid support and evaluated for binding to a candidate compound and additionally, activity can be measured if the appropriate conditions and substrates are provided. Proteins can be immobilized on a substrate such as: artificial membranes, organic supports, biopolymer supports and inorganic supports. The protein can be immobilized on the solid support by a variety of methods including adsorption, cross-linking (including covalent bonding), and entrapment. Adsorption can be through van del Waal's forces, hydrogen bonding, ionic bonding, or hydrophobic binding. Exemplary solid supports for adsorption immobilization include polymeric adsorbents and ion-exchange resins. Solid supports can be in any suitable form, including in a bead form, plate form, or well form.

In one embodiment, a BIAcore machine can be used to determine the binding constant of a complex between TALL-1 or its receptor and a candidate compound or between TALL-1 and its receptor, for example, in the presence and absence of the candidate compound. The dissociation constant for the complex can be determined by monitoring changes in the refractive index with respect to time as buffer is passed over the chip (O'Shannessy et al. Anal. Biochem. 212:457-468 (1993); Schuster et al., Nature 365:343-347 (1993)). Contacting a candidate compound at various concentrations with TALL-1 or its receptor and monitoring the response function (e.g., the change in the refractive index with respect to time) allows the complex dissociation constant to be determined in the presence of the candidate compound.

Other suitable assays for measuring the binding of a candidate compound to TALL-1 or its receptor and/or for measuring the ability of such compound to affect the binding of an TALL-1 to its receptor include, for example, immunoassays such as enzyme linked immunoabsorbent assays (ELISA) and radioimmunoassays (RIA), or determination of binding by monitoring the change in the spectroscopic or optical properties of the TALL-1 or its receptor, through fluorescence, UV absorption, circular dichrosim, or nuclear magnetic resonance (NMR).

Candidate compounds identified by the present invention can include agonists of TALL-1 or TALL-1 receptor activity and antagonists of TALL-1 or TALL-1 receptor activity, with the identification of antagonists or inhibitors being preferred.

Yet another embodiment of the present invention relates to a method to produce a TALL-1 or TALL-1 receptor homologue with modified biological activity as compared to a natural TALL-1 or TALL-1 receptor. This method includes the steps of: (a) obtaining atomic coordinates that define the three dimensional structure of TALL-1 or a TALL-1 receptor, including any of the TALL-1 or TALL-1 receptor three dimensional structures or atomic coordinates described herein; (b) using computer modeling of the atomic coordinates in (a) to identify at least one site in the TALL-1 or TALL-1 receptor structure that is predicted to contribute to the biological activity of TALL-1 or the TALL-1 receptor; and (c) modifying the at least one site in the TALL-1 or TALL-1 receptor protein to produce a TALL-1 homologue or TALL-1 receptor homologue which is predicted to have modified biological activity as compared to a natural TALL-1 or TALL-1 receptor. The final step of modifying the site on TALL-1 or a TALL-1 receptor can be performed by producing a "virtual TALL-1 or TALL-1 receptor homologue" on a computer, such as by generating a computer model of a TALL-1 or TALL-1 receptor homologue, or by modifying a TALL-1 or TALL-1 receptor to produce the homologue, such as by classical mutagenesis or recombinant technology.

The atomic coordinates that define the three dimensional structure of TALL-1 or a TALL-1 receptor and the step of obtaining such coordinates have been described in detail previously herein with regard to the method of structure based identification of compounds. Computer modeling methods suitable for modeling the atomic coordinates to identify sites in a TALL-1 or TALL-1 receptor structure that are predicted to contribute to the biological activity of a TALL-1 or TALL-1 receptor, as well as for modeling homologues of TALL-1 or a TALL-1 receptor, have been discussed generally above. A variety of computer software programs for modeling and analyzing three dimensional structures of proteins are publicly available. The Examples section describes in detail the use of a few of such programs. Such computer software programs include, but are not limited to, the graphical display program O (Jones et. al., Acta Crystallography, vol. A47, p. 110, 1991), the graphical display program GRASP, MOL-SCRIPT 2.0 (Avatar Software AB, Heleneborgsgatan 21C, SE-11731 Stockholm, Sweden), the program CONTACTS from the CCP4 suite of programs (Bailey, 1994, Acta Cryst. D50:760-763), or the graphical display program INSIGHT.

Once target sites for modification on a TALL-1 or TALL-1 receptor are identified, TALL-1 or TALL-1 receptor homologues having modifications at these sites can be produced and evaluated to determine the effect of such modifications on TALL-1 or TALL-1 receptor biological activity. In one embodiment, a TALL-1 or TALL-1 receptor homologue can be modeled on a computer to produce a computer model of a TALL-1 or TALL-1 receptor homologue which predicts the effects of given modifications on the structure of the protein and its subsequent interaction with other molecules. Such computer modeling techniques are well known in the art.

In another aspect, or subsequent to an initial computer generation and evaluation of a TALL-1 or TALL-1 receptor homologue model, an actual TALL-1 or TALL-1 receptor homologue can be produced and evaluated by modifying target sites of a natural TALL-1 or TALL-1 receptor to produce a modified or mutant TALL-1 or TALL-1 receptor (described in detail above).

Another embodiment of the present invention relates to a computer for producing a three-dimensional model of a molecule or molecular structure, wherein the molecule or molecular structure comprises a three dimensional structure defined by atomic coordinates of a TALL-1 or TALL-1 receptor according to any one the tables of coordinates disclosed herein, or a three-dimensional model of a homologue of the molecule or molecular structure as described above. The computer comprises: (a) a computer-readable medium encoded with the atomic coordinates of the TALL-1 or TALL-1 receptor as described previously herein to create an electronic file; (b) a working memory for storing a graphical display software program for processing the electronic file; (c) a processor coupled to the working memory and to the computer-readable medium which is capable of representing the electronic file as the three dimensional model; and, (d) a display coupled to the processor for visualizing the three dimensional model. The three dimensional structure of the TALL-1 or TALL-1 receptor is displayed or can be displayed on the computer.

Yet another embodiment of the present invention relates to a method to load a therapeutic agent into a carrier for in vivo delivery, comprising mixing a therapeutic agent with soluble TALL-1 protein monomers or portions thereof or trimers at a pH below about 7.4 and then raising the pH of the mixture to a pH of about 7.4 or higher to form oligomers of sTALL-1 or portions thereof containing the therapeutic agents for delivery in vivo. Also included in the invention are complexes of at least one therapeutic agent and sTALL-1 monomers produced by this method. This embodiment relates to the discovery by the present inventors that TALL-1 forms stable oligomers at pH of about 7.4 or higher, but exists as soluble trimers and monomers at lower pH. The therapeutic agent can be any therapeutic agent for which it is desired to use a large carrier such as a TALL-1 oligomer.

Finally, one embodiment of the invention relates to the production of a TNF-family member protein that has been modified by the introduction into the structure of said TNF-family member protein of a structure that is substantially similar to the "flap" structure of a TALL-1 protein, and the use of such a protein in a method of treatment of a disease or condition that can be regulated by a TNF-family member protein activity.

All publications and patents referenced herein are incorporated herein by reference in their entireties.

The following examples are provided for the purpose of illustration and are not intended to limit the scope of the present invention.

EXAMPLES

Example 1

The following example describes the crystallization of sTALL-1.

Protein Expression, Purification and Crystallization

The cDNA fragment encoding amino acids 134-285 of human TALL-1 (SEQ ID NO:2) was amplified from a TALL-1 full-length cDNA clone (Shu et al., (1999) *J. Leukocyte Biology* 65:680-683; Shu et al., (2000) *Proc. Natl. Acad. Sci. USA.* 97:9156-9161) by PCR using a plasmid template and primers containing restriction sites for pET14b (Tagged with $His_6$)(Novergen). The final clones have been verified by restriction digestion and DNA sequencing. The recombinant plasmid containing the sTALL-1 gene was transformed to *E. coli* BL21 (DE3)pLysS. Enhanced expression of $His_6$-sTALL-1 was induced by adding IPTG (isopropyl-1-thio-b-D-galactopyranoside) to a 8 L growing culture (37° C.) at an $OD_{650}$ of 0.7. After 4 hrs of additional growth, cells were harvested, resuspended in buffer (50 mM Tris-HCl, 1 mM EDTA, pH 8.0, 300 mM NaCl, 5% glycerol and 1 mM DTT). After cell lysis through a continuous-flow French press and a low-speed spin, the soluble fraction was loaded onto a $Ni^{2+}$-chelating affinity column and $His_6$-sTALL-1 was eluted with 100 mM imidazole. $His_6$-sTALL-1 was loaded onto a MonoQ (Pharmacia) ion-exchange column. After elution with a NaCl gradient, the protein was homogeneous as judged by Coomassie stained SDS-polyacrylamide gels. The $His_6$ tagged fusion protein was used for final crystallization screen. sTALL-1 (15 mg/ml) was crystallized by vapor diffusion against 5 mM β-mercaptoethanol, 50 mM Bicine pH9.0, 150 mM NaCl, and 35-38% dioxane. Heavy-atom derivatives were prepared by soaking crystals for 24 hrs in 1 mM $HgCl_2$ and 48 hrs in 1 mM Mersayl, all dissolved in the crystallization solution. For cryo-crystallography, crystals were soaked in 35% MPD with crystallization buffer for 30 minutes before flash-freezing.

Structure Determination and Refinement

Crystals of sTALL-1 diffracted to 3.5 Å and have high mosaicity (above 1.0°). Large crystal sizes did not improve the crystal diffraction ability and mosaicity. Altering crystallization conditions did not produce any better results. Finally, mercury treatments (sTALL-1 sample was soaked in 0.1 mM $HgCl_2$ for 10 hours) on the sTALL-1 protein before crystallization were employed. This sample produced crystals at similar conditions as the native protein of sTALL-1. The new crystals diffracted to 2.8 Å at an in-house x-ray generator and with reasonable mosaicity (0.5°). The cell dimensions of these crystals are 234 Å×234 Å×217 Å and these crystals are in space group of $P6_322$. The molecular weight of the $His_6$ tagged sTALL-1 is ~20 k Da. Assuming all monomers form trimers in solution and crystal packing. It was impossible for the inventors to define the exact solvent contents of the sTALL-1 crystals (Matthews, B. W. (1968) *J. Mol. Biol* 33:491-497). Data collection and heavy atom screen were followed. All data sets are processed by DENZO and SCALEPACK (Otwinowski et al., (1997) *Methods Enzymol* 276:307-326). Due to the low sequence homology among TNF ligand family members, it was expected that it might be difficult to find molecular replacement solutions. This turned out to be the case when all available molecular replacement programs were tried. Based on the initial $V_m$ analysis, there are at least 3 trimer or 9 monomers in an asymmetry unit. The inventors tried both monomer and trimer of TNFα, TNFβ, CD40L and TRAIL as initial search models. All of these search models failed to generate a molecular replacement solution. Traditional heavy atom screens were carried out. Two mercury derivatives (Table 1A) were found. Three data sets of sTALL-1 were inputted to the program "SOLVE" (Terwilliger et al., (1987) *Acta Cystallogr. A* 43:34-38), and the output map were subjected to solvent flattening in "SOLOMON" (Sheldrick, G. M. (1987) In isomorphous Replacement and Anomalous Scattering, Proc. CCP4 st. W. Wolf, P. R. Evans, A. G. W. Leslie, Eds. (daresbury Laboratory, Warrington, UK) P23). The solvent flattened map was used for model building in program "O" (Jones et al., (1991) *Acta crystallogr. A*47:110-119). The 3.0 Å MIR map of sTALL-1 has excellent quality. All side chains of residues 142-285 were resolved. Tracing and model building were performed with the help of a TNFβ model (Eck et al., (1992) *J. Biol. Chem.* 267:2119-2122). The 10 mercury sites per asymmetric unit and their symmetry related sites lead to two ball-like arrangements in one unit cell (a=b=234, b=217 Å, α=90, β=90, γ=120) with each ball containing 60 sites. This feature reminded the inventors of a T=1 virus structure, and also indicates that there are 10 monomers in the asymmetry unit instead of integrate numbers of trimers as was assumed in the calculation of solvent contents initially. The 10 monomers of the asymmetry unit were built independently. sTALL-1 model was first subjected to rigid body refinement and then conventional positional minimization in program "CNS" (Brunger et al., (1998) *Acta. Cyst.* D54:905-921) with non-crystallographic symmetry constrains. The output model was then subjected to the "slow cooling" dynamic annealing refinement and a group B-factor refinement. The final refined R factor is 23.6% and R free is 25.2%. It was surprising that there are no mercury atoms in the sTALL-1 structure, which are derived from the pre-$HgCl_2$, treated sample, although the behavior of the sTALL-1 sample was completely changed after $HgCl_2$ treatments.

TABLE 1A

Experimental data on crystal structure determination and refinement

| Data Set | Resolution (Å) | $R_{merge}$ (%) | No. of unique reflections | Total Observations | Completeness (%) | Phasing power | No. of Sites |
|---|---|---|---|---|---|---|---|
| Native | 3.0 | 11.7 | 66001 | 334821 | 95.7 | | |
| HgCl$_2$ | 3.0 | 14.6 | 111792 | 317553 | 85.2 | 1.39 | 10 |
| Mersalyl | 3.2 | 11.4 | 101595 | 247096 | 94.5 | 0.67 | 10 |

Mean Figure of Merit = 0.37 (for 54518 phased reflections)

Refinement

| Resolution (Å) | 20-5.95 | 4.75 | | 4.15 | 3.78 | 3.51 | 3.30 | 3.14 | 3.00 | |
|---|---|---|---|---|---|---|---|---|---|---|
| No. reflections | 7850 | | 7545 | 7472 | 7158 | 6732 | 6328 | 4927 | 3740 | 51752 |
| R-factor | 23.12 | | 21.06 | 18.73 | 22.84 | 25.08 | 27.78 | 31.34 | 33.67 | 23.61 |
| Free R-factor | 25.48 | | 21.37 | 20.45 | 24.71 | 26.92 | 28.07 | 33.48 | 35.03 | 25.22. |

$R_{merge} = \Sigma|I_j - <I>|/\Sigma I_j$ with Bijvoet pairs treated as equivalent for native, as different for derivatives.
Total observations, the number of full and partial observations measured with non-negative intensity to the indicates resolution.
Completeness, the percentage of possible unique reflections measured with $I/\sigma(I) \geq 0$ to the indicated resolution.
Phasing power = $<F_H>/E_{rms}$.
No. reflections, the number of reflections used in refinement for each resolution bin.
R-factor = $\Sigma|F_O - F_C|/\Sigma F_0$ for all amplitudes with $F/\sigma(F) \geq 2$ measured in the indicated resolution bin; the free R-factor is calculated with 5% of the data in each bin.

Overall Structure

The structure of the soluble portion of TALL-1 was determined by the multiple isomorphous replacement method using two mercury derivatives (Table 1A). The electron density map was improved by solvent flattening. The structure has been refined to an R-factor of 23.6% ($R_{free}$-factor of 25.2%) against data extending to 3.0 Å resolution in space group P6$_3$22, with ten sTALL-1 monomers in the asymmetric unit(unit cell of 234×234×217 Å). The current model of the sTALL-1 monomer contains residues 142 to 285 (SEQ ID NO:2), with all side-chains well defined (FIG. 1A).

The structure of sTALL-1 consists of two layered antiparallel β strands that form a typical jellyroll-like β sandwich, as with other members of the TNF ligand family (Jones et al., (1989) Nature 338:225-228; Eck et al., (1989) J. Biol. Chem., 264:17595-17605; Eck et al., (1992) J. Biol. Chem. 267: 2119-2122; Karpusas et al., (1995) Structure 3:1031-1039; Cha et al., 1999, Immunity 11:253-261). Compared to known structures of other family members, the overall structure of sTALL-1 is shorter along the 3-fold axis that generates the trimers (FIG. 1B). This was even more obvious when the trimers of sTALL-1 and TNFα were superimposed, which generated an overall RMSD of 1.9 Å (FIG. 1C). The effect is caused by the shortening of two β strand pairs, CD and EF (FIG. 1A). This is consistent with the fact that the connecting regions that link β strands CD, EF, and GH are the most divergent regions among the TNF family ligands. Two additional unique features are termed "elbow" and "flap" regions (FIG. 1A). The "elbow" region contains a short β hair-pin labeled A" and A'". There is a similar region in TRAIL, which is not well defined from the available structures of TRAIL, contrasting with the well ordered β hair-pin of sTALL-1 (Cha et al., 1999, supra; Mongkolsapaya et al., 1999, supra; Hymowitz et al., 1999, supra). The "flap" region is unique to sTALL-1 based on results of sequence alignments and structural comparisons (FIG. 1B, 1D). There is also a disulfide bridge between residue Cys232 on strand E and residue Cys245 on strand F, which is unique for TALL-1, TALL-2, Tweak, and EDA (Bodmer et al., 2000, supra).

The interfaces that form the trimer of sTALL-1 mostly consist of layered aromatic residues including Phe194, Tyr196, and Tyr246 from three monomers, which are conserved for all TNF ligand family members. Interestingly, one triple Phenylalanine layer in TNFα, TNFβ, CD40L, and TRAIL is replaced by triple Leu282s in sTALL-1 trimer. There are two additional interaction layers of triple residues in sTALL-1 trimer. One consists of residues Gln144 from reach monomers, forming a H-bond net. Another layer is formed by three Leu285 residues from C-terminus of three monomers. The hydrophobic interactions appear to be the main forces driving trimer formation.

The unique "flap" region of sTALL-1 mediates trimer-trimer interactions that lead to a remarkable virus-like assembly of the sTALL-1 trimers. There are 10 sTALL-1 monomers in the asymmetric unit with a space group of P6$_3$22 (FIG. 2A). The 10 monomers interact to form virus-like clusters containing 60 sTALL-1 monomers (20 trimers) (FIG. 2B, 2C). Within the unit cell, there are two virus-like clusters. This structure resembles the T=1 virus structures such as satellite tobacco necrosis virus (STNV, PDB ID:2STV) (Jones et al., (1984) J Mol Biol 177:735-767). The overall RMSD of main chain is 2.1 Å between sTALL-1 and STNV. In STNV structure, 5 monomers form a pentamer, a virus envelope is built up by 12 pentamers and the interactions among pentamers are mediated by two short helices. Interestingly, when the structure of TNFα was reported, the authors noticed the structural similarity between TNFα and the capsid protein of STNV (Jones et al., (1989) Nature 338:225-228). Moreover, they speculated that these two proteins could have evolved from a common ancestor and that TNFα may form a virus-like structure under certain circumstances (Jones et al., (1989) Nature 338:225-228). The structure of sTALL-1 is a piece of strong evidence supporting that speculation.

Trimer-Trimer Interactions

The trimer-trimer interactions are extensive. They not only include hydrogen bond net works and salt bridges, but also hydrophobic contacts. Residues involved in trimer-trimer interactions are not only from the monomer that contributes the "flap" region but also the neighboring monomer as well (FIG. 3A, 3B). Due to the resolution limitation, detailed hydrogen bond networks will not be discussed here. There are three major interaction interfaces that bring two trimers together, two of them are involved in the interactions of two monomers, layer 1 and layer 2 respectively (FIG. 3B). Layer 1 consists of residues Tyr192, Lys252, Glu254, and His218 from one monomer, residues Tyr192', Lys252', Glu254', and His218' from another monomer. The side chains of residue Lys252 and Glu254 form ionic bonds with these of residue Glu254' and Lys252'. These interactions are further strengthened by the hydrogen bond net formed by side chains of all residues from this layer (FIG. 3C, 3D). Interestingly, except residues His218 and His218' from the "flap" regions, all others are from β strands C and F. These interactions could exist in other TNF ligand members that do not contain a distinguishable "flap" region. Further investigation of the biological consequence of the interaction for other members will be of great interest and importance.

Layer 2 consists of residues Lys216, Glu223, Leu224, Val227, and Leu229 from each monomer (FIG. 3E, 3F). The side chains of residues Lys 216 and Glu223 from one monomer form ionic bonds with Glu223' and Lys216' of another. The side chains of residues Val227, Leu229, part of Lys216 and Glu223' form one hydrophobic core, side chains of Val227', Leu229', part of Lys216' and Glu223 form another. The interaction of residues Leu224 and Leu224' further bolsters the "flap"–"flap" interactions (FIG. 3E, 3F).

The interactions of the third layer are among three monomers, monomer 1, 1' and 2' (FIG. 3G). The side chain of residue Val219 from the "flap" region of monomer 1 interacts with the side chains of residues Ile150 and Leu169 of monomer 2' to form one hydrophobic core. The side chain of residue Phe220 from the "flap" region of monomer 1, side chains of residues Tyr192 and Ile250 from monomer 1', and the side chain of residue Phe172 from monomer 2' form another hydrophobic core. The two hydrophobic cores, which bring three monomers together, are separated by the main chain of the "flap" from monomer 1, (FIG. 3G, 3H). Additional hydrogen bonds formed by three monomers at this region further intensify these tri monomer-monomer interactions. The present inventors believe that these interactions also greatly improve the stability of the traditional trimer, which is formed by monomer 1, 2 and 3 or monomer 1', 2' and 3' (FIG. 3A).

From the previous results discussed in the Background, the trimer is believed to be the functional unit for the TNF ligand family members (Locksley et al., 2001, supra; Fesik, 2000, supra) (FIG. 1C). Due to the intensive interactions among the sTALL-1 trimers in the crystal structure, the inventors propose that the functional unit comprises more than a single trimer. Based on the crystal structure of sTALL-1, the inventors can isolate several possible sub-clusters that may act as the functional unit in vivo. The first is the dimer of trimers (FIG. 53A). The second is the tetramer of trimers (FIG. 5A). The third is the pentamer of trimers, which is formed by encircling trimers (FIG. 5B). Finally, based on the gel-filtration and electron microscopy results (see Example 2), the inventors suggest that the most likely functional unit is the entire virus-like cluster (FIG. 2).

Example 2

The following example demonstrates that the virus-like assembly of TALL-1 exists in solution.

To confirm that the virus-like assembly of sTALL-1 exists in solution and is not the result of a crystal-packing artifact, the present inventors employed two methods, gel-filtration and electron microscopy. The assembly state of sTALL-1 was investigated on a Superose-6-gel-filtration column. From the final elution profile, the sTALL-1 sample contains assemblies with an estimated molecular weight greater than 670,000 Da and smaller than 2,000,000 Da, consistent with the calculated molecular weight of the 60mer virus-like assembly of approximately 1,200,000 Da. To evaluate the stability of the assembly, different salt concentrations were applied. Three salt concentrations (10 mM NaCl, 500 mM NaCl, and 1M NaCl in 50 mM Tris-HCl buffer at pH 8.0) led to the same sharp elution profile, consistent with the present inventors' structural information that the trimer-trimer interactions involve not only electrostatic contacts but also extensive hydrophobic contacts. These results also can be repeated on the Superdex-200 gel-filtration column (Superdex-200 HR10/30, Pharmacia), although sTALL-1 came out at a void volume ($V_0$, 48 mL) (data not shown).

These results are not consistent with two published results (Schneider et al., (1999) *J Exp Med*. 189:1747-56; Kanakaraj et al., (2001) *Cytokine*. 13:25-31), both of which claimed that sTALL-1/BAFF existed only as trimers. Comparing these experimental procedures with the published results, the present inventors noticed that the analyses of sTALL-1/BAFF were carried out at different pHs: pH 6.0 in the Kanakaraj study, pH 7.0 in the Schneider study, and pH7.4 and above in the present inventors' studies. To evaluate the influence of pH on the oligomeric state of sTALL-1, gel-filtrations were run using sTALL-1 from bacteria on Superdex-200 at a series of pHs (data not shown). At pH 6.0, sTALL-1 exists exclusively as trimers. The ratio of oligomers to trimers at pH 6.5 was 1:2, rose to 1:1 at pH 7.0, and majority are oligomers (30:1) at pH7.2. At pH7.4 the present inventors could detect only oligomeric sTALL-1 (data not shown). To rule out that sTALL-1 from different sources may behave differently, purified sTALL-1 from the 293 cell line as well as sTALL-1 produced by a mouse myeloma cell line were analyzed (R&D Systems, Inc., Minneapolis). Both existed exclusively as oligomers at pH7.4 (data not shown). The present inventors believe that two histidine residues (with $pK_2$=6.0) in the "flap" region may play crucial roles in the pH dependent association and dissociation property of sTALL-1 (FIG. 3C, 3D). Interestingly, there are trimers as well as monomers of sTALL-1 at Ph7.0.

For electron microscopy, a 5 µl of sTALL-1 suspension (5 mg/ml) was applied for one minute onto carbon coated grid previously glow discharged. After removing the excess of liquid with a filter paper, the grid was washed with 2 drops of buffer and then negatively stain with saturated uranyl acetate. Electron micrographs were recorded at a magnification of 60,000× with a Philips CM 12 transmission electron microscopy (Philips Electron Optics, Eindhoven, The Netherlands) operating at 100 kV.

The 200 Å diameter virus-like assembly observed in the crystal structure is of sufficient size to be easily detected by electron microscopy. This proved to be the case. The negatively-stained virus-like clusters are clearly observed in electron micrographs after absorption of the sample to a carbon electron microscope (FIG. 4A). The diameter and the shape of the particle observed by electron microscopy is consistent with the crystal structure (FIG. 4B, 4C).

Example 3

The following example describes experiments that demonstrate that the "flap" region is involved in the cluster formation by TALL-1.

To further confirm the exact region that leads to the formation of the virus-like cluster and the functional role of the "flap" region, the present inventors constructed a mutated version of sTALL-1 with 8 residues (residue 217 to residue 224 of SEQ ID NO:2) replaced by two glycines at the "flap" region. The truncated sTALL-1 (sTALL-1 217-224) was overexpressed and purified as the native sTALL-1 (see Example 1).

For gel-filtration, wild type sTALL-1 and mutant sTALL-1 (each of 1 mg) were loaded onto the Superdex-200 HR 10/60

(Pharmacia) respectively. The wild type sTALL-1 came out at void volume (45-50 mL) and the mutant trimers and monomers came out at elution volumes of 78 mL and 87 mL respectively (data not shown). Direct fresh medium (6 mL) that grow 293 cells was loaded on to the Superdex-200 column. All fractions at different elution volume were concentrated for final western-blot experiment followed the procedure as described (Shu et al., 1999, supra), sTALL-1 were detected at elution volume of 48 mL and 80 mL respectively (data not shown).

Gel-filtration of the truncated sTALL-1 sample on a Superdex-200 column yielded two peaks with molecular weight of around 60,000 Da and 20,000 Da (data not shown). These peaks consistently appear in the elution profile at all three salt concentrations. These molecular weights correspond to a monomer and a trimer of the truncated sTALL-1. These data demonstrate that after truncation of the "flap" region, the cluster forming property of sTALL-1 is abolished. Furthermore, disruption of the "flap" region also affects trimer formation, which is consistent with the present inventors' observation of a hydrophobic core formed by residues from three monomers at the monomer-monomer interaction interface. Although the "flap" regions of one trimer do not involve in the formation of the trimer itself (FIG. 1C), they do affect the stability of neighboring trimers. These data are also consistent with the observation that for some family members, trimers can be transformed to monomers over a period of time in solution (Cha et al., 1999, supra; Corti et al., (1992) *Biochem. J.* 284, 905-910).

From the structural results, the inventors note that the "flap" region is in the corresponding location for the binding of one CRD of the cognate receptors of TNFβ and TRAIL. To investigate if the truncation of the "flap" region of sTALL-1 affects its receptor binding capacity and affinity, binding assays of native and truncated sTALL-1 to the cognate receptor BCMA were carried out.

For these experiments, the extracellular domain of BCMA (residues from 1 to 51; SEQ ID NO:6) for BIAcore experiments was overexpressed as GST-BCMA fusion protein on pGEX4T-2 vector in BL-21 strain. Cell preparation and protein purification procedure are similar to that of sTALL-1. Briefly, harvest cells were broken through a French press and low speed spin. The soluble fraction was loaded onto a GST affinity beads. After intensive wash with binding buffer, thrombin was added for 24 hrs incubation. Supernatant that contained the extracellular domain of BCMA was loaded onto a MonoQ column and eluted with NaCl gradient. The protein is above 99% pure after MonoQ.

First, BCMA-transfected 293 cells were incubated with control medium, wild type sTALL-1 in the control medium, and mutant sTALL-1 in the control medium. Cell staining was performed by sequential incubation (each 40 min) with anti-His$_6$ mAb and RPE-conjugated goat anti-rabbit IgG in staining buffer. The fluorescence was measured by using a Becton Dickinson FACScan flow cytometer (Shu et al., 2000, supra) (data not shown). Flow cytometry analysis results showed that the truncated sTALL-1 and the wild sTALL-1 had similar binding capacity to cells that overexpressed entire BCMA (data not shown).

The binding affinity of BCMA for the wild type versus mutant sTALL-1 was further determined using BIACore surface plasmon resonance. To obtain the true affinity of the receptor without the confounding effect of multivalent binding, the polyvalent TALL-1 proteins were immobilized in the instrument flow cells and the soluble monomeric BCMA was injected in the mobile phase. The KD of the interaction was calculated by Scatchard analysis of the equilibrium data (data not shown). Briefly, wild type multimeric sTALL-1 and mutant trimeric sTALL-1 were immobilized (11,000 and 3000 RU, respectively) in separate flow cells of a CM-5 BIAcore Biosenser chip using standard amine coupling reagents. Various concentrations (10-1000 nM) of monomeric BMCA were injected for one min at a flow rate of 20 μl/min in a buffer of 100 mMNaCl, 20 mM Tris-HCl pH8.0 and 0.005% P20 detergent and the binding kinetics recording. For base line calculations the same BMCA samples were injected in a control flow cell with no protein immobilized. Receptor binding kinetics were too rapid for accurate measurements of on rates and off rates, but equilibrium binding values (Rmax) were used to calculate the overall affinity of receptor binding by Scatchard analysis.

Results showed that the receptor bound to the two ligands with very similar affinity, indicating the removal of the TALL-1 flap did not alter its affinity for its receptor. An affinity of about 100 nM for this monomer interaction is consistent with reports of 0.1-1.0 nM apparent affinities for trivalent interactions of TNF family members with immobilized or cell bound receptors. Therefore, it is clear that the "flap" region is not involved in receptor binding.

To understand the functional role of the "flap" region, transfection assays of both wild type and truncated sTALL-1 were performed. Luciferase reporter gene assays were carried out as described (Shu et al., 2000, supra). Briefly, 293 cells were transfected with 0.5 μg of NF-κB luciferase reporter plasmid and increased amounts of an expression plasmid for BCMA. Fourteen hours after transfection, cells were treated wild type sTALL-1, mutant sTALL-1, or left untreated for 7 hrs and luciferase reporter assays were performed.

Wild type sTALL-1 gave a dose dependent activation of NF-κB in reporter gene assays. Truncated sTALL-1 was defective in activating NF-κB at a variety of BCMA concentrations (data not shown). These data demonstrated that, despite the normal binding of the truncated sTALL-1 to the receptor, the "flap" region is essential for the proper function of sTALL-1 in vivo.

To avoid possible artificial results brought in from the 293 cell transfection assay system, B lymphocyte (from human peripheral blood of health donors) proliferation stimulation by wild type sTALL-1 and mutant sTALL-1 were carried out. B cell proliferation assays followed the procedure as described (Shu et al., 2000, supra). Briefly, human peripheral B lymphocytes were purified from peripheral blood of health donors. Purified B lymphocytes were seeded on 96-well dishes and treated with indicated reagents for 40 h. Cells were pulsed for an additional 10 h with [$^3$H]thymidine. Incorporation of [$^3$H]thymidine was measured by liquid scintillation counting (data not shown). These costimulation assays indicated that wild type sTALL-1, but not mutant sTALL-1 significantly ($P<0.01$) stimulate B lymphocyte proliferation (data not shown).

Example 4

The following example demonstrates that sTALL-1 clusters exist under physiological conditions.

To assess whether the sTALL-1 cluster exists in vivo, medium from sTALL-1 overexpressing 293 cells was collected and loaded onto a gel-filtration column (Superdex-200 HR 10/60, Pharmacia) eluting with PBS buffer at pH7.4. The eluted fractions were then subjected to western-blot analysis. sTALL-1 exists both as clusters and trimers, judging from the elution volumes (data not shown), indicating that sTALL-1 clusters could exist under physiological condition. To find out if there is an equilibrium between clusters and trimers, the two peaks corresponding to clusters and trimers were collected and concentrated and finally applied back to the same gel-filtration column. For the cluster peak fraction, the same elution profile was obtained, a single sharp and symmetric peak at the cluster position, there was no detectable sTALL-1 at the trimer position. On the other hand, the trimer peak fraction generated two peaks corresponding to the cluster and trimer positions (data not shown). It is clear from these results that sTALL-1 predominantly in the cluster state rather than a trimer in solution at pH7.4. The process of cluster formation from trimers is irreversible.

Current data indicate that TNF family ligands function as trimers binding to the cognate receptors. The recruitment of receptors leads to clustering of the cytoplasmic domains, which in turn stimulates the recruitment of adaptor proteins and other downstream partners. The virus-like cluster of sTALL-1, which the present inventors have shown is required for function, contradicts this paradigm. There is one possible mechanism that may involve the activation of the downstream pathway. The virus-like cluster of sTALL-1 could recruit numerous receptor trimers. This increase of local concentration of the receptors could facilitate signaling through the cellular membrane to the cytoplasm of the cell. The clustering of numerous cytoplasmic domains could lead to signal amplification by recruiting downstream elements. This model resembles the well-characterized SMAC (SuperMolecular Activation Cluster) complexes (Monks et al., (1998) *Nature* 395:82-6), in which multiple copies of T cell receptors, peptide bound major histocompatibility complex molecules, other related accessory proteins, and their counter-receptors from T cells and antigen presenting cells gather together to form clusters that resemble neural synapses (Monks et al., (1998) *Nature* 395:82-6).

Example 5

The following example describes an analysis of other TNF family members for the "flap" region discovered in TALL-1.

The present inventors' structural and functional analysis indicates that the sTALL-1 "flap" region mediates the cluster assembly formation, and is essential for the activation of NF-κB. To determine whether this flap region exists in other family members, the inventors performed a structure-based sequence alignment of all available 18 family members (TALL-1, TRAIL, TNFβ, CD40L, TNFα, RANKL, APRIL, FasL, LTb, CD30L, CD27L, OX40L, 4-1BBL, EDA-A1, EDA-A2, AITRL, VEGI, LIGHT, TWEAK). The four known TNF ligand structures (Jones, et al., 1989; Eck, et al., 1989; Eck, et al., 1992; Karpusas, et al., 1995; Cha, et al; 1999) were superimposed on sTALL-1 by the program Dali (Holm and Sander, 1993). To search possible "flap" regions in other members, the sequences that span β strands D and E from the five structures were aligned based on the structural superimpositions. The hydrophobic pattern was obvious in this region after alignments (data not shown). For example, residues Met208 and Ile212 on strand D must be hydrophobic for the proper formation of the hydrophobic core. A similar situation exists for residues Leu229 and Phe230 on strand E. All other family members with unknown structures were aligned according to this pattern (data not shown).

From the alignment results, it is obvious that the loop region connecting β strands D and E is diverse. sTALL-1 has the longest sequence in this region. It is not clear whether any other member will form the "flap" region as in sTALL-1. Further structural, functional, and analysis of solution properties for each individual family member will be necessary.

The fact that other family members bind receptors with three or more CRDs, the possibility of virus-like clusters as the functional unit may be limited. This does not exclude the possibility of weak trimer-trimer interaction for functional purpose. If the "flap" exists for functional purposes in other family members, it is possible that only CRD1 of their cognate receptors takes part in the recognition. One interesting observation is that there is a complementary region in receptors of TNFβ and TRAIL that interacts with this region in a fashion similar to the trimer-trimer interactions of sTALL-1. Therefore, it is possible that this region may mediate intermolecular interactions in vivo, and the corresponding receptor may compete for binding to this region.

Example 6

The following example demonstrates the structure determination of sTALL-1 complexed with eBCMA and eBAFF-R.

Protein Expression, Purification and Crystallization

Protein expression, purification, and crystallization for sTALL-1 is as described in Example 1. BAFF-R/BR3 is cloned according to the published reports (Thompson et al., 2001, supra; Yan et al., 2001, supra). The extracellular domains of BCMA and BAFF-R used for the experiments were overexpressed as GST fusion protein on pGEX4T-2 vector in the BL-21 strain (Example 1). Cell preparation and protein purification procedure are similar to that of sTALL-1. Briefly, harvest cells were broken through a French press and low speed spin. The soluble fraction was loaded onto a GST affinity beads. After intensive wash with binding buffer, thrombin was added for 24 hrs incubation. The supernatants containing the extracellular domain of BCMA or BAFF-R were loaded onto a MonoQ column and eluted with NaCl gradient. The protein is above 99% pure after MonoQ.

Structure Determination and Refinement

For complex crystal preparations, sTALL-1 crystals were harvested after two weeks. sTALL-1 crystals were transferred to a stable soaking solution, which contains 40% dioxane, 1 mM correspondent receptors with 100 mM Bicine pH 9.0. After overnight soaking, crystals were transferred to the same cryo-protectant buffer system for sTALL-1 crystals (Example 1).

Data sets for both complexes were first collected on the house x-ray generator. Crystals of complexes both diffract to 3.0 Å. A 2.6 Å data set of eBCMA and sTALL-1 complex were collected at APS. All data were processed by DENZO package (Otwinowski et al., 1997, *Methods Enzymol* 276: 307-326). Structures of the complexes were solved by fourier difference using the sTALL-1 model (Example 1). After one run of minimization of sTALL-1 model in CNS (Brunger et al., 1998, supra) with new data sets, 2Fo-Fc and Of-Fc maps were calculated. Models were built in O (Jones et al., 1991, *Acta Cryst. A*47:110-119), and finally refined in CNS.

Discussion of Results

Crystals of the soluble portion of TALL-1 (sTALL-1) with extracellular domains of BCMA (eBCMA) and BAFF-R (eBAFF-R) were obtained by diffusing the receptor fragments into the sTALL-1 crystals (see above). The structures of both complexes were determined by Difference Fourier using the available sTALL-1 model (FIGS. 6A-6C and Table 1B). The structure of sTALL-1 with eBCMA has been refined to an R-factor of 20.9% ($R_{free}$-factor of 23.4%) against data extending to 2.6 Å resolution in space group P6₃22, with ten sTALL-1 monomers and seven entire and one partial eBCMA molecules in the asymmetric unit (unit cell of 234×234×217 Å) (Table 1B). Due to crystal packing, another two receptor binding sites were left unoccupied. Similar results are true for the sTALL-1 and eBAFF-R complex with a final resolution of 3.0 Å (Table 1B). The current model of the eBCMA monomer contains residues 5 to 43 (FIG. 6B). The model of the eBAFF-R monomer contains residues 16 to 58 (FIG. 6C). All figures are prepared by RIBBON (Carson, M. Ribbon models of macromolecules. *J. Mol. Graphics* 5, 103-106 (1987).

Structure of eBAFF-R

To the present inventors' surprise, eBAFF-R has similar fold as eBCMA, although it is predicted that eBAFF-R contains only one C2 or X2 module (Thompson et al., 2001, supra; Yan et al., 2001, supra; Bodmer et al., 2002, supra) (FIG. 6C). The structure of eBAFF-R shows that it also con-

TABLE 1B

Experimental data on crystal structure determination and refinement

| Data Set | Resolution (Å) | $R_{merge}$ (%) | No. of unique reflections | Total Observations | Completeness (%) | R-factor | Free R-Factor |
|---|---|---|---|---|---|---|---|
| BCMA | 2.6 | 12.9 | 97672 | 1056950 | 94.0 | 20.9 | 23.5 |
| BAFF-R | 3.0 | 13.8 | 63376 | 318144 | 93.3 | 24.5 | 26.1 |

$R_{merge} = \Sigma |I_j - <I>|/\Sigma I_j$ with Bijvoet pairs treated as equivalent.
Total observations, the number of full and partial observations measured with non-negative intensity to the indicates resolution.
Completeness, the percentage of possible unique reflections measured with $I/\sigma(I) \geq 0$ to the indicated resolution
R-factor = $\Sigma |F_O - F_C|/\Sigma F_0$ for all amplitudes with $F/\sigma(F) \geq 0$ measured; the free R-factor is calculated with 5% of the data.

Overall Structure

The space group of the TALL-1 crystals remained P6$_3$22 with the same cell dimensions with or without bindings of the receptors. There are two virus-like clusters in one unit cell. Each cluster has 60 copies of sTALL-1, 42 fully occupied eBCMA or eBAFF-R, 6 partial copies of eBCMA or eBAFF-R. There are 12 copies of sTALL-1 free of receptors due to crystal packing. All receptors are located on the outer-extreme shell, which expands the ball-like shell another ~20 Å in each direction. The overall arrangement of the receptors on the shell looks like a sunflower with receptors as flower petals and sTALL-1 as a seed bed (FIG. 7A-7D). Molecules marked red are missing in the complex structure. Molecules marked blue are partially occupied. The conformational change in sTALL-1 is negligible before or after receptor binding, which is the only similarity between this interaction and that of other TNF family members.

Structure of eBCMA

As predicted, eBCMA contains two modules, one is A1 module consisting of three beta strands with strand 1 and strand 3 linked by the only disulfide bridge (Naismith et al., 1998, supra). The other module is C2-like (the two disulfide bridges formed as CysI-CysIV and CysII-CysIII), but the disulfide arrangement is the same as a typical of B2 module (the two disulfide bridges formed as CysI-CysIII and CysII-CysIV) (Naismith et al., 1998, supra) (FIG. 6B). For clarity, the present inventors temporarily termed it D2 for its difference from C2 and B2. There are two short helices in the D2 module that are located just at the N-terminus and the C-terminus the module, one is from CysI to CysII and another one is from CysIII to CysIV. The latter helix extends further after the disulfide bridge and forms a 4 turns-long helix, which is unique when compared to all known TNF receptor structures. The arrangement of A1 and D2 of eBCMA is similar to that of A1 and C2 in TNF-R1 (Naismith et al., 1998, supra), A1 and D2 form a saddle-like architecture with each module as half of the saddle and the unique helix as the "rider" (FIG. 6B). From the initial 2Fo-Fc and Fo-Fc maps, all seven copies of A1 modules are very rigid with temperature factors similar to that of sTALL-1, and most side-chains are ordered. Interestingly, the partial copy of the eighth eBCMA only contains the A1 module. The RSMD is 0.2 Å of eight A1 modules in the asymmetry unit. In contrast, the D2 modules are relatively flexible, especially the region between CysII and CysIII. The RSMD is 1.5 Å of the seven D2 modules in the asymmetry unit. The eighth D2 is almost completely disordered except for the region between CysI to CysII.

tains two modules, A1 and the C2-like modules. The A1 module contains three cysteines, only two of them (Cys19 and Cys32) form the typical disulfide bridge. Interestingly, the C2-like module in eBAFF-R only contains one cysteine and it is impossible for it to form disulfide bridges. From the initial 2Fo-fc and Fo-Fc maps, the inventors did find some connecting density at the equivalent CysI-CysIII and CysII-CysIV disulfide bridge positions in the D2 module of eBCMA. Actually, this density represents a H-bond formed between the only Cys35 (location CysI) and the side chain of Ser49 at the equivalent location as the CysIII in eBCMA. Similarly, the Arg39 at the equivalent location CysII forms a H-bond with the oxygen of the main chain of Ala52 at the equivalent location CysIV in eBCMA. These two hydrogen bonds replace the two disulfide bridges in the D2 module of eBCMA, so we termed this module in eBAFF-R as D0. Although the distance between the free Cys24 in A1 and the one (Cys35) in D0 are ideal for disulfide bridge formation (6.5 Å), the side chain orientation of the former cysteine is away from the latter cysteine due to the main chain constraint. Except for what is discussed above, all other structure features are highly similar as described for eBCMA in previous section.

Comparison of eBCMA with eBAFF-R

The sequence homology between eBCMA and eTACI (extracellular domain of TACI) is obvious. This is not true for eBCMA and eBAFF-R or between eTACI and eBAFF-R. The structures of eBCMA and eBAFF-R allowed us to perform a structural based sequence alignment of eBCMA, eBAFF, and eTACI. The inventors found that a strong pattern of similarity emerges (FIGS. 8A-8B). As mentioned above, eBCMA and eBAFF-R have a similar saddle-like fold, the RMSD between two equivalent and best defined structures from each group is 1.9 Å. (FIG. 8A). A1 modules from eBCMA and eBAFF-R (with RMSD 0.5 Å) are almost identical judged by both primary sequence alignment and structure superposition (FIGS. 8A-8B). The D2 from BCMA and D0 from BAFF-R are also very similar structurally, although the sequence similarity is poor.

The high sequence similarities between the two CRDs in TACI and CRDs in BCMA or BAFF-R lead the present inventors to predict that each CRD of TACI contains one A1 module and one D2 module. Interestingly, another TNF receptor member Fn14, which also just contains one CRD, was predicted to contain one A1 module and one C2 module (Bodmer et al., 2002, supra). From the sequence alignment result presented herein, it could contain either D2 or C2 (FIG. 8B). In any event, without being bound by theory, the present inventors propose that the interaction mode between Fn14 and its ligand TWEAK are similar to what they found in the complexes of eBCMA and eBAFF-R with sTALL-1 (see below).

Interactions of sTALL-1 and eBCMA

The interactions between sTALL-1 and eBCMA are mostly in a one to one mode, that is one monomer of the receptor to one monomer of the ligand. The slightly tilted saddle-like receptor is sitting on a horseback-like groove, which is formed by four loops from the ligand, two (connection regions for strands GH and A'A) at one side and two (connection regions for strands CD and EF) at the other (FIGS. 9A-9C). This mode of interaction is dramatically different from that seen within other TNF family members, in which one elongated receptor binds to the cleft formed by two ligands. The interactions of eBCMA with sTALL-1 include hydrogen bonds, salt bridges, and, most importantly, hydrophobic contacts. There are 21 total residues involved, 9 from eBCMA (Tyr13, Asp 15, Leu 17, Leu 18, His19, Ile22, Leu26, Arg27, and Pro34), 8 from the primary ligand (Tyr163, Tyr206, Leu211, Arg231, Ile233, Pro264, Arg265, Glu266), and 4 from the second ligand (Leu200, Leu240, Asp273, Asp275) of the trimer (FIG. 9D). The overall interactions can be divided into four groups.

First, Leu17, Leu18 from eBCMA, and Tyr163, Leu211, Ile233, Pro264 from the primary ligand, and Leu200 from the second ligand form the first hydrophobic core. Interestingly, Tyr163, Leu200, Ile233, and Pro264 are located on a curved track, the joining of Leu17 from eBCMA makes a perfect hydrophobic curved track, just like a key and lock pair. Leu211 from the primary ligand and Leu 18 from eBCMA further strengthen the contacts (FIG. 9E).

Second, Ile22, Leu26 from eBCMA, Tyr206 from the primary ligand, and Leu240 from the second ligand form the second hydrophobic core (FIG. 9F).

Third, Asp15 from eBCMA and Arg265 from the primary ligand forms one salt bridge, and Arg27 from eBCMA and Glu266 from the primary ligand forms another. It is also possible that there is a hydrogen bond between Tyr206 from the primary ligand and Tyr13 from the eBCMA (FIG. 9G).

Fourth, His19 from eBCMA, forms a water mediated interactions with Asp 273, Asp275 from the second ligand.

Interactions of sTALL-1 and eBAFF-R

The interactions between sTALL-1 and eBAFF-R are similar to those between sTALL-1 and eBCMA, although details are slightly different. The interactions also include hydrogen bonds, salt bridges, and hydrophobic contacts. There are totally 22 residues involved, 9 from eBAFF-R (Asp26, Leu28, Val29, Arg30, Val33, Leu37, Leu38, and Arg42, and Pro45), 8 from the primary ligand (Tyr163, Tyr206, Leu211, Arg 231, Ile233, Glu238, Pro264, Arg265), 4 from the second ligand (Leu200, Leu240, Asp273, Asp275), and one from a flap region of the neighboring trimer (Asp222) (FIG. 9H). The overall interactions also can be divided into four groups.

First, Leu28, Val29 from eBAFF-R, Tyr163, Leu211, Ile233, Pro264 from the primary ligand, and Leu200 from the second ligand form the first hydrophobic core. Compared to eBCMA, Val29 in eBAFF-R replace the equivalent Leu 18. The side-chain is shortened, and this could reduce the strength of the contact.

Second, Val33, Leu37, Leu38 and Pro45 from eBAFF-R, Tyr206 from the primary ligand, and Leu240 from the second ligand form the second hydrophobic core (FIG. 9I). Val33 in eBCMA is Ile22. Leu38 is additional for eBAFF-R.

Third, Asp26 from eBCMA and Arg265 from the primary ligand form a salt bridge. The replacement of Arg27 in eBCMA with Leu38 in eBAFF-R eliminates a salt bridge with Glu266 from the primary ligand. However, there is one new salt bridge between Arg42 from eBAFF-R and Glu238 from the primary ligand.

Fourth, Arg30 from eBAFF-R, Arg231 from the primary ligand, Asp 273, Asp275 from the second ligand, and Asp222 from the third ligand (from the neighboring trimer) form a complicated salt bridge network (FIG. 9J). The long side chain of Arg30 from eBAFF-R (His19 in eBCMA) is in a position to make contacts with either Asp275 or Asp222. The well-defined electron density of the Arg30 side chain from eBAFF-R in the initial difference maps suggests that these are strong interactions, that might considerably strengthen the eBAFF-R and sTALL-1 binding.

Structural Basis of BAFF-R Discriminating Between April and TALL-1

Two publications that initially reported the cloning of BAFF-R/BR3 receptor claimed that BAFF-R specifically binds to TALL-1 but not APRIL/TALL-2 (Thompson et al., 2001, supra; Yan et al., 2001, supra). Furthermore, APRIL has very low abundance in all tissues, and was proposed to be dispensable for B-cell maturation (Hahne et al., 1998, *J. Exp. Med.* 188:1185-1190; Schneider et al., 2001, *J. Exp. Med.* 194:1691-1697). It was also predicted that there may be an additional and more specific receptor for APRIL (Ware et al., 2000, *J. Exp. Med.* 192:F35-37. The binding affinity of APRIL to BCMA and TACI are similar to that of TALL-1 to BCMA and TACI (Yu et al., 2000, *Nature immunol.* 1:252-256). From the above structural analysis, eBCMA and eBAFF-R have nearly identical three-dimensional structure. Furthermore, the interactions between eBCMA and sTALL-1 are also highly conserved in the interactions between eBAFF-R and sTALL-1. Without being bound by theory, the present inventors propose that these interactions are also conserved for TACI and sTALL-1. Given these structural similarities, one can investigate begin to investigate how BAFF-R can discriminate between TALL-1 and APRIL.

APRIL was modeled based on the sTALL-1 structure, benefiting from the high primary sequence homology between TALL-1 and APRIL (Shu et al., 1999, supra). The most obvious difference between sTALL-1 and APRIL is in the "flap" region (6 residues) of sTALL-1, which is missing in APRIL (Shu et al., 1999, supra). In Example 3, the inventors described a mutated version of sTALL-1 with 8 residues replaced by two glycine residues, which was not functional in transfection assays or in the B-cell stimulation assays, but had a binding affinity to its receptors similar to that of the native sTALL-1. The structure of this mutated sTALL-1 has been determined at 1.7 Å resolution by MIR method by the present inventors, and is almost identical to the sTALL-1 except missing the flap (Liu and Zhang, unpublished). This mutated sTALL-1 is a close model of APRIL.

The final built model of APRIL was imported to the minimization program in CNS (Brunger et al., 1998, *Acta. Cryst.* D54:905-921). The output coordinates were superimposed on the sTALL-1 structure (FIG. 10A). Detailed interactions of eBAFF-R and APRIL were briefly analyzed. All residues from eBAFF-R that are involved in the interactions between the eBAFF-R and sTALL-1 are displayed (FIG. 10B). All equivalent residues in APRIL, which are close to the receptor binding surface in sTALL-1 are also showed (FIG. 10B). To the present inventors' surprise, the interactions are extremely similar to those found in the complexes of eBCMA or eBAFF-R with sTALL-1. First, the first hydrophobic core that was described in the two previous complexes still exists, including residues, Leu28, Val29 from the eBAFF-R and residues, Val133, Thr177, Val181, Ile197, Pro230 from the primary APRIL molecule, and residues Leu170, Tyr208 from the secondary APRIL. The Tyr208 is additional for APRIL, which may strengthen the hydrophobic contact (FIG. 10B). Second, the second hydrophobic core consists of residues Val33, Leu37, Leu38, Pro45 from the eBAFF-R, residue Phe176 from the primary ligand, and residue Arg206 from the secondary ligand. Compared to the interactions between eBAFF-R and sTALL-1, Tyr206 from the primary ligand is changed to Phe176. Leu240 from the second ligand is changed to Arg206. The former change could also strengthen the hydrophobic contacts (FIG. 10B). Third, the major salt bridge formed by residue Asp26 from the receptor and residue Arg231 from APRIL is conserved (not shown). These comparisons have lead the present inventors to conclude, without being bound by theory, that APRIL could be able, at least under some conditions, to bind to BAFF-R, which is contradictory to previous reports (Thompson et al., 2001, supra; Yan et al., 2001, supra).

To test these predictions, the binding affinity of eBAFF-R for the sTALL-1 versus APRIL was determined using BIA-Core surface plasmon resonance. To obtain the true affinity of the receptor without the compounding effect of multivalent binding, the polyvalent sTALL-1 proteins and APRIL were immobilized in the instrument flow cells and soluble monomeric eBAFF-R and eBCMA were injected in the mobile phase. The kds of the interaction were calculated from the kinetic binding data (data not shown). To avoid nonspecific binding, the inventors analyzed a series of binding curves at pH7.5, pH8.0, pH8.5, and pH9.0. To the inventors' surprise, it was discovered that eBAFF-R only binds APRIL at pH8.5 or higher, and the binding affinity increases coupled with pH increasing (data not shown). To address the new property of eBAFF-R binding to APRIL, a serial truncation, a point mutation, and a combination of the two were introduced (data not shown). All protein versions with these mutations were subjected to BIAcore binding assays. The inventors only found two versions of eBAFF-R mutations to have significant binding affinity to APRIL at pH7.5; they are (1) residues 12-62 (SEQ ID NO:8) (substitutions at R30H, H31A), and (2) residues 12-62 (SEQ ID NO:8) (substitutions at V29L, V33I) respectively. The rationale for the first version is that the highly positive charged N-terminal of eBAFF-R and Arg30 prevent eBAFF-R from binding to APRIL, which also has a high positive charge on its surface, based on the present inventors' model and others, with a predicted PI of 9.4. Interestingly, the homologues with only a 1 to 12 truncation or only a R30H, H31A double mutation, do not change the binding property. For the second version, which partially mimics eBCMA (although Arg30-His31 is still in the version), the inventors believe, without being bound by theory, that strong hydrophobic interaction forces introduced by the long side-chain of Leu and Ile overcome the inhibitory role of Arg30-His31 (data not shown). Interestingly, eBCMA loses binding affinity to APRIL at pH6.0 (data not shown). These data further suggested that positively charged His19 (equivalent to position Arg30 of eBAFF-R) also plays an inhibitory role for the binding of eBCMA to APRIL.

The inventors have speculated that APRIL could play a decoy ligand role. These current data show that eBAFF-R does not bind to APRIL at normal physiological conditions (at pH7.5), and so the mechanism of APRIL competitively binding with TALL-1 for BAFF-R binding is not expected to be true under normal physiological conditions. From the modeling results, the inventors found that residues that are involved in trimerization are absolutely conserved (data not shown). This information suggested if TALL-1 and APRIL are expressed in the same environment and at the same time, they could form heterotrimers. It has turned out to be true that patients with autoimmune diseases have detectable heterotrimers of TALL-1 and APRIL. As the inventors have concluded previously herein, sTALL-1 trimers alone (e.g., absent clustering of trimers) can not trigger the signal transduction of its cognate receptors. Heterotrimers of TALL-1 and APRIL could not form the virus-like cluster as sTALL-1 alone due to the lack of the "flap" region in APRIL. Considering the fact that overexpression of TALL-1 could lead to the abnormal stimulation of B-cell and finally the development of autoimmune disease, APRIL may be serving as a balancer, reducing the opportunity for sTALL-1 to form the active cluster. This role is similar to the decoy death receptors, which are essential for cells to survive ((Cha et al., 1999, *Immunity* 11:253-261; Mongkolsapaya et al., 1999, *Nat. Struct. Biol.* 6:1048-1053; Hymowitz et al., 1999, *Mol. Cell.* 4:563-571). Finally, knock-out data for APRIL showed that mice die at early embryonic stages, which indirectly suggests an important role of APRIL (Mackay et al., 2002, *TRENDS in Immunology* 23:113-115).

In this example, two novel structural modules of TNF receptors (D2 and D0) are revealed from the structures of sTALL-1 complexed with eBCMA and with eBAFF-R. The interaction modes of the eBCMA and eBAFF-R with sTALL-1 are completely different from those found in the other TNF family members, containing at least two CRDs that bind to the cleft regions formed by two ligands. For the interactions described here, one saddle-like receptor mostly makes a one to one interaction with its ligand at the extreme end of the ligand. The difference exists not only in the CRD structure but also in the binding locations and modes. The structural based sequence alignment indicates that similar interaction modes may also exist in the interaction between Fn14 to TWEAK, another TNF family couple. Furthermore, modeling analysis contributes to the proposal that APRIL could be a critical decoy ligand functioning in a similar way to the decoy death receptors.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method to inhibit TALL-1 biological activity in a mammal, comprising administering to said mammal a TALL-1 antagonist protein, wherein said protein comprises an amino acid sequence that differs from positions 134 to 285 of SEQ ID NO:2 by at least one modification in the region connecting β strands D and E that reduces the biological activity of the TALL-1 antagonist as compared to wild-type TALL-1 wherein the modification comprises a deletion of the following amino acid residues Val217, His218, Val219, Phe220, Gly221, Asp222, Glu223 and Leu224.

2. The method of claim 1, wherein said protein is a competitive inhibitor of wild-type TALL-1 for binding to a TALL-1 receptor.

3. The method of claim 1, wherein the mammal has, or is at risk of developing, a disease or condition associated with hyperactive B cell development or B cell hyperproliferation.

4. The method of claim 1, wherein the mammal has, or is at risk of developing, a disease or condition characterized by increased numbers of mature B-lymphocytes, splenomegaly, anti-DNA antibodies, proteinuria, or glomerulonephritis.

5. The method of claim 4, wherein said disease is systemic lupus erythematosus.

6. A method to inhibit TALL-1 biological activity in a mammal, comprising administering to said mammal a TALL-1 antagonist protein, wherein said protein comprises an amino acid sequence that differs from positions 134 to 285 of SEQ ID NO:2 by:

a) at least one modification in the region connecting β strands D and E wherein the modification comprises a deletion of the following amino acid residues Val217, His218, Val219, Phe220, Gly221, Asp222, Glu223 and Leu224; and b) a modification of at least one amino acid residue selected from the group consisting of: Gln144, Ile150, Leu169, Phe172, Tyr192, Phe194, Tyr196, Lys216, Val227, Leu229, Tyr246, Ile250, Lys252, Glu254, Leu282, and Leu285;

wherein said modification reduces the biological activity of the TALL-1 antagonist as compared to wild-type TALL-1.

7. The method of claim 6, wherein said modification of at least one amino acid residue is selected from the group consisting of: Phe194, Tyr196, Tyr246, Leu282, Gln144 and Leu285.

8. The method of claim 6, wherein said protein is a competitive inhibitor of wild-type TALL-1 for binding to a TALL-1 receptor.

9. The method of claim 6, wherein the mammal has, or is at risk of developing, a disease or condition associated with hyperactive B cell development or B cell hyperproliferation.

10. The method of claim 6, wherein the mammal has, or is at risk of developing, a disease or condition characterized by increased numbers of mature B-lymphocytes, splenomegaly, anti-DNA antibodies, proteinuria, or glomerulonephritis.

11. The method of claim 6, wherein said disease is systemic lupus erythematosus.

* * * * *

SEQUENCE LISTING

```
<160> NUMBER OF SEQ ID NOS: 16

<210> SEQ ID NO 1
<211> LENGTH: 858
<212> TYPE: DNA
<213> ORGANISM: Homo sapiens
<220> FEATURE:
<221> NAME/KEY: CDS
```

<222> LOCATION: (1)..(858)

<400> SEQUENCE: 1

```
atg gat gac tcc aca gaa agg gag cag tca cgc ctt act tct tgc ctt       48
Met Asp Asp Ser Thr Glu Arg Glu Gln Ser Arg Leu Thr Ser Cys Leu
1               5                   10                  15 aag aaa aga gaa gaa atg aaa ctg aag gag tgt gtt tcc atc ctc cca       96
Lys Lys Arg Glu Glu Met Lys Leu Lys Glu Cys Val Ser Ile Leu Pro
            20                  25                  30 cgg aag gaa agc ccc tct gtc cga tcc tcc aaa gac gga aag ctg ctg      144
Arg Lys Glu Ser Pro Ser Val Arg Ser Ser Lys Asp Gly Lys Leu Leu
        35                  40                  45 gct gca acc ttg ctg ctg gca ctg ctg tct tgc tgc ctc acg gtg gtg      192
Ala Ala Thr Leu Leu Leu Ala Leu Leu Ser Cys Cys Leu Thr Val Val
    50                  55                  60 tct ttc tac cag gtg gcc gcc ctg caa ggg gac ctg gcc agc ctc cgg      240
Ser Phe Tyr Gln Val Ala Ala Leu Gln Gly Asp Leu Ala Ser Leu Arg
65                  70                  75                  80 gca gag ctg cag ggc cac cac gcg gag aag ctg cca gca gga gca gga      288
Ala Glu Leu Gln Gly His His Ala Glu Lys Leu Pro Ala Gly Ala Gly
                85                  90                  95 gcc ccc aag gcc ggc ttg gag gaa gct cca gct gtc acc gcg gga ctg      336
Ala Pro Lys Ala Gly Leu Glu Glu Ala Pro Ala Val Thr Ala Gly Leu
            100                 105                 110 aaa atc ttt gaa cca cca gct cca gga gaa ggc aac tcc agt cag aac      384
Lys Ile Phe Glu Pro Pro Ala Pro Gly Glu Gly Asn Ser Ser Gln Asn
        115                 120                 125 agc aga aat aag cgt gcc gtt cag ggt cca gaa gaa aca gtc act caa      432
Ser Arg Asn Lys Arg Ala Val Gln Gly Pro Glu Glu Thr Val Thr Gln
    130                 135                 140 gac tgc ttg caa ctg att gca gac agt gaa aca cca act ata caa aaa      480
Asp Cys Leu Gln Leu Ile Ala Asp Ser Glu Thr Pro Thr Ile Gln Lys
145                 150                 155                 160 gga tct tac aca ttt gtt cca tgg ctt ctc agc ttt aaa agg gga agt      528
Gly Ser Tyr Thr Phe Val Pro Trp Leu Leu Ser Phe Lys Arg Gly Ser
                165                 170                 175 gcc cta gaa gaa aaa gag aat aaa ata ttg gtc aaa gaa act ggt tac      576
Ala Leu Glu Glu Lys Glu Asn Lys Ile Leu Val Lys Glu Thr Gly Tyr
            180                 185                 190 ttt ttt ata tat ggt cag gtt tta tat act gat aag acc tac gcc atg      624
Phe Phe Ile Tyr Gly Gln Val Leu Tyr Thr Asp Lys Thr Tyr Ala Met
        195                 200                 205 gga cat cta att cag agg aag aag gtc cat gtc ttt ggg gat gaa ttg      672
Gly His Leu Ile Gln Arg Lys Lys Val His Val Phe Gly Asp Glu Leu
    210                 215                 220 agt ctg gtg act ttg ttt cga tgt att caa aat atg cct gaa aca cta      720
Ser Leu Val Thr Leu Phe Arg Cys Ile Gln Asn Met Pro Glu Thr Leu
225                 230                 235                 240 ccc aat aat tcc tgc tat tca gct ggc att gca aaa ctg gaa gaa gga      768
Pro Asn Asn Ser Cys Tyr Ser Ala Gly Ile Ala Lys Leu Glu Glu Gly
                245                 250                 255 gat gaa ctc caa ctt gca ata cca aga gaa aat gca caa ata tca ctg      816
Asp Glu Leu Gln Leu Ala Ile Pro Arg Glu Asn Ala Gln Ile Ser Leu
            260                 265                 270 gat gga gat gtc aca ttt ttt ggt gca ttg aaa ctg ctg tga             858
Asp Gly Asp Val Thr Phe Phe Gly Ala Leu Lys Leu Leu
        275                 280                 285
```

<210> SEQ ID NO 2
<211> LENGTH: 285
<212> TYPE: PRT

<213> ORGANISM: Homo sapiens

<400> SEQUENCE: 2

```
Met Asp Asp Ser Thr Glu Arg Glu Gln Ser Arg Leu Thr Ser Cys Leu
1               5                   10                  15
Lys Lys Arg Glu Glu Met Lys Leu Lys Glu Cys Val Ser Ile Leu Pro
            20                  25                  30
Arg Lys Glu Ser Pro Ser Val Arg Ser Ser Lys Asp Gly Lys Leu Leu
        35                  40                  45
Ala Ala Thr Leu Leu Leu Ala Leu Leu Ser Cys Cys Leu Thr Val Val
    50                  55                  60
Ser Phe Tyr Gln Val Ala Ala Leu Gln Gly Asp Leu Ala Ser Leu Arg
65                  70                  75                  80
Ala Glu Leu Gln Gly His His Ala Glu Lys Leu Pro Ala Gly Ala Gly
                85                  90                  95
Ala Pro Lys Ala Gly Leu Glu Glu Ala Pro Ala Val Thr Ala Gly Leu
            100                 105                 110
Lys Ile Phe Glu Pro Pro Ala Pro Gly Glu Gly Asn Ser Ser Gln Asn
        115                 120                 125
Ser Arg Asn Lys Arg Ala Val Gln Gly Pro Glu Glu Thr Val Thr Gln
    130                 135                 140
Asp Cys Leu Gln Leu Ile Ala Asp Ser Glu Thr Pro Thr Ile Gln Lys
145                 150                 155                 160
Gly Ser Tyr Thr Phe Val Pro Trp Leu Leu Ser Phe Lys Arg Gly Ser
                165                 170                 175
Ala Leu Glu Glu Lys Glu Asn Lys Ile Leu Val Lys Glu Thr Gly Tyr
            180                 185                 190
Phe Phe Ile Tyr Gly Gln Val Leu Tyr Thr Asp Lys Thr Tyr Ala Met
        195                 200                 205
Gly His Leu Ile Gln Arg Lys Lys Val His Val Phe Gly Asp Glu Leu
    210                 215                 220
Ser Leu Val Thr Leu Phe Arg Cys Ile Gln Asn Met Pro Glu Thr Leu
225                 230                 235                 240
Pro Asn Asn Ser Cys Tyr Ser Ala Gly Ile Ala Lys Leu Glu Glu Gly
                245                 250                 255
Asp Glu Leu Gln Leu Ala Ile Pro Arg Glu Asn Ala Gln Ile Ser Leu
            260                 265                 270
Asp Gly Asp Val Thr Phe Phe Gly Ala Leu Lys Leu Leu
        275                 280                 285
```

<210> SEQ ID NO 3
<211> LENGTH: 753
<212> TYPE: DNA
<213> ORGANISM: Homo sapiens
<220> FEATURE:
<221> NAME/KEY: CDS
<222> LOCATION: (1)..(753)

<400> SEQUENCE: 3

```
atg cca gcc tca tct cct ttc ttg cta gcc ccc aaa ggg cct cca ggc      48
Met Pro Ala Ser Ser Pro Phe Leu Leu Ala Pro Lys Gly Pro Pro Gly
1               5                   10                  15 aac atg ggg ggc cca gtc aga gag ccg gca ctc tca gtt gcc ctc tgg      96
Asn Met Gly Gly Pro Val Arg Glu Pro Ala Leu Ser Val Ala Leu Trp
            20                  25                  30 ttg agt tgg ggg gca gct ctg ggg gcc gtg gct tgt gcc atg gct ctg     144
Leu Ser Trp Gly Ala Ala Leu Gly Ala Val Ala Cys Ala Met Ala Leu
        35                  40                  45
```

| | |
|---|---|
| ctg acc caa caa aca gag ctg cag agc ctc agg aga gag gtg agc cgg<br>Leu Thr Gln Gln Thr Glu Leu Gln Ser Leu Arg Arg Glu Val Ser Arg<br>50                       55                   60 | 192 |
| ctg cag ggg aca gga ggc ccc tcc cag aat ggg gaa ggg tat ccc tgg<br>Leu Gln Gly Thr Gly Gly Pro Ser Gln Asn Gly Glu Gly Tyr Pro Trp<br>65                        70                     75                 80 | 240 |
| cag agt ctc ccg gag cag agt tcc gat gcc ctg gaa gcc tgg gag aat<br>Gln Ser Leu Pro Glu Gln Ser Ser Asp Ala Leu Glu Ala Trp Glu Asn<br>                    85                         90                       95 | 288 |
| ggg gag aga tcc cgg aaa agg aga gca gtg ctc acc caa aaa cag aag<br>Gly Glu Arg Ser Arg Lys Arg Arg Ala Val Leu Thr Gln Lys Gln Lys<br>                  100                     105                    110 | 336 |
| aag cag cac tct gtc ctg cac ctg gtt ccc att aac gcc acc tcc aag<br>Lys Gln His Ser Val Leu His Leu Val Pro Ile Asn Ala Thr Ser Lys<br>                  115                     120                    125 | 384 |
| gat gac tcc gat gtg aca gag gtg atg tgg caa cca gct ctt agg cgt<br>Asp Asp Ser Asp Val Thr Glu Val Met Trp Gln Pro Ala Leu Arg Arg<br>130                       135                    140 | 432 |
| ggg aga ggc cta cag gcc caa gga tat ggt gtc cga atc cag gat gct<br>Gly Arg Gly Leu Gln Ala Gln Gly Tyr Gly Val Arg Ile Gln Asp Ala<br>145                       150                    155                    160 | 480 |
| gga gtt tat ctg ctg tat agc cag gtc ctg ttt caa gac gtg act ttc<br>Gly Val Tyr Leu Leu Tyr Ser Gln Val Leu Phe Gln Asp Val Thr Phe<br>                  165                     170                    175 | 528 |
| acc atg ggt cag gtg gtg tct cga gaa ggc caa gga agg cag gag act<br>Thr Met Gly Gln Val Val Ser Arg Glu Gly Gln Gly Arg Gln Glu Thr<br>                  180                     185                    190 | 576 |
| cta ttc cga tgt ata aga agt atg ccc tcc cac ccg gac cgg gcc tac<br>Leu Phe Arg Cys Ile Arg Ser Met Pro Ser His Pro Asp Arg Ala Tyr<br>                  195                     200                    205 | 624 |
| aac agc tgc tat agc gca ggt gtc ttc cat tta cac caa ggg gat att<br>Asn Ser Cys Tyr Ser Ala Gly Val Phe His Leu His Gln Gly Asp Ile<br>210                       215                    220 | 672 |
| ctg agt gtc ata att ccc cgg gca agg gcg aaa ctt aac ctc tct cca<br>Leu Ser Val Ile Ile Pro Arg Ala Arg Ala Lys Leu Asn Leu Ser Pro<br>225                       230                    235                    240 | 720 |
| cat gga acc ttc ctg ggg ttt gtg aaa ctg tga<br>His Gly Thr Phe Leu Gly Phe Val Lys Leu<br>                  245                     250 | 753 |

<210> SEQ ID NO 4
<211> LENGTH: 250
<212> TYPE: PRT
<213> ORGANISM: Homo sapiens

<400> SEQUENCE: 4

Met Pro Ala Ser Ser Pro Phe Leu Leu Ala Pro Lys Gly Pro Pro Gly
1               5                   10                  15

Asn Met Gly Gly Pro Val Arg Glu Pro Ala Leu Ser Val Ala Leu Trp
            20                  25                  30

Leu Ser Trp Gly Ala Ala Leu Gly Ala Val Ala Cys Ala Met Ala Leu
        35                  40                  45

Leu Thr Gln Gln Thr Glu Leu Gln Ser Leu Arg Arg Glu Val Ser Arg
    50                  55                  60

Leu Gln Gly Thr Gly Gly Pro Ser Gln Asn Gly Glu Gly Tyr Pro Trp
65                  70                  75                  80

Gln Ser Leu Pro Glu Gln Ser Ser Asp Ala Leu Glu Ala Trp Glu Asn
                85                  90                  95

Gly Glu Arg Ser Arg Lys Arg Arg Ala Val Leu Thr Gln Lys Gln Lys

```
                        100                 105                 110
Lys Gln His Ser Val Leu His Leu Val Pro Ile Asn Ala Thr Ser Lys
        115                 120                 125

Asp Asp Ser Asp Val Thr Glu Val Met Trp Gln Pro Ala Leu Arg Arg
130                 135                 140

Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
            180                 185                 190

Leu Phe Arg Cys Ile Arg Ser Met Pro Ser His Pro Asp Arg Ala Tyr
        195                 200                 205

Asn Ser Cys Tyr Ser Ala Gly Val Phe His Leu His Gln Gly Asp Ile
        210                 215                 220

Leu Ser Val Ile Ile Pro Arg Ala Arg Ala Lys Leu Asn Leu Ser Pro
225                 230                 235                 240

His Gly Thr Phe Leu Gly Phe Val Lys Leu
                245                 250

<210> SEQ ID NO 5
<211> LENGTH: 995
<212> TYPE: DNA
<213> ORGANISM: Homo sapiens
<220> FEATURE:
<221> NAME/KEY: CDS
<222> LOCATION: (219)..(773)

<400> SEQUENCE: 5
aagactcaaa cttagaaact tgaattagat gtggtattca aatccttacg tgccgcgaag     60
acacagacag cccccgtaag aacccacgaa gcaggcgaag ttcattgttc tcaacattct    120
agctgctctt gctgcatttg ctctggaatt cttgtagaga tattacttgt ccttccaggc    180
tgttctttct gtagctccct tgtttttctt tgtgatc atg ttg cag atg gct ggg    236
                                        Met Leu Gln Met Ala Gly
                                         1               5 cag tgc tcc caa aat gaa tat ttt gac agt ttg ttg cat gct tgc ata    284
Gln Cys Ser Gln Asn Glu Tyr Phe Asp Ser Leu Leu His Ala Cys Ile
         10                  15                  20 cct tgt caa ctt cga tgt tct tct aat act cct cct cta aca tgt cag    332
Pro Cys Gln Leu Arg Cys Ser Ser Asn Thr Pro Pro Leu Thr Cys Gln
     25                  30                  35 cgt tat tgt aat gca agt gtg acc aat tca gtg aaa gga acg aat gcg    380
Arg Tyr Cys Asn Ala Ser Val Thr Asn Ser Val Lys Gly Thr Asn Ala
 40                  45                  50 att ctc tgg acc tgt ttg gga ctg agc tta ata att tct ttg gca gtt    428
Ile Leu Trp Thr Cys Leu Gly Leu Ser Leu Ile Ile Ser Leu Ala Val
55                  60                  65                  70 ttc gtg cta atg ttt ttg cta agg aag ata agc tct gaa cca tta aag    476
Phe Val Leu Met Phe Leu Leu Arg Lys Ile Ser Ser Glu Pro Leu Lys
                 75                  80                  85 gac gag ttt aaa aac aca gga tca ggt ctc ctg ggc atg gct aac att    524
Asp Glu Phe Lys Asn Thr Gly Ser Gly Leu Leu Gly Met Ala Asn Ile
             90                  95                 100 gac ctg gaa aag agc agg act ggt gat gaa att att ctt ccg aga ggc    572
Asp Leu Glu Lys Ser Arg Thr Gly Asp Glu Ile Ile Leu Pro Arg Gly
        105                 110                 115 ctc gag tac acg gtg gaa gaa tgc acc tgt gaa gac tgc atc aag agc    620
Leu Glu Tyr Thr Val Glu Glu Cys Thr Cys Glu Asp Cys Ile Lys Ser
```

| | | | | | | | | | | | | |
|---|---|---|---|---|---|---|---|---|---|---|---|---|
| | 120 | | | 125 | | | | 130 | | | | |
| aaa | ccg | aag | gtc | gac | tct | gac | cat | tgc | ttt | cca | ctc | cca | gct | atg | gag | 668 |
| Lys | Pro | Lys | Val | Asp | Ser | Asp | His | Cys | Phe | Pro | Leu | Pro | Ala | Met | Glu |  |
| 135 | | | | 140 | | | | 145 | | | | 150 | | | | |
| gaa | ggc | gca | acc | att | ctt | gtc | acc | acg | aaa | acg | aat | gac | tat | tgc | aag | 716 |
| Glu | Gly | Ala | Thr | Ile | Leu | Val | Thr | Thr | Lys | Thr | Asn | Asp | Tyr | Cys | Lys |  |
| | | | 155 | | | | 160 | | | | 165 | | | | | |
| agc | ctg | cca | gct | gct | ttg | agt | gct | acg | gag | ata | gag | aaa | tca | att | tct | 764 |
| Ser | Leu | Pro | Ala | Ala | Leu | Ser | Ala | Thr | Glu | Ile | Glu | Lys | Ser | Ile | Ser |  |
| | | 170 | | | | 175 | | | | 180 | | | | | | |
| gct | agg | taa | ttaccattt | cgactcgagc | agtgccactt | taaaaatctt | | | | | | | | | | 813 |
| Ala | Arg | | | | | | | | | | | | | | | | ttgtcagaat agatgatgtg tcagatctct ttaggatgac tgtattttc agttgccgat 873 acagcttttt gtcctctaac tgtggaaact ctttatgtta gatatattc tctaggttac 933 tgttgggagc ttaatggtag aaacttcctt ggtttcatga taaagtctt tttttttcct 993 ga 995

```
<210> SEQ ID NO 6
<211> LENGTH: 184
<212> TYPE: PRT
<213> ORGANISM: Homo sapiens

<400> SEQUENCE: 6
```

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Ser Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180

```
<210> SEQ ID NO 7
<211> LENGTH: 899
<212> TYPE: DNA
<213> ORGANISM: Homo sapiens
<220> FEATURE:
<221> NAME/KEY: CDS
<222> LOCATION: (6)..(560)

<400> SEQUENCE: 7
```

```
gcacc atg agg cga ggg ccc cgg agc ctg cgg ggc agg gac gcg cca gcc        50
      Met Arg Arg Gly Pro Arg Ser Leu Arg Gly Arg Asp Ala Pro Ala
      1               5                   10                  15 ccc acg ccc tgc gtc ccg gcc gag tgc ttc gac ctg ctg gtc cgc cac          98
Pro Thr Pro Cys Val Pro Ala Glu Cys Phe Asp Leu Leu Val Arg His
                20                  25                  30 tgc gtg gcc tgc ggg ctc ctg cgc acg ccg cgg ccg aaa ccg gcc ggg         146
Cys Val Ala Cys Gly Leu Leu Arg Thr Pro Arg Pro Lys Pro Ala Gly
            35                  40                  45 gcc agc agc cct gcg ccc agg acg gcg ctg cag ccg cag gag tcg gtg         194
Ala Ser Ser Pro Ala Pro Arg Thr Ala Leu Gln Pro Gln Glu Ser Val
        50                  55                  60 ggc gcg ggg gcc ggc gag gcg gcg ctg ccc ctg ccc ggg ctg ctc ttt         242
Gly Ala Gly Ala Gly Glu Ala Ala Leu Pro Leu Pro Gly Leu Leu Phe
    65                  70                  75 ggc gcc ccc gcg ctg ctg ggc ctg gca ctg gtc ctg gcg ctg gtc ctg         290
Gly Ala Pro Ala Leu Leu Gly Leu Ala Leu Val Leu Ala Leu Val Leu
80                  85                  90                  95 gtg ggt ctg gtg agc tgg agg cgg cga cag cgg cgg ctt cgc ggc gcg         338
Val Gly Leu Val Ser Trp Arg Arg Arg Gln Arg Arg Leu Arg Gly Ala
                100                 105                 110 tcc tcc gca gag gcc ccc gac gga gac aag gac gcc cca gag ccc ctg         386
Ser Ser Ala Glu Ala Pro Asp Gly Asp Lys Asp Ala Pro Glu Pro Leu
            115                 120                 125 gac aag gtc atc att ctg tct ccg gga atc tct gat gcc aca gct cct         434
Asp Lys Val Ile Ile Leu Ser Pro Gly Ile Ser Asp Ala Thr Ala Pro
        130                 135                 140 gcc tgg cct cct cct ggg gaa gac cca gga acc acc cca cct ggc cac         482
Ala Trp Pro Pro Pro Gly Glu Asp Pro Gly Thr Thr Pro Pro Gly His
    145                 150                 155 agt gtc cct gtg cca gcc aca gag ctg ggc tcc act gaa ctg gtg acc         530
Ser Val Pro Val Pro Ala Thr Glu Leu Gly Ser Thr Glu Leu Val Thr
160                 165                 170                 175 acc aag acg gcc ggc cct gag caa caa tag cagggagccg gcaggaggtg           580
Thr Lys Thr Ala Gly Pro Glu Gln Gln
                180 gcccctgccc tccctctgga cccccagcca ggggcttgga aatcaaattc agctcttcac       640 tccagcatgc acatgccctc tttctgggac caggctaacc ctgcagaagc acagacacta      700 cagaccacag cattcagccc ccatggagtt tggtgtgctt gcctttggct tcagacctca      760 ccatctttga cagcccttga aggtggtagc ccagctcctg ttcctgtgcc ttcaaaaggc      820 tggggcacta tgagtaaaag accgctttta aaatggggaa ggcaccatta agccaaaatg      880 aatctgaaaa aagacaaaa                                                    899

<210> SEQ ID NO 8
<211> LENGTH: 184
<212> TYPE: PRT
<213> ORGANISM: Homo sapiens

<400> SEQUENCE: 8

Met Arg Arg Gly Pro Arg Ser Leu Arg Gly Arg Asp Ala Pro Ala Pro
1               5                   10                  15

Thr Pro Cys Val Pro Ala Glu Cys Phe Asp Leu Leu Val Arg His Cys
            20                  25                  30

Val Ala Cys Gly Leu Leu Arg Thr Pro Arg Pro Lys Pro Ala Gly Ala
        35                  40                  45

Ser Ser Pro Ala Pro Arg Thr Ala Leu Gln Pro Gln Glu Ser Val Gly
    50                  55                  60
```

```
Ala Gly Ala Gly Glu Ala Ala Leu Pro Leu Pro Gly Leu Leu Phe Gly
 65                  70                  75                  80

Ala Pro Ala Leu Leu Gly Leu Ala Leu Val Leu Ala Leu Val Leu Val
                 85                  90                  95

Gly Leu Val Ser Trp Arg Arg Arg Gln Arg Arg Leu Arg Gly Ala Ser
            100                 105                 110

Ser Ala Glu Ala Pro Asp Gly Asp Lys Asp Ala Pro Glu Pro Leu Asp
        115                 120                 125

Lys Val Ile Ile Leu Ser Pro Gly Ile Ser Asp Ala Thr Ala Pro Ala
130                 135                 140

Trp Pro Pro Pro Gly Glu Asp Pro Gly Thr Thr Pro Pro Gly His Ser
145                 150                 155                 160

Val Pro Val Pro Ala Thr Glu Leu Gly Ser Thr Glu Leu Val Thr Thr
                165                 170                 175

Lys Thr Ala Gly Pro Glu Gln Gln
            180
```

<210> SEQ ID NO 9
<211> LENGTH: 26
<212> TYPE: PRT
<213> ORGANISM: Homo sapiens

<400> SEQUENCE: 9

```
Met Ser Pro Thr Pro Cys Val Pro Ala Glu Cys Phe Asp Leu Leu Leu
  1               5                  10                  15

Arg His Cys Ile Ala Cys Gly Leu Leu Arg
             20                  25
```

<210> SEQ ID NO 10
<211> LENGTH: 8
<212> TYPE: PRT
<213> ORGANISM: Homo sapiens

<400> SEQUENCE: 10

```
Val His Val Phe Gly Asp Glu Leu
  1               5
```

<210> SEQ ID NO 11
<211> LENGTH: 34
<212> TYPE: PRT
<213> ORGANISM: Homo sapiens

<400> SEQUENCE: 11

```
Cys Ser Gln Asn Glu Tyr Phe Asp Ser Leu Leu His Ala Cys Ile Pro
  1               5                  10                  15

Cys Gln Leu Arg Cys Ser Ser Asn Thr Pro Pro Leu Thr Cys Gln Arg
             20                  25                  30

Tyr Cys
```

<210> SEQ ID NO 12
<211> LENGTH: 35
<212> TYPE: PRT
<213> ORGANISM: Homo sapiens

<400> SEQUENCE: 12

```
Cys Val Pro Ala Glu Cys Phe Asp Leu Leu Val Arg His Cys Val Ala
  1               5                  10                  15

Cys Gly Leu Leu Arg Thr Pro Arg Pro Lys Pro Ala Gly Ala Ser Ser
             20                  25                  30

Pro Ala Pro
```

```
<210> SEQ ID NO 13
<211> LENGTH: 33
<212> TYPE: PRT
<213> ORGANISM: Homo sapiens

<400> SEQUENCE: 13

Cys Pro Glu Glu Gln Tyr Trp Asp Pro Leu Leu Gly Thr Cys Met Ser
1               5                   10                  15

Cys Lys Thr Ile Cys Asn His Gln Ser Gln Arg Thr Cys Ala Ala Phe
            20                  25                  30

Cys

<210> SEQ ID NO 14
<211> LENGTH: 34
<212> TYPE: PRT
<213> ORGANISM: Homo sapiens

<400> SEQUENCE: 14

Cys Arg Lys Glu Gln Gly Lys Phe Tyr Asp His Leu Leu Arg Asp Cys
1               5                   10                  15

Ile Ser Cys Ala Ser Ile Cys Gly Gln His Pro Lys Gln Cys Ala Tyr
            20                  25                  30

Phe Cys

<210> SEQ ID NO 15
<211> LENGTH: 32
<212> TYPE: PRT
<213> ORGANISM: Homo sapiens

<400> SEQUENCE: 15

Cys Ser Arg Gly Ser Ser Trp Ser Ala Asp Leu Asp Lys Cys Met Asp
1               5                   10                  15

Cys Ala Ser Cys Arg Ala Arg Pro His Ser Asp Phe Cys Leu Gly Cys
            20                  25                  30

<210> SEQ ID NO 16
<211> LENGTH: 27
<212> TYPE: PRT
<213> ORGANISM: Homo sapiens

<400> SEQUENCE: 16

Cys His Met Gly Phe Phe Leu Lys Gly Ala Lys Cys Ile Ser Cys His
1               5                   10                  15

Asp Cys Lys Asn Lys Glu Cys Glu Lys Leu Cys
            20                  25
```